United States Patent
Perry et al.

(10) Patent No.: US 10,961,236 B2
(45) Date of Patent: Mar. 30, 2021

(54) (S)-2-(1-CYCLOPROPYLETHYL)-5-(4-METHYL-2-((6-(2-OXOPYRROLIDIN-1-YL)PYRIDIN-2-YL)AMINO)THIAZOL-5-YL)-7-(METHYLSULFONYL)ISOINDOLIN-1-ONE AS A PHOSPHATIDYLINOSITOL 3-KINASE INHIBITOR

(71) Applicant: AstraZeneca AB, Sodertalje (SE)

(72) Inventors: Matthew Perry, Cheshire (GB); Christian Tyrchan, Mölndal (SE); Konstantinos Karabelas, Mölndal (SE); Antonios Nikitidis, Mölndal (SE); Mickael Mogemark, Mölndal (SE); Jens Petersen, Mölndal (SE); Peter Bold, Mölndal (SE); Ulf Borjesson, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 128 days.

(21) Appl. No.: 16/332,620

(22) PCT Filed: Sep. 21, 2017

(86) PCT No.: PCT/EP2017/073916
§ 371 (c)(1),
(2) Date: Mar. 12, 2019

(87) PCT Pub. No.: WO2018/055040
PCT Pub. Date: Mar. 29, 2018

(65) Prior Publication Data
US 2020/0308164 A1    Oct. 1, 2020

Related U.S. Application Data

(60) Provisional application No. 62/398,006, filed on Sep. 22, 2016.

(51) Int. Cl.
*A61K 31/4439* (2006.01)
*C07D 213/72* (2006.01)
*C07D 417/14* (2006.01)

(52) U.S. Cl.
CPC .................. *C07D 417/14* (2013.01)

(58) Field of Classification Search
CPC .......................... A61K 31/4439; C07D 213/72
USPC .......................................... 514/352; 546/307
See application file for complete search history.

(56) References Cited

FOREIGN PATENT DOCUMENTS

| WO | 2004/078754 A1 | 9/2004 |
|---|---|---|
| WO | 2012052753 A1 | 4/2012 |
| WO | 2013012915 A1 | 1/2013 |
| WO | 2013012918 A1 | 1/2013 |
| WO | 2013032591 A1 | 3/2013 |
| WO | 2013052699 A2 | 4/2013 |
| WO | 2014124757 A1 | 8/2014 |
| WO | 2015001491 A1 | 1/2015 |
| WO | 2015010641 A1 | 1/2015 |
| WO | 2015198289 A1 | 12/2015 |

OTHER PUBLICATIONS

Rutaganira, et al., "Design and Structural Characterization of Potent and Selective Inhibitors of Phosphatidylinositol 4 Kinase IIIβ", Journal of Medicinal Chemistry, 2016, 59, 1830-1839.
Hawkins, et al., "PI3K signalling in inflammation", Biochim Biophys Acta. Jun. 2015;1851(6):882-97.
Cushing, et al., "PI3Kδ and PI3Kγ as targets for autoimmune and inflammatory diseases", J Med Chem. Oct. 25, 2012;55(20):8559-81.
Down, et al., "Optimization of Novel Indazoles as Highly Potent and Selective Inhibitors of Phosphoinositide 3-Kinase δ for the Treatment of Respiratory Disease", J. Med. Chem., 2015, 58 (18), pp. 7381-7399.
MS Thomas, et al., "The p110gamma isoform of phosphatidylinositol 3-kinase regulates migration of effector CD4 T lymphocytes into peripheral inflammatory sites", J Leuk Biol. 2008, 84;814-823.
AM Condliffe, et al., "Sequential activation of class IB and class IA PI3K is important for the primed respiratory burst of human but not murine neutrophils", Blood. Aug. 15, 2005;106(4):1432-40.
M Laffargue, et al., "Phosphoinositide 3-kinase gamma is an essential amplifier of mast cell function", Immunity. Mar. 2002;16(3), 441-51.
E Conte, et al., "PI3K p110γ overexpression in idiopathic pulmonary fibrosis lung tissue and fibroblast cells: in vitro effects of its inhibition", Lab Invest, May 2013, 93(5), 566-76.

*Primary Examiner* — Douglas M Willis

(57) ABSTRACT

Disclosed herein is the compound (S)-2-(1-cyclopropylethyl)-5-(4-methyl-2-((6-(2-oxopyrrolidin-1-yl)pyridin-2-yl)amino)thiazol-5-yl)-7-(methylsulfonyl)isoindolin-1-one of the following structure:

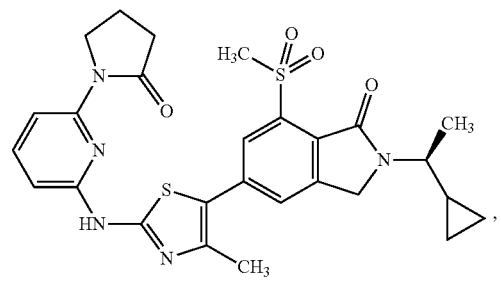

and/or pharmaceutically acceptable salts and/or pharmaceutical compositions thereof, which inhibit phosphatidylinositol 3-kinase (PI3K) activity.

6 Claims, 9 Drawing Sheets

(S)-2-(1-CYCLOPROPYLETHYL)-5-(4-METHYL-2-((6-(2-OXOPYRROLIDIN-1-YL)PYRIDIN-2-YL)AMINO)THIAZOL-5-YL)-7-(METHYLSULFONYL)ISOINDOLIN-1-ONE AS A PHOSPHATIDYLINOSITOL 3-KINASE INHIBITOR

CROSS-REFERENCE TO RELATED APPLICATIONS

This application is a U.S. National Stage application of International Application No. PCT/EP2017/073916, filed on Sep. 21, 2017, said International Application No. PCT/EP2017/073916 claims benefit under 35 U.S.C. § 119(e) of U.S. Provisional Application No. 62/398,006 filed Sep. 22, 2016. Each of the above listed applications is incorporated by reference herein in its entirety for all purposes.

TECHNICAL FIELD

The technical field relates to certain novel chemical compounds (including pharmaceutically acceptable salts thereof), that inhibit phosphatidylinositol 3-kinase delta (PI3Kδ) and phosphatidylinositol 3-kinase gamma (PI3Kγ) activity, to their utility in treating and/or preventing clinical conditions including respiratory diseases, such as asthma and chronic obstructive pulmonary disease (COPD), to their use in therapy, to pharmaceutical compositions containing them and to processes for preparing such compounds.

BACKGROUND

The phosphoinositide 3-kinase (PI3K) family are central signaling elements in a diverse array of cellular functions, including growth, proliferation, migration and survival. PI3Ks function by phosphorylating the 3-hydroxyl position on the inositol ring of phosphoinositide lipids, and can be divided into three classes based upon domain structure, the type of lipid substrate they act upon, and mode of regulation [Biochim Biophys Acta, 1436 (1998), 127-150]. Class I PI3K catalytic subunits can be further subdivided into class 1A (isoforms α, β, δ) and class IB (γ isoform) based on their catalytic subunit. Class IA PI3Ks form heterodimers with a regulatory subunit (p85α/p55α/p50α/p85β or p55γ). Whereas PI3K α and β isoforms are ubiquitously expressed, PI3Kδ is largely restricted to myeloid and lymphoid cells, and can feature downstream of receptor tyrosine kinases, T & B cell receptors, toll-like receptors and co-stimulatory molecules [Okkenhaug, Ann Rev Immunol, 31 (2013), 675-704]. PI3Kγ expression is also largely restricted to immune cells (neutrophils, eosinophils, macrophages, dendritic cells, T cells and mast cells), as well as low levels in endothelium, airway smooth muscle cells and the heart [Curr Opin Cell Biol, 17 (2005), 141-149]. PI3Kγ is activated by G-protein-coupled receptors (GPCRs) via association with either p101 or p84/p87 adaptors, which potentiate activation by βγ-subunits of hetero-trimeric GTP-binding proteins [Curr Biol, 15 (2005), 566-570]. Class 1 PI3Ks convert phosphatidylinositol 4,5-bisphosphate (PtdIns(4,5)P2) to form PtdIns(3,4,5)P3 in vivo [Biochim Biophys Acta, 1179 (1993), 27-75 and Science, 296 (2002), 1655-1657]. The PtdIns(3,4,5)P3 generated at the plasma membrane serves as a docking site for pleckstrin-homology (PH)-domain containing proteins such as protein kinase B (PKB/Akt), which can then influence a broad array of proteins and thereby effect many different cellular responses [Cell, 129 (2007), 1261-1274]. PI3Kδ kinase dead knock-in mice and PI3Kγ knockout mouse strains are viable and fertile and have been studied in a wide variety of preclinical models—identifying the δ isoform as having multiple roles in adaptive immunity and the γ isoform as a biochemical compass for migrating cells, particularly those of the innate immune system [Science, 287 (2000), 1049-1052 and Science, 297 (2002), 1031-1034]. The adaptive immune system relies on the presentation of antigen by professional presenting cells (macrophages, dendritic cells (DCs) and B cells) to T lymphocytes in lymph nodes which drain the site of antigen entry/discovery. PI3Kδ signaling is key to T lymphocyte stimulation, as demonstrated in kinase-dead knock-in animals which show defective signaling through the antigen complex and also costimulatory molecules [EMBO J. 1999; 18(5):1292-302]. Interestingly, humans with activating PI3Kδ mutations are also characterized by defective immunity, indicating the fine balance of PI3Kδ signaling necessary for effective functional responses [Clin Exp Immunol. 2016; 183(2):221-9]. PI3Kγ has been shown to be essential in the lung-specific development of DCs, as well as in effective trafficking to lymph nodes [Immunity 2015, 43, 674-689 and EMBO J. 2004, 23(17), 3505-15]. Once presented to a T cell with the appropriate affinity, a process of clonal expansion and differentiation into different subtypes occurs. CD4 T cell subsets can be broadly dived into Th1, Th2 and Th17 which help B lymphocyte responses and recruit granulocytes, or T reg cells which dampen the immune response. We and others show PI3Kδ to be essential for cytokine production from T cell subsets—an important feature of subset maturation [Blood. 2010, 115; 2203-2213]. PI3Kγ plays a lesser role in the T cell differentiation process, yet has been shown to be needed for optimal responses [Eur J Immunol. 2013, 43, 3183-3196]. Although the γ isoform is reportedly central to the migration of lymphocytes to sites of inflammation via chemokine/GPCR stimuli, it is also recognized that PI3Kδ may contribute through interaction with integrins—evidence supported by our findings of more effective dual inhibition of CD4 T cell movement [J Leuk Biol. 2008, 84; 814-823]. CD4 T cell 'help' for B cells to generate antibody responses is perturbed in the absence of PI3Kδ, both with respect to reduced cytokine production and signaling via co-stimulatory CD40, though seemingly less so via the B cell receptor itself [J Immunol. 2010. 185; 4042-4052]. Interestingly, a decrease in marginal zone B cells in rodents lacking PI3Kδ can lead to aberrant control of class switching and paradoxically enhanced IgE production [J Immunol. 2012, 188; 3700-3708].

Dysregulation of the adaptive immune system can result in chronic inflammation or autoimmunity, in which T cell subsets react inappropriately to innocuous antigen sampled from the environment (eg. grass pollen allergy) or from 'self' (eg. rheumatoid arthritis). There is evidence for PI3Kγ driving the priming and survival of such populations, particularly in central nervous system (CNS) related inflammatory disorders, such as Multiple Sclerosis (MS) [PLoS One. 2012, 7(9)]. However, PI3Kδ has been shown to feature at the heart of aberrant T/B lymphocyte responses [Biochem Biophys Acta. 2015. 1851; 882-897].

Cells of the innate immune response, including neutrophils, eosinophils, macrophages and mast cells, offer the first line of host defense against invading pathogens, yet it is often their extended/perpetual activation via dysregulated T cells which underlie the hallmark chronic inflammation in pulmonary diseases such as asthma and COPD. Early responders to damage/infection are neutrophils, where pro-inflammatory mediators and chemotactic factors activate and draw them to the site of injury, where they act to engulf bacteria by phagocytosis, then use a powerful serine protease—neutrophil elastase—to kill the pathogen. Yet neutrophil elastase can also cause problems for its host by degrading extracellular matrix proteins and coagulation, complement and immunoglobulin factors. Usually controlled by al-antitrypsin, neutrophil elastase evades regulation at inflammatory sites to induce further damage and release pro-inflammatory cytokines, such as IL-6 and IL-8. Neutrophil influx/activation is seen in numerous diseases, including hereditary emphysema, chronic obstructive pulmonary disease, cystic fibrosis, adult respiratory distress syndrome, ischemic-reperfusion injury and rheumatoid arthritis. Both PI3Kδ and γ isoform signaling are important in the generation of reactive oxygen species within neutrophils [Blood. 2005. 106, 1432-1440]. Whereas in vitro and in vivo studies have shown PI3Kγ to be central in the homing of neutrophils to sites of inflammation and their degranulation and elastase release [Curr Top Microbiol Immunol. 2010, 346, 183-202]. Eosinophils also derive from the bone marrow and circulate at low levels in the blood in healthy individuals. Stimulation by IL-5, potentially from activated T cells, innate lymphoid cells (ILC2s) or other eosinophils, will enhance circulating eosinophil numbers [FASEB J. 2006 March; 20(3), 455-65 and Anderson et al. Allergy. 2016 DOI: 10.1111/all. 12861]. Our data from stimulated peripheral blood mononuclear cells, or enriched ILC populations suggest a role for PI3Kδ in the release of IL-5 from both populations. In diseases such as allergic inflammation or eosinophilic granulomatosis with polyangiitis (EGPA), eosinophils leave the circulation and migrate to tissues, often in response to the GPCR chemokine ligand eotaxin. Evidence from animal model-based research has suggested deficiency of PI3Kγ impaired the migration of eosinophils both in vitro and in vivo [Immunology. 2009, 126(3), 413-22], with further supporting data demonstrating a protective phenotype of knockout mice within an OVA/alum model of asthma [J Leukoc Biol, 77 (2005), 800-810]. Human in vitro data also show a role for PI3Kγ in chemotaxis, adhesion and eosinophil-derived neurotoxin (EDN) release in response to eotaxin stimulation [Pulm Pharmacol Ther. 2014 April; 27(2), 164-9].

Macrophages are found in tissues throughout the body and form one of the first lines of defense to injury and pathogens, and are involved in diseases such as COPD. Since β1- and β2-integrin dependent monocyte adhesion and migration require PI3Kδ, its inhibition should impair the increased monocyte infiltration observed in COPD [Microcirculation. 2006. 13:6, 439-456]. PI3Kδ expression and signaling is increased in the lungs of patients with COPD. Selective inhibition of PI3Kδ restored glucocorticoid responsiveness ex vivo [J Allergy Clin Immunol. 2010; 125(5), 1146-53]. Early experiments in PI3Kγ knockout mice demonstrated that macrophages derived from mutant animals failed to produce PtdIns(3,4,5)P3 in response to stimulation with various chemotactic substances and that subsequent movement was inhibited [Science. 2000, 287 (5455), 1040-6]. Macrophages can be further divided into proinflammatory (M1) and the "alternatively activated" anti-inflammatory (M2) macrophages, which often play sequential roles in inflammation and repair/remodeling respectively. Chemokines are the major mediators of chemotaxis in both subsets, yet the pattern of GPCR expression which control cell movement differ. Chemokines CCL19 or CCL21 induced activation of both MEK1-ERK1/2 and PI3K-AKT cascades in M1 but not in M2 macrophages, although pan PI3K inhibition via wortmannin was able to block migration, presumably through lack of PI3Kγ activity [J Leukoc Biol. 2015, 97(1), 61-9]. Furthermore, a skewing toward M2 activated macrophages was sensitive to PI3Kδ inhibition when modeled in IL-4-stimulated murine systems [Eur. J. Immunol. 2011. 41, 1742-1753]. Lastly, PI3Kγ knockout mice show abrogated atherosclerosis by reducing macrophage proliferation (but not polarization or apoptosis) in lesions [PLoS One. 2013 Aug. 22; 8(8):e72674].

Two types of mast cells have been identified—T-type, which express only tryptase, and the TC-type, which express both tryptase and chymase. In humans, the T-type mast cells are located primarily in alveolar tissue and intestinal mucosa while the TC-type cells predominate in skin and conjunctiva. Tryptase and chymase appear to be important mediators of allergic diseases, being involved in processes of inflammation, bronchoconstriction, mucus secretion and tissue remodelling. Mast cell activation by IgE and survival via c-kit stimulation is reliant upon PI3Kδ signaling [Nature 2004. 431, 1007-1011]. PI3Kγ has been shown to play a key role in both the localization/retention of mast cells to sites of inflammation [J Allergy Clin Immunol. 2013, 132(4), 959-68]. Furthermore efficient degranulation requires secondary paracrine stimulation of adenosine via PI3Kγ, thus indicating a true partnership between PI3Kδ and γ isoforms for mast cell-mediated pathology in pulmonary diseases such as asthma [Immunity. 2002 March; 16(3), 441-51]). Beyond effects on adaptive or innate immunity, there is emerging data suggesting roles for PI3Kγ and δ isoforms in lung structural cell biology. Airway smooth muscle cell expression of PI3Kγ has been linked with the desensitization of β2 adrenergic receptors following agonism—a common treatment for bronchoconstriction in asthma. The mechanism appears to be via the sequestration of internalized receptor in the endoplasmic reticulum, thus inhibition of PI3Kγ may return some efficacy of β2 agonists which has been lost through long term use [PLoS One. 2015, 10(5), e0125803].

Fibrosis is a hallmark of most chronic lung diseases, although location and severity can vary dramatically. Fibroblast mesenchymal transition (FMT), in which fibroblasts differentiate in response to TGFβ into myofibroblasts is key to this pathologic process. Emerging data from idiopathic pulmonary fibrosis immunohistochemical sections showed increased PI3Kγ, yet no change in α, β or δ isoforms. Furthermore, PI3Kγ selective inhibition (via siRNA or AS252424 treatment) could decrease both FMT and fibroblast proliferation in vitro, thus suggesting a potential role for the γ isoform in lung tissue fibrosis [Lab Invest. 2013, 93(5), 566-76].

Both PI3Kγ and δ isoforms have been identified as important signaling mediators in cancer. PI3Kγ upregulation has been shown to be oncogenic in cancers such as pancreatic intraepithelial neoplasia and ductal carcinoma [Clin Cancer Res. 2010, 16(20), 4928-37], and has had roles in both tumor growth and metastasis shown in rodent oncology models [Oncogene. 2012, 31(18), 2350-61]. An indirect role for PI3Kγ has been demonstrated in promoting an immunosuppressive tumor microenvironment which contributes to the evasion of cancer cells from the immune system—a process which underlies relapse to current checkpoint and anti-angiogenic inhibitor therapies. Myeloid derived suppressor cells (MDSCs) are central to said immune evasion, through signaling mechanisms which feature PI3Kγ not only downstream of GPCRs but also cytokine and growth factor receptors [Cancer Cell. 2011, 19(6), 715-27 and Cell Rep. 2015, 11(4), 577-91]. Results indicate that upregulated PI3Kγ conveys the metastatic signal initiated by GPCRs in breast cancer cells, and suggest that PI3Kγ may be a novel therapeutic target for development of chemotherapeutic agents to prevent breast cancer metastasis. [Biochem. Pharm. 2013, 85, 1454-1462]. Furthermore, where active T reg immunity confers a tumourigenic environment, recent findings suggest a unique sensitivity to PI3Kδ inhibition, and thus the potential for therapeutic inhibition in tumours where T regs are dominant [Nature. 2014. 510; 407-411]. Yet PI3Kδ is also reported to be essential for tumour clearance by cytotoxic T lymphocytes (CTLs) [PLoS ONE. 2012. 7; e40852]. We and others have shown CTL migration to be sensitive to PI3Kγ inhibition, and thus may impact the killing of cells which present antigen from within (e.g. virus infected cells, cancer) [J Immunol. 2008. 180; 2081-2088]. Therefore, class IA PI3Kδ downstream of receptors for cytokines, growth factors, immunoglobulins, integrins and antigen receptor complexes, together with class IB PI3Kγ activity downstream of GPCRs, reveal important roles for both isoforms either individually or in concert, within a wide array of immune cell and responses. Pulmonary PI3Kγδ dual inhibition may treat complex multi-cellular diseases characterized by lung tissue adaptive immune T cell activation and consequent granulocyte influx and activation, such as is found in asthma, COPD and beyond [Biochim Biophys Acta. 2015 June, 1851(6), 882-97].

J. Med. Chem. 2012, 55, 8559-8581 highlights the roles of PI3Kδ and PI3Kγ as targets in autoimmune and inflammatory diseases and summarize the efforts toward the development of small molecule inhibitors of PI3Kδ and PI3Kγ as well as dual inhibitors. WO2012052753 discloses 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide as a dual PI3Kδ and PI3Kγ inhibitor. WO2013052699 disclose compounds capable of selectively inhibiting PI3Kδ and PI3Kγ. WO2013012915, WO2013012918, WO2013032591, WO2014124757, WO2015001491 and WO2015010641 disclose compounds capable of selectively inhibiting PI3Kδ and/or PI3Kγ. WO2015198289 disclose substituted chromene derivatives as selective dual inhibitors of PI3Kδ and PI3Kγ.

J. Med. Chem. 2015, 58, 7831-7399 discloses selective inhibitors of PI3Kδ for the treatment of respiratory indications via inhalation.

An object is to provide novel dual inhibitors of PI3Kδ and PI3Kγ useful in therapy. A further object is to provide dual inhibitors of PI3Kδ and PI3Kγ displaying selectivity over the PI3K class 1A isoforms α and β.

SUMMARY

There is provided compounds that are dual inhibitors of phosphatidylinositol 3-kinase delta (PI3Kδ) and phosphatidylinositol 3-kinase gamma (PI3Kγ), their use as medicaments, pharmaceutical compositions containing them and synthetic routes to their production.

According to a first aspect, there is provided a compound of formula (I)

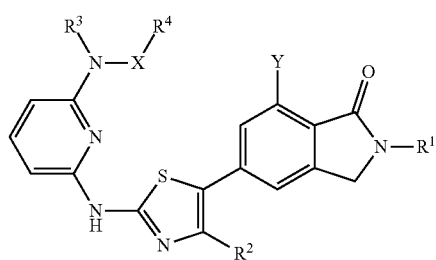

(I)

wherein
X is C(O) or $SO_2$;
Y is $SO_2NHR^5$ or $SO_2R^6$;
$R^1$ is selected from $C_{1-4}$alkyl, wherein said $C_{1-4}$alkyl is optionally substituted by cyclopropyl, 0, 1 or 2 $CH_3$ and 0, 1, 2 or 3 F;
$R^2$ is selected from H or $CH_3$;
$R^3$ is selected from H or $C_{1-3}$alkyl;
$R^4$ is selected from $C_{1-3}$alkyl, wherein said $C_{1-3}$alkyl is optionally substituted by $OC_{1-3}$alkyl; or
$R^3$ and $R^4$ taken together with the N atom and X form a 5, 6 or 7-membered cycloheteroalkylring containing 0 or 1 further heteroatoms selected from N or O, wherein said cycloheteroalkylring is substituted by 0, 1 or 2 substituents independently selected from $CH_3$, OH, $CH_2OH$ or $CH_2CH_2OH$; or
$R^3$ and $R^4$ taken together with the N atom and X are selected from

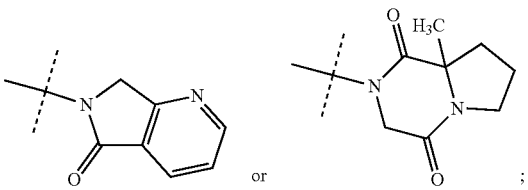

$R^5$ is selected from $C_{1-3}$alkyl or (oxetan-3-yl);
$R^6$ is selected from $C_{1-3}$alkyl;
or a pharmaceutically acceptable salt thereof.

The compounds of formula (I) are inhibitors of PI3Kδ and PI3Kγ. Thus, the compounds of formula (I) can be used as a medicament, in particular for disorders, disease or conditions responsive to inhibition of PI3Kδ and/or PI3Kγ, and more specifically respiratory diseases (such as COPD and asthma).

In another embodiment there is provided a compound of formula (I), or a pharmaceutically acceptable salt of a compound of formula (I), wherein the stereochemistry is undefined, e.g. a racemate or a mixture of diastereomers.

In another embodiment there is provided a pharmaceutical formulation comprising a therapeutically effective amount of a compound of formula (I), or a pharmaceutically acceptable salt of a compound of formula (I), and a pharmaceutically acceptable diluent, excipient and/or inert carrier.

In a further embodiment there is provided a pharmaceutical formulation comprising a compound of formula (I), or a pharmaceutically acceptable salt of a compound of formula (I), for use in the treatment of a condition where inhibition of PI3Kδ and/or PI3Kγ would be beneficial.

In a further embodiment there is provided a compound of formula (I), or a pharmaceutically acceptable salt of a compound of formula (I), for use in therapy, especially in the prevention or treatment of respiratory disease in a mammal, particularly a human.

In a further embodiment there is provided a compound of formula (I), or a pharmaceutically acceptable salt of a compound of formula (I), for use in therapy, especially in the prevention or treatment of asthma in a mammal, particularly a human.

In a further embodiment there is provided a compound of formula (I), or a pharmaceutically acceptable salt of a compound of formula (I), for use in therapy, especially in the prevention or treatment of COPD in a mammal, particularly a human.

In a further embodiment there is provided the use of a compound of formula (I), or a pharmaceutically acceptable salt of a compound of formula (I), for the manufacture of a medicament for the treatment and prevention of respiratory disease.

In a further embodiment there is provided the use of a compound of formula (I), or a pharmaceutically acceptable salt of a compound of formula (I), for the manufacture of a medicament for the treatment and prevention of asthma.

In a further embodiment there is provided the use of a compound of formula (I), or a pharmaceutically acceptable salt of a compound of formula (I), for the manufacture of a medicament for the treatment and prevention of COPD.

In still a further embodiment, administration of a compound of formula (I), or a pharmaceutically acceptable salt of a compound of formula (I) results in a reduction in levels of activity of PI3Kδ and/or PI3Kγ in a mammal, particularly a human.

According to another aspect there is provided a process for the preparation of compounds of formula (I), or pharmaceutically acceptable salts of compounds of formula (I), and the intermediates used in the preparation thereof.

The compounds of formula (I) herein exemplified have an $IC_{50}$ of less than 100 nmol/L for PI3Kδ and PI3Kγ in enzymatic activity assays. The compounds of formula (I) also display promising pharmacological profiles by separating desired and undesired effects in vivo.

DETAILED DESCRIPTION

Figure 1:
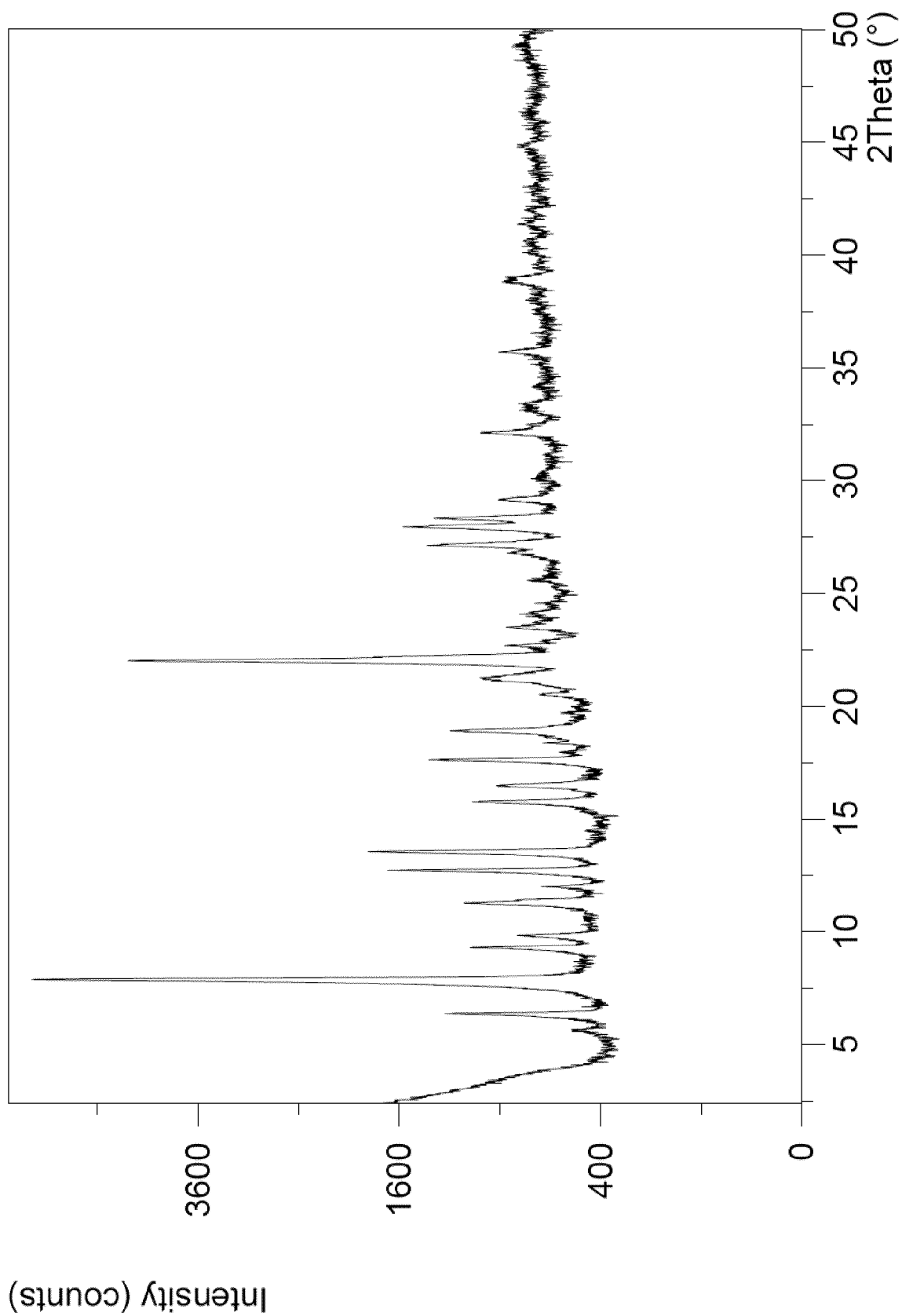
FIG. 1 shows the X-ray powder diffraction pattern for Example 1, form B: 2-[(1S)-1-Cyclopropylethyl]-5-(4-methyl-2-{[6-(2-oxopyrrolidin-1-yl)pyridin-2-yl]amino}-1,3-thiazol-5-yl)-7-(methylsulfonyl)-2,3-dihydro-1H-isoindol-1-one.

This detailed description and its specific examples, while indicating embodiments, are intended for purposes of illustration only. Therefore, there is no limitation to the illustrative embodiments described in this specification. In addition, it is to be appreciated that various features that are, for clarity reasons, described in the context of separate embodiments, also may be combined to form a single embodiment. Conversely, various features that are, for brevity reasons, described in the context of a single embodiment, also may be combined to form subcombinations thereof.

Listed below are definitions of various terms used in the specification and claims.

For the avoidance of doubt it is to be understood that where in this specification a group is qualified by "defined above" the said group encompasses the first occurring and broadest definition as well as each and all of the other definitions for that group.

For the avoidance of doubt it is to be understood that in this specification "$C_{1-4}$" means a carbon group having 1, 2, 3 or 4 carbon atoms.

For the avoidance of doubt it is to be understood that in this specification "$C_{1-3}$" means a carbon group having 1, 2 or 3 carbon atoms.

In this specification, unless stated otherwise, the term "alkyl" includes both straight and branched chain alkyl groups and may be, but is not limited to, methyl, ethyl, n-propyl, i-propyl, n-butyl, sec-butyl, iso-butyl or tert-butyl.

In this specification, unless stated otherwise, the term "pharmaceutically acceptable" is used to characterize a moiety (e.g. a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

There is provided compounds of formula (I) wherein X, Y and $R^1$-$R^6$ are as defined in formula (I).

In one embodiment X is C(O) or $SO_2$.
In a further embodiment X is C(O).
In still a further embodiment X is $SO_2$.
In one embodiment Y is $SO_2NHR^5$ or $SO_2R^6$;
$R^5$ is selected from $C_{1-3}$alkyl or (oxetan-3-yl);
$R^6$ is selected from $C_{1-3}$alkyl.
In a further embodiment Y is $SO_2NHR^5$;
$R^5$ is selected from $C_{1-3}$alkyl or (oxetan-3-yl).
In still a further embodiment Y is $SO_2R^6$;
$R^6$ is selected from $C_{1-3}$alkyl.
In one embodiment $R^1$ is selected from $C_{1-4}$alkyl, wherein said $C_{1-4}$alkyl is optionally substituted by cyclopropyl, 0, 1 or 2 $CH_3$ and 0, 1, 2 or 3 F.
In a further embodiment $R^1$ is selected from tert-butyl, butan-2-yl, 3,3-dimethylbutan-2-yl, 1,1,1-trifluoropropan-2-yl, 1-cyclopropylethyl.
In still a further embodiment $R^1$ is selected from 1,1,1-trifluoropropan-2-yl or 1-cyclopropylethyl.

In still a further embodiment $R^1$ is 1,1,1-trifluoropropan-2-yl.

In still a further embodiment $R^1$ is (2S)-1,1,1-trifluoropropan-2-yl.

In still a further embodiment $R^1$ is 1-cyclopropylethyl.

In still a further embodiment $R^1$ is (1S)-1-cyclopropylethyl.

In one embodiment $R^2$ is selected from H or $CH_3$.

In a further embodiment $R^2$ is H.

In still a further embodiment $R^2$ is $CH_3$.

In one embodiment $R^3$ is selected from H or $C_{1-3}$alkyl.

In a further embodiment $R^3$ is $CH_3$.

In one embodiment $R^4$ is selected from $C_{1-3}$alkyl, wherein said $C_{1-3}$alkyl is optionally substituted by $OC_{1-3}$alkyl.

In a further embodiment $R^4$ is $CH_3$.

In one embodiment $R^3$ and $R^4$ taken together with the N atom and X form a 5, 6 or 7-membered cycloheteroalkylring containing 0 or 1 further heteroatoms selected from N or O, wherein said cycloheteroalkylring is substituted by 0, 1 or 2 substituents independently selected from $CH_3$, OH, $CH_2OH$ or $CH_2CH_2OH$;

X is C(O) or $SO_2$.

In a further embodiment $R^3$ and $R^4$ taken together with the N atom and X form a 7-membered cycloheteroalkylring containing 1 further N;

X is C(O).

In still a further embodiment $R^3$ and $R^4$ taken together with the N atom and X form a 6-membered cycloheteroalkylring containing 0 or 1 further heteroatoms selected from N or O, wherein said cycloheteroalkylring is substituted by 0, 1 or 2 substituents independently selected from $CH_3$ or $CH_2CH_2OH$;

X is C(O).

In still a further embodiment $R^3$ and $R^4$ taken together with the N atom and X form a 5-membered cycloheteroalkylring containing 0 or 1 further heteroatoms selected from N or O, wherein said cycloheteroalkylring is substituted by 0 or 1 substituents independently selected from $CH_3$, OH, or $CH_2OH$;

X is C(O).

In still a further embodiment $R^3$ and $R^4$ taken together with the N atom and X form 2-oxopyrrolidin-1-yl;

X is C(O).

In still a further embodiment $R^3$ and $R^4$ taken together with the N atom and X are selected from

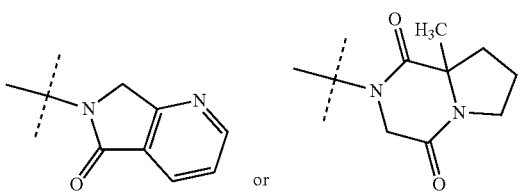

or

In one embodiment $R^5$ is selected from $C_{1-3}$alkyl or (oxetan-3-yl).

In a further embodiment $R^5$ is selected from $C_{1-3}$alkyl.

In still a further embodiment $R^5$ is $CH_3$.

In still a further embodiment $R^5$ is (oxetan-3-yl).

In one embodiment $R^6$ is selected from $C_{1-3}$alkyl.

In a further embodiment $R^6$ is $CH_3$.

One or more above embodiments may be combined to provide further specific embodiments.

In one embodiment the compound of formula (I) is selected from:

2-[(1S)-1-Cyclopropylethyl]-5-(4-methyl-2-{[6-(2-oxopyrrolidin-1-yl)pyridin-2-yl]amino}-1,3-thiazol-5-yl)-7-(methylsulfonyl)-2,3-dihydro-1H-isoindol-1-one, N-{6-[(5-{2-[(1S)-1-Cyclopropylethyl]-7-(methylsulfonyl)-1-oxo-2,3-dihydro-1H-isoindol-5-yl}-4-methyl-1,3-thiazol-2-yl)amino]pyridin-2-yl}acetamide, N-{6-[(5-{2-[(1S)-1-Cyclopropylethyl]-7-(methylsulfonyl)-1-oxo-2,3-dihydro-1H-isoindol-5-yl}-4-methyl-1,3-thiazol-2-yl)amino]pyridin-2-yl}-N-methylacetamide, 2-[(1S)-1-Cyclopropylethyl]-5-(4-methyl-2-{[6-(2-oxopiperidin-1-yl)pyridin-2-yl]amino}-1,3-thiazol-5-yl)-7-(methylsulfonyl)-2,3-dihydro-1H-isoindol-1-one, 2-[(1S)-1-Cyclopropylethyl]-5-(4-methyl-2-{[6-(3-methyl-2-oxoimidazolidin-1-yl)pyridin-2-yl]amino}-1,3-thiazol-5-yl)-7-(methylsulfonyl)-2,3-dihydro-1H-isoindol-1-one, 2-[(1S)-1-Cyclopropylethyl]-5-(4-methyl-2-{[6-(2-oxoimidazolidin-1-yl)pyridin-2-yl]amino}-1,3-thiazol-5-yl)-7-(methylsulfonyl)-2,3-dihydro-1H-isoindol-1-one, 2-[(1S)-1-Cyclopropylethyl]-5-(4-methyl-2-{[6-(3-oxomorpholin-4-yl)pyridin-2-yl]amino}-1,3-thiazol-5-yl)-7-(methylsulfonyl)-2,3-dihydro-1H-isoindol-1-one, 2-[(1S)-1-Cyclopropylethyl]-5-(4-methyl-2-{[6-(2-oxo-1,3-oxazinan-3-yl)pyridin-2-yl]amino}-1,3-thiazol-5-yl)-7-(methylsulfonyl)-2,3-dihydro-1H-isoindol-1-one, 6-{6-[(5-{2-[(1S)-1-Cyclopropylethyl]-7-(methylsulfonyl)-1-oxo-2,3-dihydro-1H-isoindol-5-yl}-4-methyl-1,3-thiazol-2-yl)amino]pyridin-2-yl}-6,7-dihydro-5H-pyrrolo[3,4-b]pyridin-5-one, 5-(4-Methyl-2-{[6-(2-oxopyrrolidin-1-yl)pyridin-2-yl]amino}-1,3-thiazol-5-yl)-7-(methylsulfonyl)-2-[(2S)-1,1,1-trifluoropropan-2-yl]-2,3-dihydro-1H-isoindol-1-one, 5-(4-Methyl-2-{[6-(2-oxoimidazolidin-1-yl)pyridin-2-yl]amino}-1,3-thiazol-5-yl)-7-(methylsulfonyl)-2-[(2S)-1,1,1-trifluoropropan-2-yl]-2,3-dihydro-1H-isoindol-1-one, 5-(4-Methyl-2-{[6-(2-oxo-1,3-oxazolidin-3-yl)pyridin-2-yl]amino}-1,3-thiazol-5-yl)-7-(methylsulfonyl)-2-[(2S)-1,1,1-trifluoropropan-2-yl]-2,3-dihydro-1H-isoindol-1-one, N-{6-[(5-{2-[(1S)-1-Cyclopropylethyl]-7-(methylsulfamoyl)-1-oxo-2,3-dihydro-1H-isoindol-5-yl}-4-methyl-1,3-thiazol-2-yl)amino]pyridin-2-yl}-N-methylacetamide, N-{6-[(5-{2-[(1S)-1-Cyclopropylethyl]-7-(methylsulfamoyl)-1-oxo-2,3-dihydro-1H-isoindol-5-yl}-4-methyl-1,3-thiazol-2-yl)amino]pyridin-2-yl}-2-methoxy-N-methylacetamide, (2R)—N-{6-[(5-{2-[(1S)-1-Cyclopropylethyl]-7-(methylsulfamoyl)-1-oxo-2,3-dihydro-1H-isoindol-5-yl}-4-methyl-1,3-thiazol-2-yl)amino]pyridin-2-yl}-2-methoxy-N-methylpropanamide, (2S)—N-{6-[(5-{2-[(1S)-1-Cyclopropylethyl]-7-(methylsulfamoyl)-1-oxo-2,3-dihydro-1H-isoindol-5-yl}-4-methyl-1,3-thiazol-2-yl)amino]pyridin-2-yl}-2-methoxy-N-methylpropanamide, N-{6-[(5-{2-[(1S)-1-Cyclopropylethyl]-7-(methylsulfamoyl)-1-oxo-2,3-dihydro-1H-isoindol-5-yl}-4-methyl-1,3-thiazol-2-yl)amino]pyridin-2-yl}-2-ethoxy-N-methylacetamide, 2-[(1S)-1-Cyclopropylethyl]-N-methyl-6-(4-methyl-2-{[6-(2-oxopiperidin-1-yl)pyridin-2-yl]amino}-1,3-thiazol-5-yl)-3-oxo-2,3-dihydro-1H-isoindole-4-sulfonamide, 2-[(1S)-1-Cyclopropylethyl]-N-methyl-6-(4-methyl-2-{[6-(3-oxomorpholin-4-yl)pyridin-2-yl]amino}-1,3-thiazol-5-yl)-3-oxo-2,3-dihydro-1H-isoindole-4-sulfonamide, 2-[(1S)-1-Cyclopropylethyl]-N-methyl-6-(4-methyl-2-{[6-(2-oxo-1,3-oxazinan-3-yl)pyridin-2-yl]amino}-1,3-thiazol-5-yl)-3-oxo-2,3-dihydro-1H-isoindole-4-sulfonamide, 2-[(1 S)-1-Cyclopropylethyl]-N-methyl-6-(4-methyl-2-{[6-(4-methyl-2-oxopiperazin-1-yl)pyridin-2-yl]amino}-1,3-thiazol-5-yl)-3-oxo-2,3-dihydro-1H-isoindole-4-sulfonamide, 2-[(1S)-1-Cyclopropylethyl]-6-[2-({6-[(8aS)-1,4-dioxohexahydropyrrolo[1,2-a]pyrazin-2(1H)-yl]pyridin-2-yl}amino)-4-methyl-1,3-thiazol-5-yl]-N-methyl-3-oxo-2,3-dihydro-1H-isoindole-4-sulfonamide, 2-[(1S)-1-Cyclopropylethyl]-6-(2-{[6-(1,1-dioxido-1,2-thiazolidin-2-yl)pyridin-2-yl]amino}-4-methyl-1,3-thiazol-5-yl)-N-methyl-3-oxo-2,3-dihydro-1H-isoindole-4-sulfonamide, N-Methyl-6-(4-methyl-2-{[6-(2-oxopyrrolidin-1-yl)pyridin-2-yl]amino}-1,3-thiazol-5-yl)-3-oxo-2-[(2S)-1,1,1-trifluoropropan-2-yl]-2,3-dihydro-1H-isoindole-4-sulfonamide, N-{6-[(5-{2-[(1S)-1-Cyclopropylethyl]-7-(ethylsulfamoyl)-1-oxo-2,3-dihydro-1H-isoindol-5-yl}-4-methyl-1,3-thiazol-2-yl)amino]pyridin-2-yl}-2-methoxy-N-methylacetamide, N-Ethyl-6-(4-methyl-2-{[6-(3-oxomorpholin-4-yl)pyridin-2-yl]amino}-1,3-thiazol-5-yl)-3-oxo-2-[(2S)-1,1,1-trifluoropropan-2-yl]-2,3-dihydro-1H-isoindole-4-sulfonamide, 6-(4-Methyl-2-{[6-(3-oxomorpholin-4-yl)pyridin-2-yl]amino}-1,3-thiazol-5-yl)-3-oxo-N-(propan-2-yl)-2-[(2S)-1,1,1-trifluoropropan-2-yl]-2,3-dihydro-1H-isoindole-4-sulfonamide, 6-(4-Methyl-2-{[6-(2-oxo-1,3-oxazinan-3-yl)pyridin-2-yl]amino}-1,3-thiazol-5-yl)-3-oxo-N-(propan-2-yl)-2-[(2S)-1,1,1-trifluoropropan-2-yl]-2,3-dihydro-1H-isoindole-4-sulfonamide, 6-(4-Methyl-2-{[6-(2-oxoimidazolidin-1-yl)pyridin-2-yl]amino}-1,3-thiazol-5-yl)-3-oxo-N-(propan-2-yl)-2-[(2S)-1,1,1-trifluoropropan-2-yl]-2,3-dihydro-1H-isoindole-4-sulfonamide, 2-[(1S)-1-Cyclopropylethyl]-6-(4-methyl-2-{[6-(3-oxomorpholin-4-yl)pyridin-2-yl]amino}-1,3-thiazol-5-yl)-N-(oxetan-3-yl)-3-oxo-2,3-dihydro-1H-isoindole-4-sulfonamide, 2-[(1 S)-1-Cyclopropylethyl]-6-(4-methyl-2-{[6-(2-oxopyrrolidin-1-yl)pyridin-2-yl]amino}-1,3-thiazol-5-yl)-N-(oxetan-3-yl)-3-oxo-2,3-dihydro-1H-isoindole-4-sulfonamide, 2-[(1S)-1-Cyclopropylethyl]-6-(4-methyl-2-{[6-(2-oxo-1,3-oxazolidin-3-yl)pyridin-2-yl]amino}-1,3-thiazol-5-yl)-N-(oxetan-3-yl)-3-oxo-2,3-dihydro-1H-isoindole-4-sulfonamide, 2-[(1 S)-1-Cyclopropylethyl]-6-(4-methyl-2-{[6-(2-oxoimidazolidin-1-yl)pyridin-2-yl]amino}-1,3-thiazol-5-yl)-N-(oxetan-3-yl)-3-oxo-2,3-dihydro-1H-isoindole-4-sulfonamide, 2-[(1S)-1-Cyclopropylethyl]-6-(4-methyl-2-{[6-(2-oxo-1,3-oxazinan-3-yl)pyridin-2-yl]amino}-1,3-thiazol-5-yl)-N-(oxetan-3-yl)-3-oxo-2,3-dihydro-1H-isoindole-4-sulfonamide, 6-(4-Methyl-2-{[6-(2-oxopiperidin-1-yl)pyridin-2-yl]amino}-1,3-thiazol-5-yl)-N-(oxetan-3-yl)-3-oxo-2-[(2S)-1,1,1-trifluoropropan-2-yl]-2,3-dihydro-1H-isoindole-4-sulfonamide, 6-(4-Methyl-2-{[6-(2-oxopyrrolidin-1-yl)pyridin-2-yl]amino}-1,3-thiazol-5-yl)-N-(oxetan-3-yl)-3-oxo-2-[(2S)-1,1,1-trifluoropropan-2-yl]-2,3-dihydro-1H-isoindole-4-sulfonamide, 2-tert-Butyl-N-methyl-6-(4-methyl-2-{[6-(2-oxo-1,3-oxazinan-3-yl)pyridin-2-yl]amino}-1,3-thiazol-5-yl)-3-oxo-2,3-dihydro-1H-isoindole-4-sulfonamide, 2-[(2S)-3,3-Dimethylbutan-2-yl]-N-methyl-6-(4-methyl-2-{[6-(3-oxomorpholin-4-yl)pyridin-2-yl]amino}-1,3-thiazol-5-yl)-3-oxo-2,3-dihydro-1H-isoindole-4-sulfonamide, 2-[(1 S)-1-Cyclopropylethyl]-5-(4-methyl-2-{[6-(2-oxopiperazin-1-yl)pyridin-2-yl]amino}-1,3-thiazol-5-yl)-7-(methylsulfonyl)-2,3-dihydro-1H-isoindol-1-one, 2-[(1 S)-1-Cyclopropylethyl]-N-methyl-6-(4-methyl-2-{[6-(2-oxopiperazin-1-yl)pyridin-2-yl]amino}-1,3-thiazol-5-yl)-3-oxo-2,3-dihydro-1H-isoindole-4-sulfonamide, 2-[(1S)-1-Cyclopropylethyl]-N-methyl-6-[4-methyl-2-({6-[(5S)-5-methyl-2-oxopiperazin-1-yl]pyridin-2-yl}amino)-1,3-thiazol-5-yl]-3-oxo-2,3-dihydro-1H-isoindole-4-sulfonamide, 2-[(1S)-1-Cyclopropylethyl]-N-methyl-6-[4-methyl-2-({6-[(3R)-3-methyl-2-oxopiperazin-1-yl]pyridin-2-yl}amino)-1,3-thiazol-5-yl]-3-oxo-2,3-dihydro-1H-isoindole-4-sulfonamide, 2-[(1S)-1-Cyclopropylethyl]-N-methyl-6-[4-methyl-2-({6-[(3S)-3-methyl-2-oxopiperazin-1-yl]pyridin-2-yl}amino)-1,3-thiazol-5-yl]-3-oxo-2,3-dihydro-1H-isoindole-4-sulfonamide, 2-[(1S)-1-Cyclopropylethyl]-N-methyl-6-[4-methyl-2-({6-[(5R)-5-methyl-2-oxopiperazin-1-yl]pyridin-2-yl}amino)-1,3-thiazol-5-yl]-3-oxo-2,3-dihydro-1H-isoindole-4-sulfonamide, 2-[(1S)-1-Cyclopropylethyl]-N-methyl-6-[4-methyl-2-({6-[(2R)-2-methyl-6-oxopiperazin-1-yl]pyridin-2-yl}amino)-1,3-thiazol-5-yl]-3-oxo-2,3-dihydro-1H-isoindole-4-sulfonamide, 2-[(1S)-1-Cyclopropylethyl]-6-(2-{[6-(3,3-dimethyl-2-oxopiperazin-1-yl)pyridin-2-yl]amino}-4-methyl-1,3-thiazol-5-yl)-N-methyl-3-oxo-2,3-dihydro-1H-isoindole-4-sulfonamide, 2-[(1S)-1-Cyclopropylethyl]-6-(2-{[6-(5,5-dimethyl-2-oxopiperazin-1-yl)pyridin-2-yl]amino}-4-methyl-1,3-thiazol-5-yl)-N-methyl-3-oxo-2,3-dihydro-1H-isoindole-4-sulfonamide, 2-[(1S)-1-Cyclopropylethyl]-N-methyl-6-[4-methyl-2-({6-[(2S)-2-methyl-6-oxopiperazin-1-yl]pyridin-2-yl}amino)-1,3-thiazol-5-yl]-3-oxo-2,3-dihydro-1H-isoindole-4-sulfonamide, 2-[(1 S)-1-Cyclopropylethyl]-N-ethyl-6-(4-methyl-2-{[6-(2-oxopiperazin-1-yl)pyridin-2-yl]amino}-1,3-thiazol-5-yl)-3-oxo-2,3-dihydro-1H-isoindole-4-sulfonamide, 2-[(1S)-1-Cyclopropylethyl]-6-(4-methyl-2-{[6-(2-oxopiperazin-1-yl)pyridin-2-yl]amino}-1,3-thiazol-5-yl)-3-oxo-N-(propan-2-yl)-2,3-dihydro-1H-isoindole-4-sulfonamide, 2-[(1 S)-1-Cyclopropylethyl]-N-methyl-6-(4-methyl-2-{[6-(2-oxo-1,4-diazepan-1-yl)pyridin-2-yl]amino}-1,3-thiazol-5-yl)-3-oxo-2,3-dihydro-1H-isoindole-4-sulfonamide, 2-[(1 S)-1-Cyclopropylethyl]-N-methyl-6-(4-methyl-2-{[6-(7-oxo-1,4-diazepan-1-yl)pyridin-2-yl]amino}-1,3-thiazol-5-yl)-3-oxo-2,3-dihydro-1H-isoindole-4-sulfonamide, 2-[(1 S)-1-Cyclopropylethyl]-6-[2-({6-[(3R)-3-hydroxy-2-oxopyrrolidin-1-yl]pyridin-2-yl}amino)-4-methyl-1,3-thiazol-5-yl]-N-methyl-3-oxo-2,3-dihydro-1H-isoindole-4-sulfonamide, 2-[(1S)-1-Cyclopropylethyl]-6-[2-({6-[(4R)-4-hydroxy-2-oxopyrrolidin-1-yl]pyridin-2-yl}amino)-4-methyl-1,3-thiazol-5-yl]-N-methyl-3-oxo-2,3-dihydro-1H-isoindole-4-sulfonamide, 2-[(1S)-1-Cyclopropylethyl]-6-[2-({6-[(3S)-3-hydroxy-2-oxopyrrolidin-1-yl]pyridin-2-yl}amino)-4-methyl-1,3-thiazol-5-yl]-N-methyl-3-oxo-2,3-dihydro-1H-isoindole-4-sulfonamide, 2-[(1S)-1-Cyclopropylethyl]-6-[2-({6-[(2S)-2-(hydroxymethyl)-5-oxopyrrolidin-1-yl]pyridin-2-yl}amino)-4-methyl-1,3-thiazol-5-yl]-N-methyl-3-oxo-2,3-dihydro-1H-isoindole-4-sulfonamide, 2-[(1S)-1-Cyclopropylethyl]-6-[2-({6-[(2R)-2-(hydroxymethyl)-5-oxopyrrolidin-1-yl]pyridin-2-yl}amino)-4-methyl-1,3-thiazol-5-yl]-N-methyl-3-oxo-2,3-dihydro-1H-isoindole-4-sulfonamide, 2-[(1S)-1-Cyclopropylethyl]-6-[2-({6-[4-(2-hydroxyethyl)-2-oxopiperazin-1-yl]pyridin-2-yl}amino)-4-methyl-1,3-thiazol-5-yl]-N-methyl-3-oxo-2,3-dihydro-1H-isoindole-4-sulfonamide, 6-[2-({6-[(3S)-3-Hydroxy-2-oxopyrrolidin-1-yl]pyridin-2-yl}amino)-4-methyl-1,3-thiazol-5-yl]-3-oxo-N-(propan-2-yl)-2-[(2S)-1,1,1-trifluoropropan-2-yl]-2,3-dihydro-1H-isoindole-4-sulfonamide, 2-[(2S)-Butan-2-yl]-N-methyl-6-(4-methyl-2-{[6-(2-oxo-1,3-oxazinan-3-yl)pyridin-2-yl]amino}-1,3-thiazol-5-yl)-3-oxo-2,3-dihydro-1H-isoindole-4-sulfonamide, 2-[(2S)-Butan-2-yl]-N-methyl-6-(4-methyl-2-{[6-(3-oxomorpholin-4-yl)pyridin-2-yl]amino}-1,3-thiazol-5-yl)-3-oxo-2,3-dihydro-1H-isoindole-4-sulfonamide, N-Methyl-6-(4-methyl-2-{[6-(2-oxoimidazolidin-1-yl)pyridin-2-yl]amino}-1,3-thiazol-5-yl)-3-oxo-2-[(2S)-1,1,1-trifluoropropan-2-yl]-2,3-dihydro-1H-isoindole-4-sulfonamide, and pharmaceutically acceptable salts thereof.

It shall be noted that any one of these specific compounds may be disclaimed from any of the herein mentioned embodiments.

Another embodiment is a product obtainable by any of the processes or examples disclosed herein.

Pharmacological Properties

The compounds of formula (I) and their pharmaceutically acceptable salts have activity as pharmaceuticals, in particular as inhibitors of PI3Kδ and/or PI3Kγ activity, and thus may be used in the treatment of obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; alpha-1 antitrypsin deficiency; EGPA (Eosinophilic Granulocytic with Polyangiitis, also known as Churg-Strauss syndrome or allergic granulomatosis); ABPA (Allergic Broncopulmonary Aspergillosis); CEP (Chronic Eosinophilic Pneumonia); farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus, acute lung injury, adult respiratory distress syndrome (ARDS), as well as exacerbations of each of the foregoing respiratory tract disease states, in particular exacerbations of all types of asthma or COPD.

Thus, there is provided a compound of formula (I), or a pharmaceutically acceptable salt thereof, as hereinbefore defined for use in therapy.

In a further aspect, there is provided the use of a compound of formula (I), or a pharmaceutically acceptable salt thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, the compounds of formula (I), or a pharmaceutically acceptable salt thereof, may be used in the treatment of asthma {such as bronchial, allergic, intrinsic, extrinsic or dust asthma, particularly chronic or inveterate asthma (for example late asthma or airways hyper-responsiveness)}, chronic obstructive pulmonary disease (COPD) or allergic rhinitis.

There is also provided a method of treating, or reducing the risk of, an obstructive airways disease or condition (e.g. asthma or COPD) which comprises administering to a patient in need thereof a therapeutically effective amount of a compound of formula (I), or a pharmaceutically acceptable salt thereof, as hereinbefore defined.

In a further aspect, there is provided the use of a compound of formula (I), or a pharmaceutically acceptable salt thereof, as hereinbefore defined in the manufacture of a medicament for use in treating COPD.

In a further aspect, there is provided the use of a compound of formula (I), or a pharmaceutically acceptable salt thereof, as hereinbefore defined in the manufacture of a medicament for use in treating asthma.

In a further aspect, there is provided a compound of formula (I), or a pharmaceutically acceptable salt thereof, as hereinbefore defined for use in treating COPD.

In a further aspect, there is provided a compound of formula (I), or a pharmaceutically acceptable salt thereof, as hereinbefore defined for use in treating asthma.

Combination Therapy

The compounds of formula (I), or a pharmaceutically acceptable salt thereof, may also be administered in conjunction with other compounds used for the treatment of the above conditions.

In another embodiment, there is provided a combination therapy wherein a compound of formula (I), or a pharmaceutically acceptable salt thereof, and a second active ingredient are administered concurrently, sequentially or in admixture, for the treatment of one or more of the conditions listed above. Such a combination may be used in combination with one or more further active ingredients.

Another embodiment relates to the combination of a compound of formula (I), or a pharmaceutically acceptable salt thereof, together with an anti-inflammatory and/or bronchodilatory compound.

Another embodiment relates to the combination of a compound of formula (I), or a pharmaceutically acceptable salt thereof, together with a glucocorticoid receptor agonist (steroidal or non-steroidal).

Another embodiment still further relates to the combination of a compound of formula (I), or a pharmaceutically acceptable salt thereof, together with a selective β2 adrenoceptor agonist.

Another embodiment still further relates to the combination of a compound of formula (I), or a pharmaceutically acceptable salt thereof, together with an antimuscarinic agent.

Another embodiment still further relates to the combination of a compound of formula (I), or a pharmaceutically acceptable salt thereof, together with a dual β2 adrenoceptor agonist/antimuscarinic agent.

Another embodiment still further relates to the combination of a compound of formula (I), or a pharmaceutically acceptable salt thereof, together with a p38 antagonist.

Another embodiment still further relates to the combination of a compound of formula (I), or a pharmaceutically acceptable salt thereof, together with a xanthine derivative.

Another embodiment still further relates to the combination of a compound of formula (I), or a pharmaceutically acceptable salt thereof, together with a phosphodiesterase (PDE) inhibitor (including a PDE4 inhibitor or an inhibitor of the isoform PDE4D).

In a further aspect there is provided a pharmaceutical composition (for example, for use as a medicament for the treatment of one of the diseases or conditions listed herein, such as COPD or asthma) comprising a compound of formula (I), or a pharmaceutically acceptable salt thereof, and at least one active ingredient selected from:
  a) a glucocorticoid receptor agonist (steroidal or non-steroidal);
  b) a selective β2 adrenoceptor agonist;
  c) an antimuscarinic agent;
  d) a p38 antagonist;
  e) a Xanthine derivative; or
  f) a PDE4 antagonist;
as defined above.

In one embodiment the compound of formula (I), or a pharmaceutically acceptable salt thereof, is administered concurrently or sequentially with one or more further active ingredients selected from those defined above. For example, the compound of formula (I), or a pharmaceutically acceptable salt thereof, may be administered concurrently or sequentially with a further pharmaceutical composition for use as a medicament for the treatment of one of the diseases or conditions listed herein, such as a respiratory tract condition (e.g. COPD or asthma). Said further pharmaceutical composition may be a medicament which the patient may already be prescribed (e.g. an existing standard of care medication), and may itself be a composition comprising one or more active ingredients selected from those defined above.

Pharmaceutical Compositions

For the above-mentioned therapeutic uses the dosage administered will vary with the compound employed, the mode of administration, the treatment desired and the disorder indicated. For example, the daily dosage of the compound of formula (I), if inhaled, may be in the range from 0.05 micrograms per kilogram body weight (μg/kg) to 100 micrograms per kilogram body weight (μg/kg). Alternatively, if the compound is administered orally, then the daily dosage of the compound of formula (I) may be in the range from 0.01 micrograms per kilogram body weight (μg/kg) to 100 milligrams per kilogram body weight (mg/kg).

The compounds of formula (I), or pharmaceutically acceptable salts thereof, may be used on their own but will generally be administered in the form of a pharmaceutical composition in which the formula (I) compound/salt (active ingredient) is in association with a pharmaceutically acceptable adjuvant(s), diluents(s) or carrier(s). Conventional procedures for the selection and preparation of suitable pharmaceutical formulations are described in, for example, "Pharmaceuticals—The Science of Dosage Form Designs", M. E. Aulton, Churchill Livingstone, $2^{nd}$ Ed. 2002.

There is also provided pharmaceutical composition(s) comprising a compound of formula (I), or a pharmaceutically acceptable salt thereof, as hereinbefore defined in association with pharmaceutically acceptable adjuvant(s), diluent(s) or carrier(s).

There is also provided a process for the preparation of a pharmaceutical composition which comprises mixing a compound of formula (I), or a pharmaceutically acceptable salt thereof, as hereinbefore defined with a pharmaceutically acceptable adjuvant(s), diluents(s) or carrier(s).

Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The pharmaceutical compositions may be administered in standard manner for the disease condition that it is desired to treat, for example by topical (such as to the lung and/or airways or to the skin), inhalation, oral, rectal or parenteral administration. For these purposes the compounds of formula (I) may be formulated by means known in the art. A suitable pharmaceutical composition is one suitable for oral administration in unit dosage form, for example a tablet or capsule which contains between 0.1 mg and 1 g of active ingredient.

Each patient may receive, for example, a dose of 0.0001 $mgkg^{-1}$ to 10 $mgkg^{-1}$, for example in the range of 0.005 $mgkg^{-1}$ to 5 $mgkg^{-1}$, of the active ingredient administered, for example, 1 to 4 times per day.

In an embodiment, there is provided a pharmaceutical composition comprising a compound of formula (I) in association with a pharmaceutically acceptable adjuvant, diluent or carrier, which is formulated for inhaled administration (including oral and nasal inhalation).

The compound of formula (I) may be administered using a suitable delivery device, for example from a dry powder inhaler, a metered dose inhaler, a nebuliser or a nasal delivery device. Such devices are well known.

Dry powder inhalers may be used to administer the compound of formula (I), alone or in combination with a pharmaceutically acceptable carrier, in the latter case either as a finely divided powder or as an ordered mixture. The dry powder inhaler may be single dose or multi-dose and may utilise a dry powder or a powder-containing capsule.

Accordingly in one embodiment, the compound of formula (I), or a pharmaceutical composition containing a compound of formula (I), is administered by means of a dry powder inhaler (DPI).

The DPI may be "passive" or breath-actuated, or "active" where the powder is dispersed by some mechanism other than the patient's inhalation, for instance, an internal supply of compressed air. At present, three types of passive dry powder inhalers are available: single-dose, multiple unit dose or multidose (reservoir) inhalers. In single-dose devices, individual doses are provided, usually in gelatine capsules, and have to be loaded into the inhaler before use, examples of which include Spinhaler® (Aventis), Rotahaler® (GlaxoSmithKline), Aeroliser™ (Novartis), Inhalator® (Boehringer) and Eclipse (Aventis) devices. Multiple unit dose inhalers contain a number of individually packaged doses, either as multiple gelatine capsules or in blisters, examples of which include Diskhaler® (GlaxoSmithKline), Diskus® (GlaxoSmithKline), Nexthaler® (Chiesi) and Aerohaler® (Boehringer) devices. In multidose devices, drug is stored in a bulk powder reservoir from which individual doses are metered, examples of which include Genuair® (AstraZeneca), Turbuhaler® (AstraZeneca), Easyhaler® (Orion), Novolizer® (ASTA Medica), Clickhaler® (Innovata Biomed), Spiromax® (Teva) and Pulvinal® (Chiesi) devices.

An inhalable pharmaceutical composition for use in a DPI can be prepared by mixing finely divided active ingredient (having an aerodynamic diameter generally equal to or less than 10 µm, such as equal to or less than 5 µm, e.g. from 1 to 5 µm) with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Suitably the particles of the active ingredient adhere to the carrier particles to form an ordered (interactive) powder mixture. The carrier particles may have a mass median diameter of from 20 to 1000 µm, more usually from 50 to 500 µm.

Alternatively, an inhalable pharmaceutical composition may be prepared by processing a finely divided powder (e.g. consisting of finely divided active ingredient and finely divided carrier particles) into spheres that break up during the inhalation procedure.

The powder mixture may then, as required, be dispensed into hard gelatine capsules, each containing the desired dose of the active ingredient. Alternatively the powder mixture may be loaded into the reservoir of a multidose inhaler for example, the Genuair®, or the Turbuhaler®.

In a further embodiment, the compound of formula (I) is administered by means of a metered dose inhaler, particularly a pressurized metered dose inhaler (pMDI). The pMDI contains the active as a suitable solution or suspension in a pressurized container. The active is delivered by actuating a valve on the pMDI device. Actuation may be manual or breath actuated. In manually actuated pMDIs the device is actuated by the user as they inhale, for example by pressing a suitable release mechanism on the pMDI device. Breath actuated pMDIs are actuated when the patient inhales through the mouthpiece of the pMDI. This can be advantageous as the actuation of the device is timed with the patients' inhalation and can result in a more consistent dosing of the active. Examples of pMDI devices include for example Rapihaler® (AstraZeneca).

An inhalable pharmaceutical composition for use in a pMDI can be prepared by dissolving or dispersing the compound of formula (I) in a suitable propellant and with or without additional excipients such as solvents (for example ethanol), surfactants, lubricants or stabilising agents. Suitable propellants include hydrocarbon, chlorofluorocarbon and hydrofluoroalkane (e.g. heptafluoroalkane) propellants, or mixtures of any such propellants. Preferred propellants are P134a and P227, each of which may be used alone or in combination with other propellants and/or surfactant and/or other excipients.

In a further embodiment, the compound of formula (I) is administered by means of a metered dose inhaler in combination with a spacer. Suitable spacers are well known and include Nebuchamber® (AstraZeneca) or Volumatic® (GlaxoSmithKline).

In a further embodiment, the compound of formula (I) is administered by means of a nebuliser. Suitable nebulisers are well known and include eFlow® (PARI GmbH).

An inhalable pharmaceutical composition for use in a nebuliser can be prepared by dispersing or dissolving the compound of formula (I) in a suitable aqueous medium. The composition may also include for example suitable pH and/or tonicity adjustment, surfactants and preservatives. For example a suitable composition for inhalation from a nebuliser comprises a compound of formula (I) dispersed in an aqueous medium (mg/g in highly purified water, e.g. Milli-Q water) comprising sodium chloride (9 mg/g); citric acid dried (0.0735 mg/g); sodium citrate (0.19 mg/g); benzalkonium chloride (0.1 mg/g), EDTA (ethylenediamine tetraacetic acid, 0.1 mg/g) and Polysorbate 80 (0.3 mg/g).

In a further embodiment, the compound of formula (I) is administered nasally as a spray from a suitable nasal delivery device, for example a spray pump or an MDI. Alternatively, the compound could be administered nasally as a powder using a suitable DPI device e.g. Rhinocort®, Turbuhaler® (AstraZeneca).

An inhalable pharmaceutical composition for use in a spray pump or MDI nasal delivery device can be prepared by dispersing or dissolving the compound of formula (I) in a suitable aqueous medium. The composition may also include for example suitable pH and/or tonicity adjustment, surfactants, preservatives, lubricants flavourings or viscosity modifiers. If required additives to enhance absorption from the nasal cavity can be included, such as a suitable bioadhesive polymer. Suitable dry powder compositions for nasal delivery are as hereinbefore described in relation to DPI delivery. However, where it is desirable to limit the penetration of the compound into the lung and keep the compound in the nasal cavity, it may be necessary to use the compound as larger particle sizes, for example with an average particle diameter greater than about 10 µm, e.g. from 10 µm to 50 µm.

Accordingly, there is also provided an inhaler device (for example a dry powder inhaler, in particular a multiple unit dose dry powder inhaler, or a pMDI inhaler) containing an inhalable pharmaceutical composition of the invention.

Preparation of Compounds

In another aspect there is provided a process for preparing a compound of the formula (I), or a pharmaceutically acceptable salt thereof, which process comprises:

a) Reaction of a compound of the formula (II) with a compound of the formula (III),

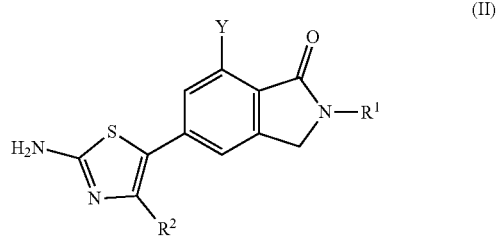

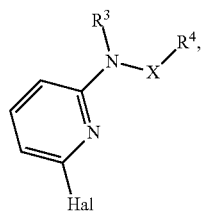

(III)

wherein R¹, R², R³, R⁴, X and Y are as defined in formula (I), Hal is halogen, and under conditions such that a displacement of the halogen of the compound of formula (III) by the amino group of the compound of formula (II) occurs, and, where desired, separating the resultant compound of formula (I) into its individual optical isomers, and where necessary converting the resultant compound of formula (I) into a pharmaceutically acceptable salt thereof and, where necessary converting the resultant compound of formula (I) into a preferred polymorph; or b) Reaction of a compound of the formula (IV) with a compound of the formula (V),

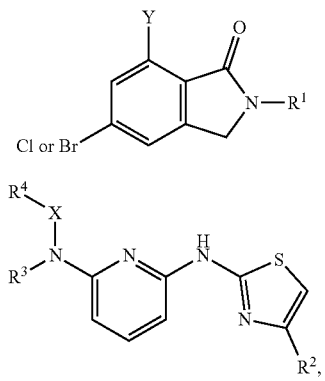

(IV)

(V)

wherein R¹, R², R³, R⁴, X and Y are as defined in formula (I) and under conditions such that a bond is formed between the carbon atom bearing the chlorine or bromine atom of formula (IV) and C-5 of the thiazole, and, where desired, separating the resultant compound of formula (I) into its individual optical isomers, and where necessary converting the resultant compound of formula (I) into a pharmaceutically acceptable salt thereof and, where necessary converting the resultant compound of formula (I) into a preferred polymorph. The compounds of formula (II) and (III) react under conditions promoting nucleophilic aromatic displacement. The reaction is typically performed in a polar aprotic solvent, such as DMF or THF, with heating, typically in a range from 60-140° C. Heating can be by conventional or microwave means and the use of pressurised systems to enable reactions to run above the boiling point of the solvent may be advantageous. The reaction may be catalysed by a transition metal, for example palladium, in the presence of suitable ligands, such as bidentate trisubstituted phosphines, for example xantphos, and a base such as an alkali metal carbonate, for example sodium carbonate. The compounds of formula (IV) and (V) react under conditions promoting the activation of aryl bromides and their reaction with activated double bonds ("Heck reaction"). The reaction is typically performed in a polar aprotic solvent, such as DMF or THF, with heating, typically in a range from 60-140° C. Heating can be by conventional or microwave means and the use of pressurised systems to enable reactions to run above the boiling point of the solvent may be advantageous. For example a catalytic amount of a transition metal such as palladium in the presence of a suitable ligand, such as a sterically hindered trialkylphosphine, for example tri t-butylphosphine, in the presence of a suitable base such as an alkali metal carbonate, for example cesium carbonate.

Compounds of formula (II) may be prepared from a compound of formula (IV) and a compound of formula (VI),

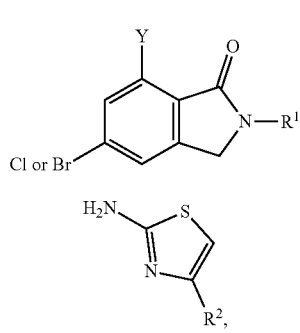

(IV)

(VI)

wherein R¹, R² and Y are as defined in formula (I) and under conditions promoting the activation of aryl bromides and their reaction with activated double bonds ("Heck reaction"). The reaction is typically performed in a polar aprotic solvent, such as DMF or THF, with heating, typically in a range from 60-140° C. Heating can be by conventional or microwave means and the use of pressurised systems to enable reactions to run above the boiling point of the solvent may be advantageous. For example a catalytic amount of a transition metal such as palladium in the presence of a suitable ligand, such as a sterically hindered trialkylphosphine, for example tri t-butylphosphine, in the presence of a suitable base such as an alkali metal carbonate, for example cesium carbonate. Compounds of formula (VI) may be optionally protected during the reaction with a compound of formula (II), for example with an acetyl or BOC group. Such protecting groups may be removed by methods known in the art, for example acid or base treatment.

Compounds of formula (II), optionally with the free amine protected, wherein Y represents SO₂R⁶ may be prepared from a compound of formula (VII),

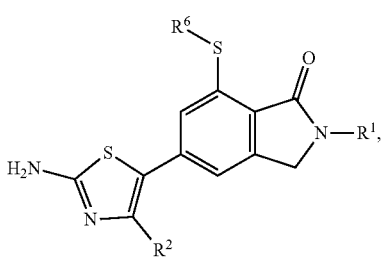

(VII)

wherein R¹, R² and R⁶ are as defined in formula (I), optionally suitably protected, for example with an acetyl or BOC group, by oxidation with a suitable agent, for example a peracid such as mCPBA in a suitable solvent, such as dichloromethane or chloroform at a temperature of typically −20-25° C. Alternatively the oxidant can be potassium peroxymonosulfate ("Oxone") in a suitable solvent such as an alcohol, for example ethanol, optionally containing water, at a temperature between ambient and reflux, for example 50° C.

Compounds for formula (IV) wherein Y represents SO$_2$R$^6$ may be prepared from a compound of formula (VIII),

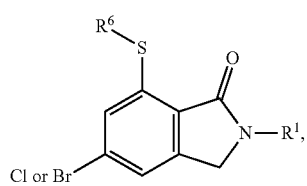

(VIII)

wherein R$^1$ and R$^6$ are as defined in formula (I), by oxidation with a suitable agent, for example a peracid such as mCPBA in a suitable solvent, such as dichloromethane or chloroform at a temperature of typically −20-25° C. Alternatively the oxidant can be potassium peroxymonosulfate ("Oxone") in a suitable solvent such as an alcohol, for example ethanol, optionally containing water, at a temperature between ambient and reflux, for example 50° C.

Compounds of formula (II), optionally with the free amine protected, wherein Y represents SO$_2$NHR$^5$ may be prepared from a compound of formula (IX), (optionally protected) and a compound of formula (X),

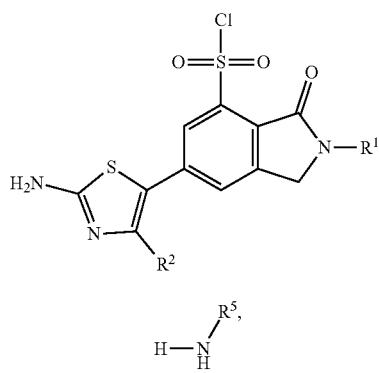

(IX)

(X)

wherein R$^1$, R$^2$ and R$^5$ are as defined in formula (I). The reaction is typically carried out in the presence of a base, which may be an excess of the compound of formula (X), or an amine base such as triethylamine or 4-dimethylaminopyridine, in a suitable solvent, such as dichloromethane or THF, at a suitable temperature, for example between 0° C. and ambient temperature.

Compounds of formula (IV), optionally with the free amine protected, wherein Y represents SO$_2$NHR$^5$ may be prepared from a compound of formula (XI), optionally protected, and a compound of formula (X),

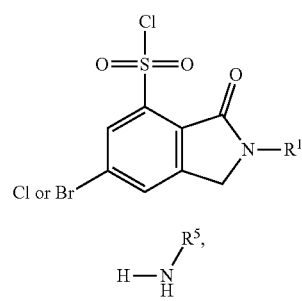

(XI)

(X)

wherein R$^1$ and R$^5$ are as defined in formula (I). The reaction is typically carried out in the presence of a base, which may be an excess of the compound of formula (X), or an amine base such as triethylamine or 4-dimethylaminopyridine, in a suitable solvent, such as dichloromethane or THF, at a suitable temperature, for example between 0° C. and ambient temperature.

A compound of formula (IX or XI) may be prepared from a compound of formula (VII or VIII), respectively, wherein R$^6$ represents benzyl, optionally suitably protected, with a suitable chlorinating and oxidising agent, for example sulfuryl chloride or 1,3-dichloro-5,5-dimethylimidazolidine-2,4-dione; the reaction can be carried out in a suitable solvent mixture, for example a mixture of water and acetonitrile containing acetic acid at a suitable temperature, for example between −5° C. and ambient temperature.

A compound of formula (VII), optionally protected, may be prepared from a compound of formula (XII), optionally protected, by reaction with a compound of formula (XIII),

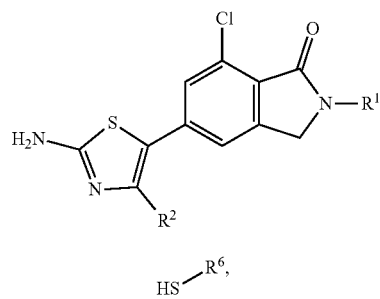

(XII)

(XIII)

wherein R$^1$, R$^2$ and R$^6$ are as defined in formula (I), in the presence a suitable base, for example a sodium alkoxide such as sodium 2-methylbutan-2-olate or sodium t-butoxide; alternatively a preformed thiolate, such as sodium methanethiolate, may be used; the reaction can be run in a suitable solvent, for example DMF or dioxan at a suitable temperature, typically between 80 and 120° C.

A compound of formula (VIII), optionally protected, may be prepared from a compound of formula (XIV) by reaction with a compound of formula (XIII),

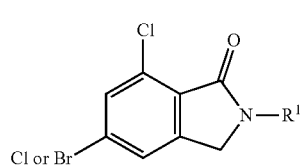

(XIV)

(XIII)

wherein $R^1$ and $R^6$ are as defined in formula (I), in the presence a suitable base, for example a sodium alkoxide such as sodium 2-methylbutan-2-olate or sodium t-butoxide; alternatively a preformed thiolate, such as sodium methanethiolate, may be used; the reaction can be run in a suitable solvent, for example DMF or dioxan at a suitable temperature, typically between 80 and 120° C.

Compounds of formula (XII) may be prepared from a compound of formula (XIV) and a compound of formula (VI) under conditions promoting the activation of aryl bromides and their reaction with activated double bonds ("Heck reaction"). The reaction is typically performed in a polar aprotic solvent, such as DMF or THF, with heating, typically in a range from 60-140° C. Heating can be by conventional or microwave means and the use of pressurised systems to enable reactions to run above the boiling point of the solvent may be advantageous. For example a catalytic amount of a transition metal such as palladium in the presence of a suitable ligand, such as a sterically hindered trialkylphosphine, for example tri t-butylphosphine, in the presence of a suitable base such as an alkali metal carbonate, for example cesium carbonate. Compounds of formula (VI) may be optionally protected during the reaction with a compound of formula (II), for example with an acetyl or BOC group.

A compound of formula (V) may be prepared by reaction of a compound of formula (III) with a compound of formula (VI) and under conditions such that a displacement of the halogen of the compound of formula (III) by the amino group of the compound of formula (V) occurs; the reaction is typically performed in a polar aprotic solvent, such as DMF or THF, with heating, typically in a range from 60-140° C. Heating can be by conventional or microwave means and the use of pressurised systems to enable reactions to run above the boiling point of the solvent may be advantageous. The reaction may be catalysed by a transition metal, for example palladium, in the presence of suitable ligands, such as bidentate trisubstituted phosphines, for example xantphos, and a base such as an alkali metal carbonate, for example sodium carbonate.

A compound of formula (III) may be prepared from a compound of formula (XV) and a compound of formula (XVI),

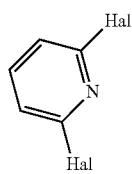

(XV)

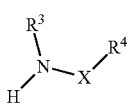

(XVI)

wherein X, $R^3$ and $R^4$ are as defined in formula (I) and Hal is a halogen, under conditions promoting nucleophilic aromatic displacement. The reaction is typically performed in a polar aprotic solvent, such as dioxan, with heating, typically in a range from 60-100° C. Heating can be by conventional or microwave means and the use of pressurised systems to enable reactions to run above the boiling point of the solvent may be advantageous. The reaction may be catalysed by a transition metal, for example palladium, in the presence of suitable ligands, such as bidentate trisubstituted phosphines, for example xantphos, and a base such as an alkali metal carbonate, for example cesium carbonate.

Alternatively a compound of formula (III) may be prepared from a compound of formula (XVII) and a compound of formula (XVIII),

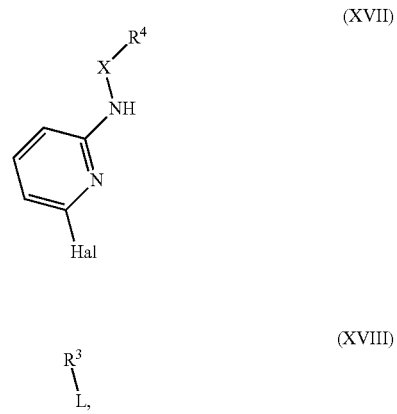

wherein X, $R^3$ and $R^4$ are as defined in formula (I) and L represents a leaving group, such as a halogen or a sulfonate ester, in the presence of a base, such as sodium hydride, in a suitable solvent, such as THF at a suitable temperature, for example 0° C. In cases where $R^3$ and $R^4$ are connected such that the reaction is intramolecular then milder conditions may be used and the base may be weaker, for example pyridine. In such cases acetonitrile is a suitable solvent and the reaction may be run using a mild temperature, for example ambient conditions.

Alternatively a compound of formula (III) may be prepared by reaction of a compound of formula (XIX) with a compound of formula (XX),

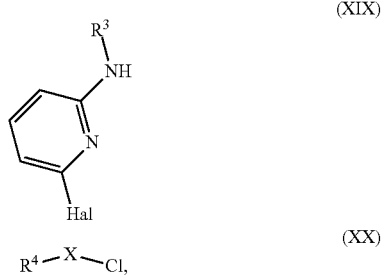

wherein X, $R^3$ and $R^4$ are as defined in formula (I), in the presence of a base, such as pyridine, in a suitable solvent, such as dichloromethane, at a suitable temperature, for example between 0° C. and ambient temperature.

A compound of formula (XVII) may be prepared by reaction of a compound of formula (XXI) with a compound of formula (XX),

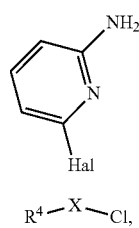

(XXI)

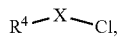

(XX)

wherein X and R⁴ are as defined in formula (I), in the presence of a base, such as pyridine, in a suitable solvent, such as dichloromethane, at a suitable temperature, for example between 0° C. and ambient temperature.

It will be appreciated by those skilled in the art that in the processes certain functional groups such as hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Synthesis', 5$^{th}$ Ed, T. W. Greene and P. G. M. Wuts, Wiley (2014) and 'Protecting Groups', 3$^{rd}$ Ed P. J. Kocienski, Georg Thieme Verlag (2005).

The skilled person will recognize that at any stage of the preparation of the compounds of formula (I), mixtures of isomers (e.g. racemates) of compounds may be utilized. At any stage of the preparation, a single stereoisomer may be obtained by isolating it from a mixture of isomers (e.g., a racemate) using, for example, chiral chromatographic separation.

A further embodiment encompasses pharmaceutically acceptable salts of the compounds of formula (I).

A salt of a compound of formula (I) may be advantageous due to one or more of its chemical or physical properties, such as stability in differing temperatures and humidities, or a desirable solubility in $H_2O$, oil, or other solvent. In some instances, a salt may be used to aid in the isolation or purification of the compound. In some embodiments (particularly where the salt is intended for administration to an animal, e.g. a human, or is a reagent for use in making a compound or salt intended for administration to an animal), the salt is pharmaceutically acceptable.

Where the compound is sufficiently acidic, pharmaceutically acceptable salts include, but are not limited to, an alkali metal salt, e.g. Na or K, an alkali earth metal salt, e.g. Ca or Mg, or an organic amine salt. Where the compound is sufficiently basic, pharmaceutically acceptable salts include, but are not limited to, inorganic or organic acid addition salts.

There may be more than one cation or anion depending on the number of charged functions and the valency of the cations or anions.

For reviews on suitable salts, see Berge et al., J. Pharm. Sci., 1977, 66, 1-19 or "Handbook of Pharmaceutical Salts: Properties, selection and use", P. H. Stahl, P. G. Vermuth, IUPAC, Wiley-VCH, 2002.

In a salt proton transfer occurs between the compound of formula (I) and the counter ion of the salt. However, in some cases proton transfer may not be complete and the solid is not therefore a true salt. In such cases the compound of formula (I) and the "co-former" molecules in the solid primarily interact through non-ionic forces such as hydrogen bonding. It is accepted that the proton transfer is in fact a continuum, and can change with temperature, and therefore the point at which a salt is better described as a co-crystal can be somewhat subjective.

Where an acid or base co-former is a solid at rt and there is no or only partial proton transfer between the compound of formula (I) and such an acid or base co-former, a co-crystal of the co-former and compound of formula (I) may result rather than a salt. All such co-crystal forms of the compound of formula (I) are encompassed.

The compounds of formula (I) may form mixtures of its salt and co-crystal forms. It is also to be understood that salt/co-crystal mixtures of the compound of formula (I) are encompassed Salts and co-crystals may be characterized using well known techniques, for example X-ray powder diffraction, single crystal X-ray diffraction (for example to evaluate proton position, bond lengths or bond angles), solid state NMR, (to evaluate for example C, N or P chemical shifts) or spectroscopic techniques (to measure for example, O—H, N—H or COOH signals and IR peak shifts resulting from hydrogen bonding).

It is also to be understood that certain compounds of formula (I) may exist in solvated form, e.g. hydrates, including solvates of a pharmaceutically acceptable salt of a compound of formula (I).

In a further embodiment, certain compounds of formula (I) may exist as racemates and racemic mixtures, single enantiomers, individual diastereomers and diastereomeric mixtures. It is to be understood that all such isomeric forms are encompassed. Certain compounds of formula (I) may also contain linkages (e.g. carbon-carbon bonds, carbon-nitrogen bonds such as amide bonds) wherein bond rotation is restricted about that particular linkage, e.g. restriction resulting from the presence of a ring bond or double bond. Accordingly, it is to be understood that all such isomers are encompassed. Certain compound of formula (I) may also contain multiple tautomeric forms. It is to be understood that all such tautomeric forms are encompassed. Stereoisomers may be separated using conventional techniques, e.g. chromatography or fractional crystallization, or the stereoisomers may be made by stereoselective synthesis.

In a further embodiment, the compounds of formula (I) encompass any isotopically-labeled derivatives of a compound of formula (I). Such a derivative is a derivative of a compound of formula (I) wherein one or more atoms are replaced by an atom having an atomic mass or mass number different from the atomic mass or mass number typically found in nature. Examples of isotopes that may be incorporated include $^2H$ (also written as "D" for deuterium).

In a further embodiment, the compounds of formula (I) may be administered in the form of a prodrug which is broken down in the human or animal body to give a compound of the formula (I). Examples of prodrugs include in vivo hydrolysable esters of a compound of the formula (I).

An in vivo hydrolysable (or cleavable) ester of a compound of the formula (I) that contains a carboxy or a hydroxy group is, for example, a pharmaceutically acceptable ester which is hydrolyzed in the human or animal body to produce the parent acid or alcohol. For examples of ester prodrugs derivatives, see: Curr. Drug. Metab. 2003, 4, 461.

Various other forms of prodrugs are known in the art. For examples of prodrug derivatives, see: Nature Reviews Drug Discovery 2008, 7, 255 and references cited therein.

EXAMPLES

The disclosure will now be further explained by reference to the following non limiting examples.

(i) Unless stated otherwise, $^1$H NMR spectra were recorded on Bruker Avance, Avance II or Avance III spectrometers operating at a field strength of 300, 400, 500 or 600 MHz. Either the central peaks of chloroform-d (CDCl$_3$; $\delta_H$ 7.27 ppm; $\delta_C$ 77.2 ppm), dimethylsulfoxide-d$_6$ (DMSO-d$_6$; $\delta_H$ 2.50 ppm; $\delta_C$ 39.5 ppm) or methanol-d$_4$ (CD$_3$OD; $\delta_H$ 3.31 ppm; $\delta_C$ 49.1 ppm) were used as internal references.

(ii) LCMS was run in two set ups: 1) BEH C18 column (1.7 µm 2.1×50 mm) in combination with a gradient (2-95% B in 5 min) of aqueous 46 mM NH$_4$HCO$_3$/NH$_3$ buffer at pH 10 (A) and MeCN (B) at a flow rate of 1.0 mL/min or in combination with a gradient (5-95% B in 2 min) of water and TFA (0.05%) (A) and MeCN and TFA (0.05%) at a flow rate of 1.0 mL/min (B).

(iii) Preparative HPLC was performed with a Waters FractionLynx system with integrated MS detection and equipped with Prep C18 OBD 5 µm 19×150 mm columns from X-Bridge or to Sunfire. Alternatively Gilson GX-281 with integrated UV detection was used, equipped with either Kromasil C8 10 µm, 20×250 ID or 50×250 ID mm. As eluent (acidic) gradients of water/MeCN/acetic acid (95/5/0.1) or water/0.05% TFA (A) and MeCN/0.05% TFA (B) or (basic) MeCN or MeOH (A) and 0.03% NH$_3$ in water or 0.03% NH$_4$HCO$_3$ (B) were applied.

(iv) Preparative SCF was performed with a Waters Prep100 SCF system with integrated MS detection, equipped with Waters Viridis 2-EP or Phenomenex Luna Hilic, 30×250 mm, 5 m. As eluent gradients of CO$_2$ (100 g/min, 120 bar, 40° C.) (A) and MeOH/NH$_3$ (20 mM) or MeOH (5% FA) or MeOH (B) were applied.

(v) The title and sub-title compounds of the examples and preparations were named using the IUPAC name program ACD/Name 2014 from Acdlabs.

(vi) Unless stated otherwise, starting materials were commercially available, and all solvents and commercial reagents were of laboratory grade and used as received. Unless stated otherwise, operations were carried out at ambient temperature, i.e. in the range between 17-28° C. and, where appropriate, under an atmosphere of an inert gas such as nitrogen.

(vii) The X-ray diffraction analysis was performed according to standard methods, which can be found in e.g. Kitaigorodsky, A. I. (1973), Molecular Crystals and Molecules, Academic Press, New York; Bunn, C. W. (1948), Chemical Crystallography, Clarendon Press, London; or Klug, H. P. & Alexander, L. E. (1974), X-ray Diffraction Procedures, John Wiley & Sons, New York. Samples were mounted on single silicon crystal (SSC) wafer mounts and powder X-ray diffraction was recorded with a PANalytical X'Pert PRO (reflection geometry, wavelength of X-rays 1.5418 Å nickel-filtered Cu radiation, Voltage 45 kV, filament emission 40 mA). Automatic variable divergence and anti scatter slits were used and the samples were rotated during measurement. Samples were scanned from 2-50 °2Theta or 2-40 °2Theta using a 0.013° step width and between 44 and 233 seconds count time using a PIXCEL detector (active length 3.35 °2Theta).

It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensities of peaks may vary according to the orientation of the sample under test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a power diffraction pattern substantially identical to those disclosed herein fall within the scope of the present disclosure (for further information see Jenkins, R & Snyder, R. L. 'Introduction to X-Ray Powder Diffractometry' John Wiley & Sons, 1996). Generally, a measurement error of a diffraction angle in an X-ray powder diffractogram may be approximately plus or minus 0.1° 2-theta, and such a degree of a measurement error should be taken into account when considering the X-ray powder diffraction data. Furthermore, it should be understood that intensities might fluctuate depending on experimental conditions and sample preparation (e.g. preferred orientation). The following definitions have been used for the relative intensity (%): 81-100%, vs (very strong); 41-80%, str (strong); 21-40%, med (medium); 10-20%, w (weak); 1-9%, vw (very weak).

The following abbreviations are used:

| | |
|---|---|
| CV | Column volumes |
| DCM | Dichloromethane |
| DMF | N,N-Dimethylformamide |
| DMSO | Dimethyl sulfoxide |
| EtOAc | Ethyl acetate |
| eq | Equivalents |
| FA | Formic acid |
| g | Gram(s) |
| h | Hour(s) |
| HPLC | High performance liquid chromatography |
| L | Liter(s) |
| LC | Liquid chromatography |
| m-CPBA | 3-Chloroperoxybenzoic acid |
| MeCN | Acetonitrile |
| MeOH | Methanol |
| min | Minute(s) |
| mL | Milliliter(s) |
| nm | Nanometer |
| rt | Room temperature |
| TBME | Tertiary butl methyl ether |
| TFA | Trifluoroacetic acid |
| $t_R$ | Retention time |
| Xantphos | (9,9-dimethyl-9H-xanthene-4,5-diyl)bis(diphenylphosphane) |
| 2$^{nd}$ Generation XantPhos precatalyst | See J. Am. Chem. Soc., 2010, 132 (40), pp 14073-14075 for a prep of a related precatalyst; CAS 1375325-77-1 Palladium, [2'-(amino-κN)[1,1'-biphenyl]-2-yl-κC]chloro[[5-(diphenylphosphino)-9,9-dimethyl-9H-xanthen-4-yl]diphenylphosphine-κP]- |
| 3$^{rd}$ Generation XantPhos precatalyst | Chem. Sci., 2013, 4, 916-920; CAS 1445085-97-1 Palladium, [2'-(amino-κN)[1,1'-biphenyl]-2-yl-κC][[5-(diphenylphosphino)-9,9-dimethyl-9H-xanthen-4-yl]diphenylphosphine-κP](methanesulfonato-κO)- |

The following HPLC conditions were used for analysis of intermediates and final compounds:
Method FA
Column: Shimadzu shim-pack XR-ODS 2.2 µm 3.0×50 mm
Mobile Phase: A: Water/0.1% FA; B: MeCN/0.1% FA
Gradient: 0.01 min 10% B, 0.01-1.20 min 10-95% B, 1.20-2.20 min 95% B, 2.20-2.3 min 95-10% B
Total Flow: 1.0000 mL/min
Temperature: 40° C.
Method FA System 2
Column: Accucore C18 2.7 µm 2.1×50 mm
Mobile phase A: Water/0.1% FA; B: MeCN/0.1% FA Gradient: 10%-100% B, 0.01-2.00 min, 100% B 2.00-2.70 min, 100%-10% B 2.70-2.80 min.
Method TFA
Column Name: Waters corporation CORTECS C18 2.7 μm 2.1×50 mm
Mobile Phase: A: Water/0.05% TFA; B: MeCN/0.05% TFA
Gradient: 0.01 min 5% B, 0.01-1.10 min 5-100% B, 1.10-1.60 min 100% B, 1.60-1.70 min 100-5% B
Total Flow: 0.700 mL/min
Temperature: 45° C.
Method TFA System 2
Column: Shimadzu shim-pack XR-ODS 2.2 μm 3.0×50 mm
Mobile phase: A: Water/0.05% TFA; B: MeCN/0.05% TFA
Gradient: 10-95% B, 0.01-2.20 min, 95% B 2.20-3.2 min 95% B, 3.2-3.3 min 95%-5% B
Method Base:
Column Name: Agilent Poroshell HPH-C18, 2.7 μm 3.0×50 mm
Mobile Phase: A: Water/5 mM NH$_4$HCO$_3$; B: MeCN
Gradient: 0.01 min 10% B, 0.01-1.10 min 10-95% B, 1.10-1.60 min 95% B, 1.60-1.70 min 95-10% B
Total Flow: 1.200 mL/min
Temperature: 40° C.
Method Acid:
Column Name: Shimadzu shim-pack XR-ODS 2.2 μm 3.0×50 mm
Mobile Phase: A: Water/0.05% TFA; B: MeCN/0.05% TFA
Gradient: 0.01 min 10% B, 0.01-1.20 min 5-95% B, 1.20-2.20 min 95% B, 2.20-2.30 min 95-5% B
Temperature: 40° C.
Method pH3:
Column Name: Waters Acquity HSS C18, 1.8 μm, 2.1×50 mm
Mobile Phase: A: Water/10 mM formic acid+1 mM ammonia; B: 95% MeCN, 5% water (v/v) 10 mM formic acid+1 mM ammonia
Gradient: 0.01 min 10% B, 0.20-3.70 min 10-99% B, 3.70-3.80 min 99% B, 3.80-3.81 min 99-10% B.
Total Flow: 1.0 mL/min
Temperature: 60° C.
Method pH10
Column Name: Waters Acquity BEH C18, 1.7 μm, 2.1×50 mm
Mobile Phase: A: Water/6.5 mM ammonium hydrogen carbonate+40 mM ammonia; B: 95% MeCN, 5% (v/v) water/6.5 mM ammonium hydrogen carbonate+40 mM ammonia
Gradient: 0.01 min 10% B, 0.20-1.70 min 10-99% B, 1.70-1.80 min 99% B, 1.80-1.81 min 99-10% B.
Total Flow: 1.0 mL/min
Temperature: 60° C.
Method pH10 (long)
Column Name: Waters Acquity BEH C18, 1.7 μm, 2.1×50 mm
Mobile Phase: A: Water/6.5 mM ammonium hydrogen carbonate+40 mM ammonia; B: 95% MeCN, 5% (v/v) water/6.5 mM ammonium hydrogen carbonate+40 mM ammonia
Gradient: 0.01 min 10% B, 0.20-3.70 min 10-99% B, 3.70-3.80 min 99% B, 3.80-3.81 min 99-10% B.
Total Flow: 1.0 mL/min
Temperature: 60° C.
Method CAL
Column Name: Acquity BEH C18 1.7 μm, 30×4.6 mm
Mobile Phase: A: water; B: MeCN C 1% TFA in water
Gradient (3% C throughout): 0.00 min 5% B, 0.00-5.20 min 5-90% B, 5.20-5.70 min 90% B, 5.70-5.80 min 90-5% B.
Total Flow: 2.0 mL/min
Temperature: 40° C.

PREPARATION OF INTERMEDIATES

Intermediate 1 (Method A)

5-Bromo-7-chloro-2-[(1S)-1-cyclopropylethyl]-2,3-dihydro-1H-isoindol-1-one (S)-1-Cyclopropylethanamine (2.428 mL, 22.78 mmol) was added to methyl 4-bromo-2-(bromomethyl)-6-chlorobenzoate (7.8 g, 22.78 mmol) in MeCN (80 mL). Boric acid (1.409 g, 22.78 mmol) was added in one portion as a dry solid, followed by potassium carbonate (6.30 g, 45.56 mmol) which was added portionwise over 2 min. The mixture was allowed to stir at rt overnight. The inorganics were filtered off and washed with MeCN. The combined MeCN filtrates was concentrated to yield 8.3 g of a brown oil. The residue was purified by automated flash chromatography on a Biotage® KP-SIL 340 g column using a gradient from 5 to 30% of EtOAc in heptane over 12 CV. To give the title compound as a pink solid (2.4 g, 33%).

$^1$H-NMR (500 MHz, CDCl$_3$) δ 0.33-0.51 (m, 3H), 0.57-0.69 (m, 1H), 0.94-1.05 (m, 1H), 1.34 (d, 3H), 3.67-3.81 (m, 1H), 4.37 (d, 1H), 4.48 (d, 1H), 7.5-7.55 (m, 1H), 7.58 (s, 1H).

The following intermediates 2-5 were prepared by Method A using the appropriate amines:

Intermediate 2

5-Bromo-7-chloro-2-[(2S)-3,3-dimethylbutan-2-yl]-2,3-dihydro-1H-isoindol-1-one $^1$H NMR (500 MHz, CDCl$_3$) δ 1.00 (s, 9H), 1.24 (d, 3H), 4.35 (t, 1H), 4.39 (d, 2H), 7.44-7.52 (m, 1H), 7.52-7.61 (m, 1H).

Intermediate 3

5-Bromo-2-tert-butyl-7-chloro-2,3-dihydro-1H-isoindol-1-one $^1$H NMR (300 MHz, DMSO-d$_6$) δ 1.46 (s, 5H), 4.51-4.60 (m, 1H), 7.65-7.82 (m, 1H).
m/z (ES+) [M+H]$^+$=303.9, acid, HPLC $t_R$=1.63.

Intermediate 4

5-Bromo-7-chloro-2-[(2S)-1,1,1-trifluoropropan-2-yl]-2,3-dihydro-1H-isoindol-1-one m/z (ES+), [M+H]$^+$=344; acid, HPLC $t_R$=1.15 min.

Intermediate 5

5-Bromo-2-[(2S)-butan-2-yl]-7-chloro-2,3-dihydro-1H-isoindol-1-one $^1$H NMR (500 MHz, CDCl$_3$) δ 0.89 (t, 3H), 1.26 (d, 3H), 1.62 (p, 2H), 4.20 (d, 1H), 4.27 (d, 1H), 4.40 (h, 1H), 7.49 (d, 1H), 7.57 (d, 1H).
[M+H]$^+$ 302/304/306; Method pH10OHPLC $t_R$ 1.26.

Intermediate 6 (Method B)

N-(5-{7-Chloro-2-[(1S)-1-cyclopropylethyl]-1-oxo-2,3-dihydro-1H-isoindol-5-yl}-4-methyl-1,3-thiazol-2-yl)acetamide Cs$_2$CO$_3$ (37.3 g, 114.43 mmol) was added to 5-bromo-7-chloro-2-[(1S)-1-cyclopropylethyl]-2,3-dihydro-1H-isoindol-1-one (Intermediate 1, 18 g, 57.21 mmol), N-(4-methylthiazol-2-yl)acetamide N-(4-methyl-1,3-thiazol-2-yl) acetamide (10.72 g, 68.66 mmol), tri-tert-butylphosphonium tetrafluoroborate (3.32 g, 11.44 mmol) and Pd(OAc)$_2$ (1.285 g, 5.72 mmol) in DMF (300 mL). The resulting mixture was stirred at 100° C. for 2 h and then cooled to rt. The mixture was filtered through a Celite pad. The solvent was removed under reduced pressure. The crude product was purified by flash silica chromatography, elution gradient 0 to 25% MeOH in DCM. Pure fractions were evaporated to dryness to afford the title compound (14.0 g, 63%) as a yellow solid.

$^1$H NMR (300 MHz, Methanol-d$_4$) δ 0.28-0.57 (m, 3H), 0.62-0.79 (m, 1H), 1.04-1.24 (m, 1H), 1.40 (d, 3H), 2.24 (s, 2H), 2.43 (s, 2H), 3.60-3.73 (m, 1H), 4.54-4.74 (m, 2H), 7.52 (s, 1H), 7.62 (s, 1H).

m/z (ES+) [M+H]$^+$=390; acid, HPLC t$_R$=2.031 min.

The following intermediates 7-9 were prepared by Method B using the appropriate precursor:

Intermediate 7

N-(5-{7-Chloro-2-[(2S)-3,3-dimethylbutan-2-yl]-1-oxo-2,3-dihydro-1H-isoindol-5-yl}-4-methyl-1,3-thiazol-2-yl)acetamide $^1$H NMR (500 MHz, DMSO-d$_6$) δ 0.95 (s, 9H), 1.21 (d, 3H), 2.16 (s, 3H), 2.40 (s, 3H), 4.17 (q, 1H), 4.54 (s, 2H), 7.50 (s, 1H), 7.61 (s, 1H), 12.23 (s, 1H).

m/z (ES+), [M+H]$^+$=406.2; acid, HPLC t$_R$=1.27 min.

Intermediate 8

N-[5-(2-tert-Butyl-7-chloro-1-oxo-2,3-dihydro-1H-isoindol-5-yl)-4-methyl-1,3-thiazol-2-yl]acetamide $^1$H NMR (500 MHz, DMSO-d$_6$) δ 1.24 (d, 1H), 1.49 (d, 10H), 2.15 (s, 3H), 2.38 (d, 3H), 4.60 (d, 2H), 7.47 (d, 1H), 7.59 (d, 1H), 12.23 (s, 1H).

m/z (ES+), [M+H]$^+$=390; FA System 2, HPLC t$_R$=1.091 min.

Intermediate 9

N-(5-{7-Chloro-1-oxo-2-[(2S)-1,1,1-trifluoropropan-2-yl]-2,3-dihydro-1H-isoindol-5-yl}-4-methyl-1,3-thiazol-2-yl)acetamide $^1$H NMR (500 MHz, DMSO-d$_6$) δ 1.48 (d, 3H), 2.16 (s, 3H), 2.41 (s, 3H), 4.47 (d, 1H), 4.67 (d, 1H), 5.04 (p, 1H), 7.57 (s, 1H), 7.68 (s, 1H), 12.24 (s, 1H).

m/z (ES+), [M+H]$^+$=418; acid, HPLC t$_R$=1.18 min.

Intermediate 10 (Method C)

N-(5-{7-(Benzylsulfanyl)-2-[(1S)-1-cyclopropylethyl]-1-oxo-2,3-dihydro-1H-isoindol-5-yl}-4-methyl-1,3-thiazol-2-yl)acetamide In a 50 mL round-bottomed flask was added N-(5-{7-chloro-2-[(1S)-1-cyclopropylethyl]-1-oxo-2,3-dihydro-1H-isoindol-5-yl}-4-methyl-1,3-thiazol-2-yl)acetamide (Intermediate 6, 20 g, 51.30 mmol), phenylmethanethiol (12.74 g, 102.59 mmol), and sodium 2-methylbutan-2-olate (11.30 g, 102.59 mmol) in DMF (500 mL) to give an orange suspension. The reaction mixture was stirred for a further 2 h at 110° C. The reaction mixture was filtered through celite. The solvent was removed under reduced pressure. The crude product was purified by flash silica chromatography, elution gradient 0 to 25% EtOAc in DCM. Pure fractions were evaporated to dryness to afford the title compound (18.00 g) as a yellow solid.

m/z (ES+), [M+H]$^+$=478; acid, HPLC t$_R$=1.177 min.

The following intermediates 11-13 were prepared by Method C using the appropriate precursor:

Intermediate 11

N-(5-{7-(Benzylsulfanyl)-2-[(2S)-3,3-dimethylbutan-2-yl]-1-oxo-2,3-dihydro-1H-isoindol-5-yl}-4-methyl-1,3-thiazol-2-yl)acetamide $^1$H NMR (500 MHz, CDCl$_3$) δ 1.01 (s, 9H), 1.25 (d, 3H), 2.22 (s, 3H), 2.27 (s, 3H), 4.26 (s, 2H), 4.35 (t, 1H), 4.44 (d, 2H), 7.16 (s, 1H), 7.20 (s, 1H), 7.24 (dd, 1H), 7.31 (t, 2H), 7.44-7.49 (m, 2H).

m/z (ES+), [M+H]$^+$=494.4; acid, HPLC t$_R$=2.47 min.

Intermediate 12

N-{5-[7-(Benzylsulfanyl)-2-tert-butyl-1-oxo-2,3-dihydro-1H-isoindol-5-yl]-4-methyl-1,3-thiazol-2-yl}acetamide $^1$H NMR (300 MHz, DMSO-d$_6$) δ 0.73-0.94 (m, 4H), 0.97-1.20 (m, 3H), 1.26 (t, 2H), 1.34-1.57 (m, 20H), 2.15 (s, 6H), 2.23 (s, 5H), 2.38 (d, 1H), 4.32 (s, 4H), 4.55 (s, 4H), 7.17-7.41 (m, 9H), 7.43-7.53 (m, 4H), 12.18 (d, 2H).

m/z (ES+), [M+H]$^+$=466; acid, HPLC t$_R$=1.58 min.

Intermediate 13

N-(5-{7-(Benzylsulfanyl)-1-oxo-2-[(2S)-1,1,1-trifluoropropan-2-yl]-2,3-dihydro-1H-isoindol-5-yl}-4-methyl-1,3-thiazol-2-yl)acetamide $^1$H NMR (500 MHz, DMSO-d$_6$) δ 1.46 (d, 3H), 2.16 (s, 3H), 2.25 (s, 3H), 4.27-4.5 (m, 3H), 4.63 (d, 1H), 4.98 (p, 1H), 7.21-7.42 (m, 5H), 7.49 (d, 2H), 12.18 (s, 1H).

m/z (ES+), [M+H]$^+$=506.1; acid, HPLC t$_R$=1.35 min.

Intermediate 14 (Method D)

6-[2-(Acetylamino)-4-methyl-1,3-thiazol-5-yl]-2-[(1S)-1-cyclopropylethyl]-3-oxo-2,3-dihydro-1H-isoindole-4-sulfonyl chloride Sulfuryl chloride 8.48 g, 62.81 mmol) was added portionwise to N-(5-{7-(benzylsulfanyl)-2-[(1S)-1-cyclopropylethyl]-1-oxo-2,3-dihydro-1H-isoindol-5-yl}-4-methyl-1,3-thiazol-2-yl)acetamide (Intermediate 10, 10 g, 20.94 mmol) in acetic acid (60 mL), MeCN (400 mL), and water (4.0 mL) at 0° C. The resulting mixture was stirred at 5° C. for 1 h. The solvent was removed under reduced pressure. The reaction mixture was diluted with DCM (500 mL) and washed sequentially with saturated NaHCO$_3$ (100 mL) and saturated brine (200 mL). The organic layer was dried over Na$_2$SO$_4$, filtered and evaporated. The residue was suspended in diethylether and the solid was collected by filtration. The solid was dried under vacuum to afford the title compound (8.00 g).

m/z (ES+), [M+H]$^+$=454; acid, HPLC t$_R$=1.54 min.

The following intermediates 15-17 were prepared by Method D using the appropriate precursor:

Intermediate 15

6-[2-(Acetylamino)-4-methyl-1,3-thiazol-5-yl]-2-[(2S)-3,3-dimethylbutan-2-yl]-3-oxo-2,3-dihydro-1H-isoindole-4-sulfonyl chloride m/z (ES+), [M+H]$^+$=470.2; acid, HPLC t$_R$=1.31 min.

Intermediate 16

6-[2-(Acetylamino)-4-methyl-1,3-thiazol-5-yl]-2-tert-butyl-3-oxo-2,3-dihydro-1H-isoindole-4-sulfonyl chloride m/z (ES+), [M+H]$^+$=442.0; acid, HPLC t$_R$=1.478 min.

Intermediate 17

6-[2-(Acetylamino)-4-methyl-1,3-thiazol-5-yl]-3-oxo-2-[(2S)-1,1,1-trifluoropropan-2-yl]-2,3-dihydro-1H-isoindole-4-sulfonyl chloride $^1$H NMR (500 MHz, CDCl$_3$) δ 1.55 (d, 3H), 2.32 (s, 3H), 2.48 (s, 3H), 4.45 (d, 1H), 4.60 (d, 2H), 5.18 (dq, 1H), 7.76-7.9 (m, 1H), 8.24 (d, 1H).

m/z (ES+), [M+H]$^+$=482.0; acid, HPLC t$_R$=1.20 min.

Intermediate 18 (Method E)

N-(5-{2-[(1S)-1-Cyclopropylethyl]-7-(methylsulfamoyl)-1-oxo-2,3-dihydro-1H-isoindol-5-yl}-4-methyl-1,3-thiazol-2-yl)acetamide Methanamine (2M in THF, 22.0 mL, 44.0 mmol) was added dropwise to 6-[2-(acetylamino)-4-methyl-1,3-thiazol-5-yl]-2-[(1S)-1-cyclopropylethyl]-3-oxo-2,3-dihydro-1H-isoindole-4-sulfonyl chloride (Intermediate 14, 2 g, 4.41 mmol), in DCM (40 mL) at 25° C. over a period of 30 min under nitrogen. The resulting mixture was stirred at 25° C. for 12 h. The solvent was removed under reduced pressure. The crude product was purified by flash silica chromatography, elution gradient 30 to 50% EtOAc in petroleum ether. Pure fractions were evaporated to dryness to afford the title compound (1.80 g) as a yellow solid.

$^1$H NMR (400 MHz, DMSO-d$_6$) δ 0.22-0.34 (m, 1H), 0.44 (qdd, 2H), 0.61 (tdd, 1H), 1.17 (dtt, 1H), 1.33 (d, 3H), 2.18 (s, 3H), 2.45 (s, 3H), 2.53 (s, 2H), 3.66 (dq, 1H), 4.75 (s, 2H), 5.67 (s, 1H), 7.59 (q, 1H), 7.88 (d, 1H), 8.02 (d, 1H), 12.31 (s, 1H).

m/z (ES+), [M+H]$^+$=449; acid, HPLC t$_R$=0.867 min.

The following intermediates 19-27 were prepared by Method E using the appropriate sulfonyl chloride and amine:

Intermediate 19

N-(5-{2-[(2S)-3,3-Dimethylbutan-2-yl]-7-(methylsulfamoyl)-1-oxo-2,3-dihydro-1H-isoindol-5-yl}-4-methyl-1,3-thiazol-2-yl)acetamide $^1$H NMR (600 MHz, DMSO-d$_6$) δ 0.96 (s, 9H), 1.26 (d, 3H), 2.17 (s, 3H), 2.44 (s, 3H), 4.22 (q, 1H), 4.71 (s, 2H), 7.60 (q, 1H), 7.86 (d, 1H), 7.97 (d, 1H), 12.30 (s, 1H). (3H obscured). m/z (ES+), [M+H]$^+$=465.3; acid, HPLC t$_R$=1.24 min.

Intermediate 20

N-{5-[2-tert-Butyl-7-(methylsulfamoyl)-1-oxo-2,3-dihydro-1H-isoindol-5-yl]-4-methyl-1,3-thiazol-2-yl}acetamide $^1$H NMR (300 MHz, DMSO-d$_6$) δ 1.54 (s, 9H), 2.19 (s, 3H), 2.44 (s, 3H), 4.79 (s, 2H), 7.61 (q, 1H), 7.86 (d, 1H), 7.99 (s, 1H), 12.30 (s, 1H). (3H obscured).

m/z (ES+), [M+H]$^+$=437; acid, HPLC t$_R$=0.86 min.

Intermediate 21

N-(4-Methyl-5-{7-(methylsulfamoyl)-1-oxo-2-[(2S)-1,1,1-trifluoropropan-2-yl]-2,3-dihydro-1H-isoindol-5-yl}-1,3-thiazol-2-yl)acetamide $^1$H NMR (600 MHz, DMSO-d$_6$) δ 1.52 (d, 3H), 2.17 (s, 3H), 2.45 (s, 3H), 4.62 (d, 1H), 4.82 (d, 1H), 5.08-5.13 (m, 1H), 7.17 (q, 1H), 7.90 (d, 1H), 8.03 (d, 1H), 12.33 (s, 1H). (3H obscured).

m/z (ES+), [M+H]$^+$=477; acid, HPLC t$_R$=1.11 min.

Intermediate 22

N-(5-{2-[(1S)-1-Cyclopropylethyl]-7-(ethylsulfamoyl)-1-oxo-2,3-dihydro-1H-isoindol-5-yl}-4-methyl-1,3-thiazol-2-yl)acetamide $^1$H NMR (400 MHz, DMSO-d$_6$) δ 0.23-0.30 (m, 1H), 0.37-0.48 (m, 2H), 0.55-0.65 (m, 1H), 0.94-0.98 (m, 3H), 1.12-1.18 (m, 1H), 1.34 (d, 3H), 2.17 (s, 3H), 2.44 (s, 3H), 2.87-2.91 (m, 2H), 3.33 (s, 1H), 4.75 (s, 2H), 7.75 (br s, 1H), 7.87 (s, 1H), 8.01 (s, 1H), 12.11 (br s, 1H). m/z (ES+), [M+H]$^+$=463; acid, HPLC t$_R$=1.57 min.

Intermediate 23

N-(5-{2-[(1S)-1-Cyclopropylethyl]-1-oxo-7-(propan-2-ylsulfamoyl)-2,3-dihydro-1H-isoindol-5-yl}-4-methyl-1,3-thiazol-2-yl)acetamide m/z (ES+), [M+H]$^+$=535.2.

Intermediate 24

N-(5-{2-[(1S)-1-Cyclopropylethyl]-7-(oxetan-3-ylsulfamoyl)-1-oxo-2,3-dihydro-1H-isoindol-5-yl}-4-methyl-1,3-thiazol-2-yl)acetamide $^1$H NMR (300 MHz, DMSO-d$_6$) δ 0.15-0.65 (m, 4H), 1.10-1.19 (m, 1H), 1.33 (d, 3H), 2.18 (s, 3H), 2.27 (s, 3H), 3.64-3.70 (m, 1H), 4.33-4.56 (m, 5H), 4.75 (s, 2H), 7.84 (s, 1H), 8.01 (s, 1H), 8.56-8.59 (m, 1H), 12.29 (s, 1H).

m/z (ES+), [M+H]$^+$=491; acid, HPLC t$_R$=1.42 min.

Intermediate 25

N-(5-{7-(Ethylsulfamoyl)-1-oxo-2-[(2S)-1,1,1-trifluoropropan-2-yl]-2,3-dihydro-1H-isoindol-5-yl}-4-methyl-1,3-thiazol-2-yl)acetamide $^1$H NMR (300 MHz, DMSO-d$_6$) δ 0.94 (t, 3H), 1.52 (d, 3H), 2.20 (s, 3H), 2.44 (s, 3H), 2.88-2.94 (m, 2H), 4.62 (d, 1H), 4.83 (d, 1H), 5.06-5.16 (m, 1H), 7.22-7.36 (m, 2H), 7.91 (d, 1H), 8.02 (d, 1H).

m/z (ES+), [M+H]$^+$=491; acid, HPLC t$_R$=1.49 min.

Intermediate 26

N-(4-Methyl-5-{1-oxo-7-(propan-2-ylsulfamoyl)-2-[(2S)-1,1,1-trifluoropropan-2-yl]-2,3-dihydro-1H-isoindol-5-yl}-1,3-thiazol-2-yl)acetamide $^1$H NMR (300 MHz, DMSO-d$_6$) δ 0.95 (d, 3H), 1.04 (d, 3H), 1.54 (d, 3H), 2.18 (s, 3H), 2.46 (s, 3H), 3.29-3.36 (m, 1H), 4.64 (d, 1H), 4.85 (d, 1H), 5.08-5.18 (m, 1H), 7.28 (d, 1H), 7.93 (d, 1H), 8.03 (d, 1H), 12.34 (s, 1H).
m/z (ES+), [M+H]$^+$=505.3; FA, HPLC t$_R$=1.54 min.

Intermediate 27

N-(4-Methyl-5-{7-(oxetan-3-ylsulfamoyl)-1-oxo-2-[(2S)-1,1,1-trifluoropropan-2-yl]-2,3-dihydro-1H-isoindol-5-yl}-1,3-thiazol-2-yl)acetamide $^1$H NMR (300 MHz, DMSO-d$_6$) δ 1.55 (d, 3H), 2.19 (s, 3H), 2.46 (s, 3H), 4.35-4.40 (m, 2H), 4.48-4.57 (2H, m) 4.64-4.74 (2H, m), 4.82 (1H, d), 5.07-5.16 (m, 1H), 7.89 (d, 1H), 8.02 (d, 1H), 8.60 (brs, 1H), 12.34 (brs, 1H).
m/z (ES+), [M+H]$^+$=519.3; FA, HPLC t$_R$=1.38 min.

Intermediate 28

N-(5-{2-[(1S)-1-Cyclopropylethyl]-7-(methylsulfanyl)-1-oxo-2,3-dihydro-1H-isoindol-5-yl}-4-methyl-1,3-thiazol-2-yl)acetamide Sodium methanethiolate (90 mg, 1.28 mmol) was added to a slurry of N-(5-{7-chloro-2-[(1S)-1-cyclopropylethyl]-1-oxo-2,3-dihydro-1H-isoindol-5-yl}-4-methyl-1,3-thiazol-2-yl)acetamide (Intermediate 6, 250 mg, 0.64 mmol) in dry DMF (5 mL). The vial was capped and inserted into an aluminium block at 100° C. The reaction was stirred overnight. Additional sodium methanethiolate (200 mg, 2.85 mmol) was added and the reaction was heated to 100° C. for another 6 h. The reaction was cooled down and diluted with water. The formed solids were filtered off, washed with water and dried to give the title compound (142 mg) as a solid.
$^1$H NMR (600 MHz, DMSO-d$_6$) δ 0.19-0.25 (m, 1H), 0.33-0.43 (m, 2H), 0.53-0.6 (m, 1H), 1.06-1.14 (m, 1H), 1.26 (d, 3H), 2.15 (s, 3H), 2.40 (s, 3H), 2.48 (s, 3H), 3.47-3.57 (m, 1H), 4.54 (s, 2H), 7.18 (s, 1H), 7.36 (s, 1H), 12.19 (s, 1H).
m/z (ES+), [M+H]$^+$=402.2, TFA System 2, HPLC t$_R$=1.08 min.

Intermediate 29

N-(4-Methyl-5-{7-(methylsulfanyl)-1-oxo-2-[(2S)-1,1,1-trifluoropropan-2-yl]-2,3-dihydro-1H-isoindol-5-yl}-1,3-thiazol-2-yl)acetamide Prepared from Intermediate 9 using the method of Intermediate 28.
m/z (ES+), [M+Na]$^+$=430; acid, HPLC t$_R$=1.43 min.

Intermediate 30

N-(5-{2-[(1S)-1-Cyclopropylethyl]-7-(methylsulfonyl)-1-oxo-2,3-dihydro-1H-isoindol-5-yl}-4-methyl-1,3-thiazol-2-yl)acetamide m-CPBA (3.33 g, 19.30 mmol) was added to N-(5-{2-[(1S)-1-cyclopropylethyl]-7-(methylsulfanyl)-1-oxo-2,3-dihydro-1H-isoindol-5-yl}-4-methyl-1,3-thiazol-2-yl)acetamide (Intermediate 28, 3.1 g, 7.72 mmol) in DCM (120 mL). The resulting mixture was stirred at 0° C. for 1 h. Then warmed to rt and stirred for 1 h. The reaction mixture was quenched with saturated NaHCO$_3$ (200 mL) and extracted with DCM (3×200 mL). The organic layer was dried over Na$_2$SO$_4$, filtered and evaporated to give a yellow solid. The crude product was purified by preparative HPLC with the following condition: Column: X Bridge RP 18, 19*150 mm, 5 um; Mobile Phase A: Water 10 nmol NH$_4$HCO$_3$, Mobile Phase B: MeCN; Flow rate: 30 mL/min; Gradient: 25% B to 75% B in 8 min; detection at 254 nm to give the title compound (1.20 g) as a white solid.
$^1$H NMR (500 MHz, DMSO-d$_6$) δ 0.24-0.30 (m, 1H), 0.38-0.46 (m, 2H), 0.57-0.62 (m, 1H), 1.11-1.20 (m, 1H), 1.31 (d, 3H), 2.17 (s, 3H), 2.44 (s, 3H), 3.59-3.64 (m, 1H), 3.63 (s, 3H), 4.70 (s, 2H), 8.00 (d, 1H), 8.05 (d, 1H), 12.30 (s, 1H).
m/z (ES+), [M+H]$^+$=434.1; TFA System 2, HPLC t$_R$=1.340 min.

Intermediate 31

N-(4-Methyl-5-{7-(methylsulfonyl)-1-oxo-2-[(2S)-1,1,1-trifluoropropan-2-yl]-2,3-dihydro-1H-isoindol-5-yl}-1,3-thiazol-2-yl)acetamide Prepared from Intermediate 29 following the method used for Intermediate 30.
$^1$H NMR (300 MHz, DMSO-d$_6$) δ 1.52 (3H, d), 2.18 (3H, s), 2.46 (3H, s), 3.62 (3H, s), 4.61 (1H, d), 4.81 (1H, d), 5.06-5.16 (1H, m), 8.04 (1H, d), 8.09 (1H, d), 12.34 (1H, s)
m/z (ES+), [M+H]$^+$=462; acid, HPLC t$_R$=1.36 min.

Intermediate 32

6-(2-Amino-4-methyl-1,3-thiazol-5-yl)-2-[(1S)-1-cyclopropylethyl]-N-methyl-3-oxo-2,3-dihydro-1H-isoindole-4-sulfonamide 3 M HCl (19 mL) was added to N-(5-{2-[(1S)-1-cyclopropylethyl]-7-(methylsulfamoyl)-1-oxo-2,3-dihydro-1H-isoindol-5-yl}-4-methyl-1,3-thiazol-2-yl)acetamide (Intermediate 18) (2.6 g) in ethanol (20 mL). The resulting mixture was stirred at 80° C. for 3 h. The solvent was removed and the residue was dissolved in DCM (50 mL). The reaction mixture was adjusted to pH=8 with saturated NaHCO$_3$. The phases were separated and the organic layer was dried over Na$_2$SO$_4$, filtered and evaporated to give crude product (1.90 g) as a yellow solid.
$^1$H NMR (400 MHz, DMSO-d$_6$) δ 7.84 (s, 1H), 7.74 (d, 1H), 7.61 (q, 1H), 7.34 (s, 2H), 4.72 (s, 2H), 3.73-3.56 (m, 1H), 2.49 (s, 3H), 2.31 (s, 3H), 1.31 (d, 3H), 1.24-1.03 (m, 1H), 0.62-0.58 (m, 1H), 0.47-0.39 (m, 2H), 0.31-0.27 (m, 1H).
m/z (ES+), [M+H]$^+$=407; acid, HPLC t$_R$=0.90 min.
The following intermediates 33-40 were made following the method used for Intermediate 32 starting from the appropriate acetamide:

Intermediate 33

5-(2-Amino-4-methyl-1,3-thiazol-5-yl)-2-[(1S)-1-cyclopropylethyl]-7-(methylsulfonyl)-2,3-dihydro-1H-isoindol-1-one $^1$H NMR (500 MHz, DMSO-d$_6$) δ 0.23-0.29 (m, 1H), 0.37-0.47 (m, 2H), 0.56-0.62 (m, 1H), 1.09-1.17 (m, 1H), 1.29 (d, 3H), 2.30 (s, 3H), 3.58-3.64 (m, 1H), 3.61 (s, 3H), 4.66 (s, 2H), 7.31 (s, 2H), 7.86-7.89 (m, 2H).

m/z (ES+), [M+H]$^+$=392; TFA System 2, HPLC $t_R$=1.12 min.

Intermediate 34

5-(2-Amino-4-methyl-1,3-thiazol-5-yl)-7-(methyl-sulfonyl)-2-[(2S)-1,1,1-trifluoropropan-2-yl]-2,3-dihydro-1H-isoindol-1-one $^1$H NMR (300 MHz, DMSO-d$_6$) δ 1.51 (d, 3H), 2.32 (s, 3H), 3.62 (s, 3H), 4.04-4.57 (d, 1H), 4.78 (d, 1H), 5.03-5.13 (m, 1H), 7.39 (s, 2H), 7.90-7.92 (m, 2H).

m/z (ES+), [M+H]$^+$=420; acid, HPLC $t_R$=0.68 min.

Intermediate 35

6-(2-Amino-4-methyl-1,3-thiazol-5-yl)-2-[(1S)-1-cyclopropylethyl]-N-ethyl-3-oxo-2,3-dihydro-1H-isoindole-4-sulfonamide $^1$H NMR (300 MHz, DMSO-d$_6$) δ 0.24-0.30 (m, 1H), 0.36-0.47 (m, 2H), 0.55-0.62 (m, 1H), 0.83-0.87 (m, 1H), 1.05-1.39 (m, 6H), 2.3 (s, 2H)), 3.58-3.67 (m, 1H), 4.70 (s, 2H), 7.34 (s, 2H), 7.60 (q, 1H), 7.7 (d, 1H), 7.82 (d, 1H); 3H obscured.

m/z (ES+), [M+H]$^+$=421; acid, HPLC $t_R$=0.78 min.

Intermediate 36

6-(2-Amino-4-methyl-1,3-thiazol-5-yl)-2-[(1S)-1-cyclopropylethyl]-3-oxo-N-(propan-2-yl)-2,3-dihydro-1H-isoindole-4-sulfonamide $^1$H NMR (300 MHz, DMSO-d$_6$) δ 0.21-0.27 (m, 1H), 0.36-0.45 (m, 2H), 0.56-0.62 (m, 1H), 0.96 (d, 3H) 0.99 (d, 3H), 1.08-1.18 (m, 1H), 1.31 (d, 3H), 2.30 (s, 3H), 3.19-3.30 (m, 1H), 3.56-3.66 (m, 1H), 4.71 (s, 2H), 7.35 (s, 2H), 7.72-7.78 (m, 2H), 7.81 (m, 1H).

m/z (ES+), [M+H]$^+$=435; base, HPLC $t_R$=1.30 min.

Intermediate 37

6-(2-Amino-4-methyl-1,3-thiazol-5-yl)-N-methyl-3-oxo-2-[(2S)-1,1,1-trifluoropropan-2-yl]-2,3-dihydro-1H-isoindole-4-sulfonamide $^1$H NMR (400 MHz, DMSO-d$_6$) δ 1.52 (d, 3H), 1.87 (s, 2H), 2.32 (s, 3H), 4.25 (d, 2H), 4.59 (d, 1H), 7.39 (s, 2H), 7.77 (m, 1H), 7.85 (d, 1H), 8.34 (s, 1H).

m/z (ES+), [M+H]$^+$=435.05; TFA, HPLC $t_R$=1.16 min.

Intermediate 38

6-(2-Amino-4-methyl-1,3-thiazol-5-yl)-N-ethyl-3-oxo-2-[(2S)-1,1,1-trifluoropropan-2-yl]-2,3-dihydro-1H-isoindole-4-sulfonamide $^1$H NMR (300 MHz, DMSO-d$_6$) δ 0.78-0.87 (m, 1H), 0.97 (t, 3H) 1.50 (d, 3H), 2.31 (s, 3H), 2.83-2.93 (m, 2H), 4.63 (d, 1H), 4.78 (d, 1H), 5.04-5.14 (m, 1H), 7.30-7.39 (m, 3H), 7.77 (d, 1H), 7.83 (d, 1H).

m/z (ES+), [M+H]$^+$=449; acid, HPLC $t_R$=0.74 min.

Intermediate 39

6-(2-Amino-4-methyl-1,3-thiazol-5-yl)-3-oxo-N-(propan-2-yl)-2-[(2S)-1,1,1-trifluoropropan-2-yl]-2,3-dihydro-1H-isoindole-4-sulfonamide $^1$H NMR (300 MHz, DMSO-d$_6$) δ 0.93 (d, 3H), 1.02 (d, 3H), 1.51 (d, 3H), 2.31 (s, 3H), 3.28 (h, 1H), 4.59 (d, 1H), 4.80 (d, 1H), 5.05-5.15 (m, 1H), 7.27 (d, 1H), 7.39 (s, 2H), 7.78 (d, 1H), 7.83 (d, 1H).

m/z (ES+), [M+H]$^+$=463.3; TFA, HPLC $t_R$=0.77 min.

Intermediate 40

6-(2-Amino-4-methyl-1,3-thiazol-5-yl)-2-[(2S)-3,3-dimethylbutan-2-yl]-N-methyl-3-oxo-2,3-dihydro-1H-isoindole-4-sulfonamide m/z (ES+), [M+H]$^+$=423.2; pH 3, HPLC $t_R$=1.19 min.

Intermediate 41

6-(2-Amino-4-methyl-1,3-thiazol-5-yl)-2-[(1S)-1-cyclopropylethyl]-N-(oxetan-3-yl)-3-oxo-2,3-dihydro-1H-isoindole-4-sulfonamide LiOH (98 mg, 4.08 mmol) in water (0.2 mL) was added to N-(5-{2-[(1S)-1-cyclopropylethyl]-7-(oxetan-3-ylsulfamoyl)-1-oxo-2,3-dihydro-1H-isoindol-5-yl}-4-methyl-1,3-thiazol-2-yl)acetamide (Intermediate 24, 200 mg, 0.41 mmol) in MeOH (10 mL) under nitrogen. The resulting solution was stirred at 60° C. for 20 h. The reaction mixture was diluted with DCM (20 mL), and washed sequentially with water (25 mL×2) and saturated brine (25 mL×2). The organic layer was dried over Na$_2$SO$_4$, filtered and evaporated to afford the title compound (160 mg, 87%) as a yellow solid.

$^1$H NMR (400 MHz, DMSO-d$_6$) δ 0.26-0.30 (m, 1H), 0.39-0.46 (m, 2H), 0.58-0.63 (m, 1H), 1.13-1.17 (m, 1H), 1.33 (d, 3H), 2.30 (s, 3H), 3.41-3.47 (m, 1H), 3.61-3.69 (m, 1H), 4.32-4.39 (m, 2H), 4.53 (q, 2H), 4.71 (s, 2H), 7.37 (s, 2H), 7.71 (d, 1H), 7.83 (d, 1H), 8.60 (s, 1H).

m/z (ES+), [M+H]$^+$=449.3; TFA, HPLC $t_R$=0.91 min.

The following intermediates 42-43 were made following the method used for Intermediate 41 starting from the appropriate acetamide:

Intermediate 42

6-(2-Amino-4-methyl-1,3-thiazol-5-yl)-2-tert-butyl-N-methyl-3-oxo-2,3-dihydro-1H-isoindole-4-sulfonamide Used crude without purification for next step.

Intermediate 43

6-(2-Amino-4-methyl-1,3-thiazol-5-yl)-N-(oxetan-3-yl)-3-oxo-2-[(2S)-1,1,1-trifluoropropan-2-yl]-2,3-dihydro-1H-isoindole-4-sulfonamide m/z (ES+), [M+H]$^+$=476.9; NH$_4$HCO$_3$, HPLC $t_R$=0.79 min.

Intermediate 44

Benzyl (2R)-2-methyl-5-oxopiperazine-1-carboxylate

Benzyl carbonochloridate (408 mg, 2.39 mmol) was added to (R)-5-methylpiperazin-2-one hydrochloride (300 mg, 1.99 mmol) and sodium carbonate (633 mg, 5.98 mmol) in EtOAc:water 1:1 (8 mL) at 25° C. under nitrogen. The resulting mixture was stirred at rt for 12 h. The reaction mixture was diluted with EtOAc and water (10 mL), extracted with EtOAc (3×5 mL) and washed with saturated brine (2×10 mL). The organic layer was dried over sodium sulfate, filtered and evaporated. The crude product was purified by flash silica chromatography, elution gradient 0 to 2% DCM in MeOH. Pure fractions were evaporated to dryness to afford the title compound (410 mg) as a colourless oil.

$^1$H NMR (400 MHz, DMSO-$d_6$) δ 1.19 (d, 3H), 2.98-3.03 (m, 1H), 3.38-3.48 (m, 1H), 3.64-3.77 (m, 1H), 3.97-4.10 (m, 1H), 4.26-4.28 (m, 1H), 5.11 (d, 2H), 7.27-7.47 (m, 5H), 8.02-8.08 (br s, 1H).

The following Intermediates 45-49 were prepared analogously to Intermediate 44 using the appropriate commercially available amines:

Intermediate 45

Benzyl 2,2-dimethyl-5-oxopiperazine-1-carboxylate $^1$H NMR (300 MHz, DMSO-$d_6$) δ 1.36 (s, 6H), 3.13 (d, 2H), 3.91 (s, 2H), 5.08 (s, 2H), 7.32-7.36 (m, 1H), 7.36-7.39 (m, 4H), 8.21 (t, 1H).

Intermediate 46

Benzyl (2S)-2-methyl-5-oxopiperazine-1-carboxylate $^1$H NMR (300 MHz, DMSO-$d_6$) δ 1.15 (t, 3H), 2.99 (ddd, 1H), 3.30-3.47 (m, 2H), 3.96-4.09 (m, 1H), 4.18-4.34 (m, 1H), 5.10 (d, 2H), 7.26-7.44 (m, 5H), 7.99-8.07 (m, 1H).

Intermediate 47

Benzyl (3R)-3-methyl-5-oxopiperazine-1-carboxylate $^1$H NMR (300 MHz, DMSO-$d_6$) δ 8.17-8.09 (m, 1H), 7.45-7.26 (m, 5H), 5.11 (d, 2H), 4.05-3.80 (m, 2H), 3.74 (dd, 1H), 3.56-3.43 (m, 1H), 3.20-3.00 (m, 1H), 1.07 (d, 3H).

Intermediate 48

Benzyl (3S)-3-methyl-5-oxopiperazine-1-carboxylate $^1$H NMR (300 MHz, DMSO-$d_6$) δ 1.06 (d, 3H), 3.00-3.20 (m, 1H), 3.43-3.56 (m, 1H), 3.74 (dd, 1H), 3.80-4.05 (m, 2H), 5.11 (d, 2H), 7.27-7.45 (m, 5H), 8.13 (s, 1H).

Intermediate 49

Benzyl 2,2-dimethyl-5-oxopiperazine-1-carboxylate $^1$H NMR (300 MHz, DMSO-$d_6$) δ 1.36 (s, 6H), 3.13 (d, 2H), 3.91 (s, 2H), 5.08 (s, 2H), 7.31-7.40 (m, 5H), 8.21 (t, 1H).

Intermediate 50

4-(6-Bromopyridin-2-yl)morpholin-3-one

Xantphos (1.145 g, 1.98 mmol) was added to 2,6-dibromopyridine (3.51 g, 14.84 mmol), morpholin-3-one (1 g, 9.89 mmol), PdOAc$_2$ (0.111 g, 0.49 mmol) and Cs$_2$CO$_3$ (6.45 g, 19.78 mmol) in 1,4-dioxane (100 mL) at 25° C. under nitrogen. The resulting mixture was stirred at 80° C. for 12 h. The reaction mixture was filtered through celite, evaporated to dryness and redissolved in DCM (75 mL), and washed sequentially with water (50 mL×2) and saturated brine (50 mL×2). The organic layer was dried over Na$_2$SO$_4$, filtered and evaporated to afford crude product. The crude product was purified by flash silica chromatography, elution gradient 0 to 5% petroleum ether in EtOAc, and pure DCM. Pure fractions were evaporated to dryness to afford the title compound (1.20 g, 47%).

$^1$H NMR (400 MHz, DMSO-$d_6$) δ 3.88-4.05 (4H, m), 4.28 (2H, s), 7.49 (1H, dd), 7.80 (1H, t), 8.10 (1H, dd).

The following intermediates 51-72 were prepared analogously to Intermediate 50 using the appropriate amide, lactam, carbamate or urea.

Intermediate 51

1-(6-Bromopyridin-2-yl)-3-methylimidazolidin-2-one m/z (ES+), [M+H]$^+$=356.358; acid, HPLC $t_R$=1.43 min.

Intermediate 52

1-(6-Bromopyridin-2-yl)-4-methylpiperazin-2-one $^1$H NMR (300 MHz, DMSO-$d_6$) δ 2.29 (s, 3H), 2.75 (t, 2H), 3.21 (s, 2H), 3.84 (dd, 2H), 7.48 (d, 1H), 7.78 (t, 1H), 7.97 (d, 1H).

Intermediate 53

Benzyl 4-(6-bromopyridin-2-yl)-3-oxopiperazine-1-carboxylate m/z (ES+), [M+H]$^+$=390; acid, HPLC $t_R$=1.56 min.

Intermediate 54

Benzyl (2R)-4-(6-bromopyridin-2-yl)-2-methyl-3-oxopiperazine-1-carboxylate m/z (ES+), [M+H]$^+$=404.406; acid, HPLC $t_R$=1.22 min.

Intermediate 55

Benzyl (2S)-4-(6-bromopyridin-2-yl)-2-methyl-3-oxopiperazine-1-carboxylate m/z (ES+), [M+H]$^+$=404.406; acid, HPLC $t_R$=1.19 min.

Intermediate 56

Benzyl (2R)-4-(6-bromopyridin-2-yl)-2-methyl-5-oxopiperazine-1-carboxylate

Lactam starting material: Intermediate 44.
m/z (ES+), [M+H]$^+$=404.406; acid, HPLC $t_R$=0.99 min.

Intermediate 57

Benzyl 4-(6-bromopyridin-2-yl)-2,2-dimethyl-5-oxopiperazine-1-carboxylate

Lactam starting material: Intermediate 49.
$^1$H NMR (300 MHz, DMSO-d$_6$) δ 1.41 (s, 6H), 4.11 (s, 2H), 4.31 (s, 2H), 5.11 (s, 2H), 7.28-7.41 (m, 5H), 7.47 (d, 1H), 7.81 (t, 1H), 8.04 (d, 1H).

Intermediate 58

Benzyl (3R)-4-(6-bromopyridin-2-yl)-3-methyl-5-oxopiperazine-1-carboxylate

Lactam starting material: Intermediate 47.
m/z (ES+), [M+H]$^+$=404.406; acid, HPLC $t_R$=0.96 min.

Intermediate 59

Benzyl (3S)-4-(6-bromopyridin-2-yl)-3-methyl-5-oxopiperazine-1-carboxylate

Lactam starting material: Intermediate 48
$^1$H NMR (300 MHz, DMSO-d$_6$) δ 1.17 (d, 3H), 3.50-3.54 (m, 1H), 3.91-4.18 (m, 2H), 4.43 (t, 1H), 4.66 (d, 1H), 5.16 (d, 2H), 7.21-7.61 (m, 6H), 7.74-7.98 (m, 2H).

Intermediate 60

(8aS)-2-(6-Bromopyridin-2-yl)hexahydropyrrolo[1,2-a]pyrazine-1,4-dione $^1$H NMR (400 MHz, DMSO-d$_6$) δ 1.86-1.97 (m, 2H), 2.06-2.14 (m, 1H), 2.23-2.30 (m, 1H), 3.43-3.47 (m, 2H), 4.49-4.63 (m, 3H), 7.51 (dd, 1H), 7.82 (t, 1H), 7.97 (dd, 1H).
m/z (ES+), [M+H]$^+$=310.1; FA, HPLC $t_R$=1.21 min.

Intermediate 61

1-(6-Bromopyridin-2-yl)-4-(2-{[tert-butyl(dimethyl)silyl]oxy}ethyl)piperazin-2-one Lactam starting material: J. Med. Chem., 2015, 58, 9179.
$^1$H NMR (300 MHz, CDCl$_3$) δ 0.10 (s, 6H), 0.93 (s, 9H), 2.65-2.73 (m, 2H), 2.95-3.03 (m, 2H), 3.46-3.52 (m, 2H), 3.82-3.88 (m, 2H), 4.03-4.09 (m, 2H), 7.29 (d, 1H), 7.56 (t, 1H), 8.09 (dd, 1H).

Intermediate 62

Benzyl (2S)-4-(6-bromopyridin-2-yl)-2-methyl-5-oxopiperazine-1-carboxylate

Lactam starting material: Intermediate 46.
m/z (ES+), [M+H]$^+$=404.406; acid, HPLC $t_R$=1.22 min.

Intermediate 63

Benzyl 4-(6-bromopyridin-2-yl)-2,2-dimethyl-3-oxopiperazine-1-carboxylate

Lactam starting material: Intermediate 45.
$^1$H NMR (400 MHz, DMSO-d$_6$) δ 1.68 (s, 6H), 3.81-3.83 (m, 2H), 3.98-4.03 (m, 2H), 5.13 (s, 2H), 7.34-7.43 (m, 5H), 7.49 (dd, 1H), 7.80 (t, 1H), 7.94 (dd, 1H).
m/z (ES+), [M+H]$^+$=420.0; TFA, HPLC $t_R$=1.77 min.

Intermediate 64 tert-Butyl 4-(6-bromopyridin-2-yl)-3-oxo-1,4-diazepane-1-carboxylate $^1$H NMR (300 MHz, DMSO-d$_6$) δ 1.39 (s, 9H), 1.72-1.85 (m, 2H), 3.52-3.62 (m, 2H), 4.10-4.20 (m, 2H), 4.27 (s, 2H), 7.43 (d, 1H), 7.56 (t, 1H), 7.77 (t, 1H).

Intermediate 65 tert-Butyl 4-(6-bromopyridin-2-yl)-5-oxo-1,4-diazepane-1-carboxylate $^1$H NMR (300 MHz, DMSO-d$_6$) δ 1.36 (d, 9H), 2.85-2.90 (dd, 2H), 3.57-3.68 (m, 4H), 4.09-4.13 (m, 2H), 7.44-7.46 (m, 1H), 7.75-7.79 (m, 2H).
m/z (ES+), [M+H]$^+$=370/372; base, HPLC $t_R$=1.08 min.

Intermediate 66

1-(6-Bromopyridin-2-yl)pyrrolidin-2-one $^1$H NMR (400 MHz, CDCl$_3$) δ 2.12 (p, 2H), 2.65 (t, 2H), 4.01-4.14 (m, 2H), 7.19 (d, 1H), 7.45-7.59 (m, 1H), 8.35 (d, 1H).
m/z (ES+), [M+H]$^+$=241/243; TFA System 2, HPLC $t_R$=1.51 min.

Intermediate 67

(5S)-1-(6-Bromopyridin-2-yl)-5-({[tert-butyl(dimethyl)silyl]oxy}methyl)pyrrolidin-2-one Lactam starting material: Angewandte Chemie—Int. Ed., 2006, 45, 1463.
$^1$H NMR (300 MHz, DMSO-d$_6$) δ −0.18 (s, 3H), −0.07 (s, 3H), 0.77 (s, 9H), 1.94-2.04 (m, 1H), 2.05-2.31 (m, 1H), 2.31-2.50 (m, 1H), 2.65-2.77 (m, 1H), 3.65-3.81 (m, 1H), 3.90-3.95 (dd, 1H), 4.52-4.70 m, (m, 1H), 7.37-7.46 (m, 1H), 7.68-7.81 (m, 1H), 8.22-8.33 (m, 1H).
m/z (ES+), [M+H]$^+$=385.387; acid, HPLC $t_R$=1.28 min.

Intermediate 68

(5R)-1-(6-Bromopyridin-2-yl)-5-({[tert-butyl(dimethyl)silyl]oxy}methyl)pyrrolidin-2-one Lactam starting material: Helv. Chim. Acta, 1990, 73, 122.
$^1$H NMR (400 MHz, DMSO-d$_6$) δ −0.17 (s, 3H), −0.05 (s, 3H), 0.79 (s, 9H), 1.96-2.02 (m, 1H), 2.19-2.24 (m, 1H), 2.40-2.47 (m, 1H), 2.67-2.76 (m, 1H), 3.77 (dd, 1H), 3.93

(dd, 1H), 4.63-4.66 (m, 1H), 7.35-7.39 (m, 1H), 7.74-7.79 (m, 1H), 8.28 (d, 1H).
m/z (ES+), [M+H]$^+$=385.1; FA, HPLC t$_R$=1.48 min.

Intermediate 69

(4R)-1-(6-Bromopyridin-2-yl)-4-{[tert-butyl(dimethyl)silyl]oxy}pyrrolidin-2-one

Lactam starting material: Tetrahedron, 2000, 56, 7705.
$^1$H NMR (400 MHz, DMSO-d$_6$) δ 0.10 (s, 6H), 0.86 (s, 9H), 2.39 (d, 1H), 3.01 (dd, 1H), 3.80 (d, 1H), 4.11 (dd, 1H), 4.55-4.61 (m, 1H), 7.39 (d, 1H), 7.77 (t, 1H), 8.30 (d, 1H).
m/z (ES+), [M+H]$^+$=373.1; TFA, HPLC t$_R$=1.91 min.

Intermediate 70

(3S)-1-(6-Bromopyridin-2-yl)-3-{[tert-butyl(dimethyl)silyl]oxy}pyrrolidin-2-one

Lactam starting material: Org. Lett., 2005, 7, 553.
$^1$H NMR (400 MHz, DMSO-d$_6$) δ 0.14 (s, 3H), 0.90 (s, 9H), 1.88 (dq, 1H), 2.44 (m, 1H), 2.53 (s, 1H), 3.66 (td, 1H), 3.97 (ddd, 1H), 4.63 (dd, 1H), 7.41 (dd, 1H), 7.75-7.81 (m, 1H), 8.30 (ddd, 1H).
m/z (ES+), [M+H]$^+$=373.0; TFA, HPLC t$_R$=1.94 min.

Intermediate 71

(3R)-1-(6-Bromopyridin-2-yl)-3-{[tert-butyl(dimethyl)silyl]oxy}pyrrolidin-2-one

Lactam starting material: WO2014008285A1.
$^1$H NMR (300 MHz, DMSO-d$_6$) δ 0.14 (s, 3H), 0.15 (s, 3H), 0.90 (s, 9H), 1.85-1.92 (m, 1H), 2.39-2.48 (m, 1H), 3.64-3.71 (m, 1H), 3.95-4.02 (m, 1H), 4.62 (dd, 1H), 7.40 (dd, 1H), 7.74-7.79 (m, 1H), 8.30 (dd, 1H).

Intermediate 72

6-(6-Bromopyridin-2-yl)-6,7-dihydro-5H-pyrrolo[3,4-b]pyridin-5-one $^1$H NMR (300 MHz, DMSO-d$_6$) δ 5.07 (s, 2H), 7.46 (d, 1H), 7.60 (dd, 1H), 7.86 (t, 1H), 8.24 (dd, 1H), 8.52 (d, 1H), 8.87 (dd, 1H).

Intermediate 66, Alternative Preparation 1-(6-Bromopyridin-2-yl)pyrrolidin-2-one 1) 4-Bromo-N-(6-bromopyridin-2-yl)butanamide 6-Bromopyridin-2-amine (5.09 g, 29.42 mmol) and 4-bromobutanoyl chloride (6.55 g, 35.30 mmol) were added to MeCN (50 mL) at 0° C. in a 250 ml flask. Then pyridine (3.56 mL, 44.13 mmol) was added dropwise to the mixture. The reaction mixture was allowed to reach rt and was stirred for 2 h. LCMS showed product formation. The reaction mixture was stirred at rt overnight. The MeCN was concentrated and then the mixture was diluted with 200 ml of EtOAc, washed twice with 2×100 ml of 0.4 M HCl and once with brine. The organic phase was dried over a phase separator and then concentrated to yield the crude compound as a yellow oil (9.35 g). Used in further reactions without purification.

$^1$H NMR (300 MHz, CDCl$_3$) δ 2.27 (p, 2H), 2.59 (t, 2H), 3.51 (t, 2H), 7.22 (d, 1H), 7.56 (t, 1H), 8.00 (s, 1H), 8.14 (d, 1H).

2) 1-(6-Bromopyridin-2-yl)pyrrolidin-2-one

4-Bromo-N-(6-bromopyridin-2-yl)butanamide (9.43 g, 29.29 mmol) and cesium carbonate (10.73 g, 32.95 mmol) were diluted in DMF (50 mL). The reaction mixture was stirred at 60° C. for 4 h. The reaction mixture was cooled to rt, diluted in 200 ml of EtOAc, washed twice with 150 ml of water, once with 100 ml of 0.2 M HCl and then the organic phase was dried over a phase separator and concentrated to dryness.

The residue was purified by automated flash chromatography on a Biotage® KP-SIL 340 g column. A gradient from 0% to 75% of EtOAc in heptane over 15 CV was used as mobile phase. The product was collected using the wavelength 254 nm; (5.22 g) was obtained as a yellow glass solid.
$^1$H NMR (400 MHz, DMSO-d$_6$) δ 2.05 (m, 2H), 2.59 (dd, 2H), 3.93 (dd, 2H), 7.37 (dd, 1H), 7.76 (dd, 1H), 8.30 (dd, 1H).
m/z (ES+), [M+H]$^+$=243.0; TFA, HPLC t$_R$=1.51 min.

The following intermediates 73-77 were prepared analogously to Intermediate 66, alternative preparation, using the appropriate commercial ω-halo acyl halide or ω-halo isocyanate (Intermediate 75).

Intermediate 73

1-(6-Bromopyridin-2-yl)piperidin-2-one $^1$H NMR (300 MHz, DMSO-d$_6$) δ 1.77-1.91 (m, 4H), 2.46-2.49 (m, 2H), 3.79-3.83 (m, 2H—partially obscured by HDO), 7.44 (dd, 1H), 7.71-7.82 (m, 2H).
m/z (ES+), [M+H]$^+$=254; FA, HPLC t$_R$=1.37 min.

Intermediate 74

3-(6-Bromopyridin-2-yl)-1,3-oxazinan-2-one $^1$H NMR (300 MHz, DMSO-d$_6$) δ 2.12 (p, 2H), 3.88 (t, 2H), 4.35 (t, 2H), 7.43 (dd, 1H), 7.75 (t, 1H), 7.88 (dd, 1H).
m/z (ES+), [M+H]$^+$=257.1; FA, HPLC t$_R$=1.30 min.

Intermediate 75

1-(6-Bromopyridin-2-yl)imidazolidin-2-one $^1$H NMR (400 MHz, DMSO-d$_6$) δ 3.39 (t, 2H), 3.94 (t, 2H), 7.19 (dd, 1H), 7.39 (s, 1H), 7.63 (dd, 1H), 8.17 (dd, 1H).

Intermediate 76

3-(6-Bromopyridin-2-yl)-1,3-oxazolidin-2-one $^1$H NMR (400 MHz, CDCl$_3$) δ 4.29 (t, 2H), 4.52 (t, 2H), 7.23 (d, 1H), 7.57 (t, 1H), 8.20 (d, 1H).
m/z (ES+), [M+H]$^+$=243.245; acid, HPLC t$_R$=1.40 min.

Intermediate 77

2-Bromo-6-(1,1-dioxido-1,2-thiazolidin-2-yl)pyridine $^1$H NMR (500 MHz, CDCl$_3$) δ 2.52 (p, 2H), 3.42 (t, 2H), 4.05 (t, 2H), 7.15 (d, 1H), 7.34 (d, 1H), 7.48 (t, 1H).
m/z (ES+), [M+H]$^+$=277/279; Method pH10 (long) 1.23 min.

Intermediate 78

N-(6-Bromopyridin-2-yl)-2-methoxy-N-methylacetamide

2-Methoxyacetyl chloride (128 mg, 1.18 mmol) was added to $Cs_2CO_3$ (697 mg, 2.14 mmol) and 6-bromo-N-methylpyridin-2-amine (200 mg, 1.07 mmol) in MeCN (50 mL) under nitrogen. The resulting mixture was stirred at rt for 16 h. The reaction mixture was filtered through celite. The reaction mixture was concentrated and diluted with EtOAc (50 mL), and washed sequentially with 0.1 M HCl (50 mL×2), saturated brine (50 mL×2). The organic layer was dried over $Na_2SO_4$, filtered and evaporated to afford title product (200 mg, 72%) as yellow solid.

$^1$H NMR (500 MHz, DMSO-$d_6$) δ 7.80 (t, 1H), 7.61 (d, 1H), 7.50 (d, 1H), 4.21 (s, 2H), 3.27 (s, 3H), 3.23 (s, 3H).

$^{13}$C NMR (126 MHz, DMSO-$d_6$) δ 169.7, 154.59, 141.17, 138.48, 124.94, 117.93, 71.07, 58.25, 33.86.

m/z (ES+), [M+H]$^+$=261.1; acid, HPLC $t_R$=0.68 min.

The following intermediates 79-80 were prepared following the method described for Intermediate 78 using the appropriate amine and acid chloride:

Intermediate 79

N-(6-Bromopyridin-2-yl)-N-ethyl-2-methoxyacetamide $^1$H NMR (300 MHz, DMSO-$d_6$) δ 1.08 (t, 3H), 3.19 (s, 3H), 3.80 (q, 2H), 4.10 (s, 2H), 7.53-7.58 (m, 2H), 7.83 (t, 1H).

m/z (ES+), [M+H]$^+$=275.1; acid, HPLC $t_R$=0.72 min.

Intermediate 80

(2S)—N-(6-Bromopyridin-2-yl)-2-methoxy-N-methylpropanamide $^1$H NMR (300 MHz, CDCl$_3$) δ 1.42 (d, 3H), 3.26 (s, 3H), 3.43 (s, 3H), 4.25 (q, 1H), 7.31-7.46 (m, 2H), 7.63 (t, 1H).

m/z (ES+), [M+H]$^+$=272.8; base, HPLC $t_R$=0.69 min.

Intermediate 81

(2R)—N-(6-Bromopyridin-2-yl)-2-methoxypropanamide (R)-2-Methoxypropanoyl chloride (531 mg, 4.33 mmol) was added to pyridine (0.467 mL, 5.78 mmol) and 6-bromopyridin-2-amine (500 mg, 2.89 mmol) in DCM (20 mL) at 0° C. under nitrogen. The resulting solution was stirred at rt for 2 h. The reaction mixture was quenched with water (20 mL), extracted with DCM (2×25 mL), the organic layer was dried over $Na_2SO_4$, filtered and evaporated to afford colourless oil. The crude product was purified by flash silica chromatography, elution gradient 0 to 50% petroleum ether in EtOAc. Pure fractions were evaporated to dryness to afford the title product (600 mg, 80%) as a colourless oil.

$^1$H NMR (300 MHz, CDCl$_3$) δ 1.47 (d, 3H), 3.48 (s, 3H), 3.89 (q, 1H), 7.25 (d, 1H), 7.58 (dd, 1H), 8.24 (d, 1H), 9.00 (s, 1H).

m/z (ES+), [M+H]$^+$=258.9; base, HPLC $t_R$=0.80 min.

Intermediate 82

N-(6-Bromopyridin-2-yl)-2-ethoxyacetamide

Prepared by the same general method as described for Intermediate 81.

$^1$H NMR (300 MHz, DMSO-$d_6$) δ 10.40 (s, 1H), 8.08 (d, 1H), 7.76 (t, 1H), 7.36 (d, 1H), 4.10 (s, 2H), 3.55 (q, 2H), 1.16 (t, 3H).

m/z (ES+), [M+H]$^+$=259.1; acid, HPLC $t_R$=0.96 min.

Intermediate 83

(2R)—N-(6-Bromopyridin-2-yl)-2-methoxy-N-methylpropanamide

NaH (93 mg, 3.86 mmol) was added to (2R)—N-(6-bromopyridin-2-yl)-2-methoxypropanamide (Intermediate 81, 500 mg, 1.93 mmol) in THF (20 mL) cooled to 0° C. under nitrogen. The resulting suspension was stirred at 0° C. for 15 minutes. Iodomethane (411 mg, 2.89 mmol) was added. The resulting suspension was stirred at 0° C. for 2 h. The mixture was filtered through a Celite pad. The filtrate was diluted with EtOAc (30 mL), washed with brine (20 mL). The organic layer was dried over $Na_2SO_4$, filtered and evaporated to afford a yellow residue. The crude product was purified by flash silica chromatography, elution gradient 0 to 100% EtOAc in petroleum ether. Pure fractions were evaporated to dryness to afford the title product (280 mg, 53%) as a colourless gum.

$^1$H NMR (300 MHz, DMSO-$d_6$) δ 1.23 (d, 3H), 3.06 (s, 3H), 3.27 (s, 3H), 4.16 (q, 1H), 7.54-7.58 (m, 2H), 7.85 (t, 1H).

m/z (ES+), [M+H]$^+$=275.2; acid, HPLC $t_R$=1.28 min.

Intermediate 84

N-(6-Bromopyridin-2-yl)-2-ethoxy-N-methylacetamide

Prepared by the same general method as described for Intermediate 83.

m/z (ES+), [M+H]$^+$=273.1; acid, HPLC $t_R$=1.33 min.

Intermediate 85

5-Bromo-2-[(1S)-1-cyclopropylethyl]-7-(methylsulfanyl)-2,3-dihydro-1H-isoindol-1-one 5-Bromo-7-chloro-2-[(1S)-1-cyclopropylethyl]-2,3-dihydro-1H-isoindol-1-one (Intermediate 1, 5.08 g, 16.15 mmol), sodium methanethiolate (3.38 g, 48.22 mmol) and 1,4-dioxane (60 mL) was placed in a 100 ml flask flushed with inert atmosphere and heated at 120° C. for 5.5 h. Subsequently the reaction mixture was filtered through celite which was washed with EtOAc. The organic solution was washed twice with water and then with brine, dried over sodium sulfate, filtered and concentrated to give a yellow solid. To the solid was added to diethyl ether and the mixture was stirred. The solid was collected by suction filtration. The solid was washed three times with diethyl ether and air dried to give the title product (4.95 g) as a white solid.

$^1$H NMR (500 MHz, DMSO-$d_6$) δ 0.18-0.23 (m, 1H), 0.31-0.43 (m, 2H), 0.51-0.59 (m, 1H), 1.03-1.12 (m, 1H), 1.24 (d, 3H), 2.46 (s, 3H), 3.45-3.54 (m, 1H), 4.49 (s, 2H), 7.32 (s, 1H), 7.53 (s, 1H).

Intermediate 86

5-Bromo-2-[(1S)-1-cyclopropylethyl]-7-(methylsulfonyl)-2,3-dihydro-1H-isoindol-1-one m-CPBA (4.62 g, 26.79 mmol) was added to 5-bromo-2-[(1S)-1-cyclopropylethyl]-7-(methylsulfanyl)-2,3-dihydro-1H-isoindol-1-one (Intermediate 85, 3.8 g) in DCM (50 mL) under nitrogen and the resulting mixture was stirred at rt for 2 h. The reaction mixture was diluted with DCM (200 mL), and washed sequentially with saturated NaHCO$_3$ (2×150 mL), and saturated brine (150 mL). The organic layer was dried over Na$_2$SO$_4$, filtered and evaporated to afford the crude product. The crude product was purified by flash silica chromatography, elution gradient 0 to 5% MeOH in DCM. Pure fractions were evaporated to dryness to afford the title compound (3.10 g) as a yellow solid.

$^1$H NMR (500 MHz, CD$_2$Cl$_2$) δ 0.36-0.42 (m, 1H), 0.43-0.49 (m, 1H), 0.49-0.55 (m, 1H), 0.66-0.74 (m, 1H), 1.04-1.12 (m, 1H), 1.39 (d, 3H), 3.58 (s, 3H), 3.74-3.80 (m, 1H), 4.48-4.65 (m, 2H), 7.94-7.98 (m, 1H), 8.32 (d, 1H).

m/z (ES+), [M+H]$^+$=360.1, acid, HPLC t$_R$=0.81 min.

Intermediate 87

7-(Benzylsulfanyl)-5-bromo-2-[(2S)-butan-2-yl]-2,3-dihydro-1H-isoindol-1-one

Prepared from Intermediate 5 following Method C.
m/z (ES+), [M+H]$^+$=390.3/392.3; pH3 HPLC t$_R$ 2.67 min.

Intermediate 88

6-Bromo-2-[(2S)-butan-2-yl]-3-oxo-2,3-dihydro-1H-isoindole-4-sulfonyl chloride

Prepared from Intermediate 87 following Method D
m/z (ES+), [M+H]$^+$=366/368; pH3 HPLC t$_R$ 2.11 min.

Intermediate 89

6-Bromo-2-[(2S)-butan-2-yl]-N-methyl-3-oxo-2,3-dihydro-1H-isoindole-4-sulfonamide Prepared from Intermediate 88 using Method E.
$^1$H NMR (500 MHz, CDCl$_3$) δ 0.90 (t, 3H), 1.29 (d, 3H), 1.65 (pent, 2H), 2.63 (d, 3H), 4.33 (d, 1H), 4.31-4.41 (m, 2H), 7.41 (dd, 1H), 7.81 (d, 1H), 8.19 (d, 1H).
m/z (ES+), [M+H]$^+$=366/368; Method pH10 (long), HPLC t$_R$ 1.93 min.

Intermediate 90

4-{6-[(4-Methyl-1,3-thiazol-2-yl)amino]pyridin-2-yl}morpholin-3-one

4-Methylthiazol-2-amine (200 mg, 1.75 mmol), 4-(6-bromopyridin-2-yl)morpholin-3-one (Intermediate 50, 450 mg, 1.75 mmol), 4-(6-bromopyridin-2-yl)morpholin-3-one (450 mg, 1.75 mmol), (9,9-dimethyl-9H-xanthene-4,5-diyl)bis(diphenylphosphine) (81 mg, 0.14 mmol) and cesium carbonate (685 mg, 2.10 mmol) in toluene (15 mL) and DMF (1 mL) were heated in a microwave at 115° C. for 1 h. The cold reaction mixture was diluted with EtOAc, washed with water, filtered, and evaporated to give a brown solid. The crude product was added to a silica gel column, and was eluted with 20-100% EtOAc in heptane to give the title compound (407 mg) as a pale yellow solid.

$^1$H NMR (500 MHz, CDCl$_3$) δ 2.36 (s, 3H), 4.06-4.11 (m, 2H), 4.2-4.27 (m, 2H), 4.38 (s, 2H), 6.39 (d, 1H), 6.65 (d, 1H), 7.66 (t, 1H), 7.75 (d, 1H).

m/z (ES+), [M+H]$^+$=291; pH10, HPLC t$_R$ 0.87 min.

Intermediate 91

3-{6-[(4-Methyl-1,3-thiazol-2-yl)amino]pyridin-2-yl}-1,3-oxazinan-2-one

This compound was prepared following the same method as Intermediate 90 but using Intermediate 74.
$^1$H NMR (500 MHz, CDCl$_3$) δ 2.26 (p, 2H), 2.34 (s, 3H), 4.20 (t, 2H), 4.39-4.5 (m, 2H), 6.38 (s, 1H), 6.53 (d, 1H), 7.53 (d, 1H), 7.60 (t, 1H).

m/z (ES+), [M+H]$^+$=291; pH10, HPLC t$_R$ 0.86 min.

Intermediate 92

Benzyl 4-{6-[(5-{2-[(1S)-1-cyclopropylethyl]-7-(methylsulfamoyl)-1-oxo-2,3-dihydro-1H-isoindol-5-yl}-4-methyl-1,3-thiazol-2-yl)amino]pyridin-2-yl}-3-oxopiperazine-1-carboxylate 6-(2-Amino-4-methyl-1,3-thiazol-5-yl)-2-[(1S)-1-cyclopropylethyl]-N-methyl-3-oxo-2,3-dihydro-1H-isoindole-4-sulfonamide (Intermediate 32, 150 mg, 0.37 mmol), benzyl 4-(6-bromopyridin-2-yl)-3-oxopiperazine-1-carboxylate (Intermediate 53, 288 mg, 0.74 mmol), Xantphos (64.1 mg, 0.11 mmol), 2nd Generation XantPhos precatalyst (65.6 mg, 0.07 mmol) and Na$_2$CO$_3$ (117 mg, 1.11 mmol) were mixed in DMF (5 mL) and sealed into a microwave tube. The reaction was heated to 130° C. for 2.5 h in the microwave reactor and cooled to rt. The crude product was purified by flash silica chromatography, elution gradient 0 to 3% MeOH in DCM. Pure fractions were evaporated to dryness to afford the title compound (160 mg) as a pale yellow solid.

m/z (ES+), [M+H]$^+$=716; acid, HPLC t$_R$=1.53 min.

Intermediate 93

Benzyl 4-{6-[(5-{2-[(1S)-1-cyclopropylethyl]-7-(methylsulfonyl)-1-oxo-2,3-dihydro-1H-isoindol-5-yl}-4-methyl-1,3-thiazol-2-yl)amino]pyridin-2-yl}-3-oxopiperazine-1-carboxylate Prepared by the same general method as described for Intermediate 92 using Intermediates 33 & 53.
m/z (ES+), [M+H]$^+$=701; acid, HPLC t$_R$=1.48 min.

Intermediate 94

Benzyl 4-{6-[(5-{2-[(1S)-1-cyclopropylethyl]-7-(ethylsulfamoyl)-1-oxo-2,3-dihydro-1H-isoindol-5-yl}-4-methyl-1,3-thiazol-2-yl)amino]pyridin-2-yl}-3-oxopiperazine-1-carboxylate Prepared by the same general method as described for Intermediate 92 using Intermediates 38 & 53.
m/z (ES+), [M+H]$^+$=730; acid, HPLC t$_R$=2.28 min.

Intermediate 95

Benzyl 4-{6-[(5-{2-[(1S)-1-cyclopropylethyl]-1-oxo-7-(propan-2-ylsulfamoyl)-2,3-dihydro-1H-isoindol-5-yl}-4-methyl-1,3-thiazol-2-yl)amino]pyridin-2-yl}-3-oxopiperazine-1-carboxylate Prepared by the same general method as described for Intermediate 92 using Intermediates 39 & 53.
m/z (ES+), [M+H]$^+$=744; acid, HPLC $t_R$=1.10 min.

Intermediate 96

Benzyl (3R)-4-{6-[(5-{2-[(1S)-1-cyclopropylethyl]-7-(methylsulfamoyl)-1-oxo-2,3-dihydro-1H-isoindol-5-yl}-4-methyl-1,3-thiazol-2-yl)amino]pyridin-2-yl}-3-methyl-5-oxopiperazine-1-carboxylate Prepared by the same general method as described for Intermediate 92 using Intermediates 32 & 58.
m/z (ES+), [M+H]$^+$=730; acid, HPLC $t_R$=1.58 min.

Intermediate 97

Benzyl (3S)-4-{6-[(5-{2-[(1S)-1-cyclopropylethyl]-7-(methylsulfamoyl)-1-oxo-2,3-dihydro-1H-isoindol-5-yl}-4-methyl-1,3-thiazol-2-yl)amino]pyridin-2-yl}-3-methyl-5-oxopiperazine-1-carboxylate Prepared by the same general method as described for Intermediate 92 using Intermediates 32 & 59.

Intermediate 98

Benzyl (2S)-4-{6-[(5-{2-[(1S)-1-cyclopropylethyl]-7-(methylsulfamoyl)-1-oxo-2,3-dihydro-1H-isoindol-5-yl}-4-methyl-1,3-thiazol-2-yl)amino]pyridin-2-yl}-2-methyl-5-oxopiperazine-1-carboxylate Prepared by the same general method as described for Intermediate 92 using Intermediates 32 & 62.
m/z (ES+), [M+H]$^+$=730; acid, HPLC $t_R$=1.61 min.

Intermediate 99

Benzyl (2S)-4-{6-[(5-{2-[(1S)-1-cyclopropylethyl]-7-(methylsulfamoyl)-1-oxo-2,3-dihydro-1H-isoindol-5-yl}-4-methyl-1,3-thiazol-2-yl)amino]pyridin-2-yl}-2-methyl-5-oxopiperazine-1-carboxylate Prepared by the same general method as described for Intermediate 92 using Intermediates 32 & 56.
m/z (ES+), [M+H]$^+$=730; acid, HPLC $t_R$=1.57 min.

Intermediate 100

Benzyl (2R)-4-{6-[(5-{2-[(1S)-1-cyclopropylethyl]-7-(methylsulfamoyl)-1-oxo-2,3-dihydro-1H-isoindol-5-yl}-4-methyl-1,3-thiazol-2-yl)amino]pyridin-2-yl}-2-methyl-3-oxopiperazine-1-carboxylate Prepared by the same general method as described for Intermediate 92 using Intermediates 32 & 54.
m/z (ES+), [M+H]$^+$=730; acid, HPLC $t_R$=1.57 min.

Intermediate 101

Benzyl (2S)-4-{6-[(5-{2-[(1S)-1-cyclopropylethyl]-7-(methylsulfamoyl)-1-oxo-2,3-dihydro-1H-isoindol-5-yl}-4-methyl-1,3-thiazol-2-yl)amino]pyridin-2-yl}-2-methyl-3-oxopiperazine-1-carboxylate Prepared by the same general method as described for Intermediate 92 using Intermediates 32 & 55.
m/z (ES+), [M+H]$^+$=730; acid, HPLC $t_R$=1.22 min.

Intermediate 102

Benzyl 4-{6-[(5-{2-[(1S)-1-cyclopropylethyl]-7-(methylsulfamoyl)-1-oxo-2,3-dihydro-1H-isoindol-5-yl}-4-methyl-1,3-thiazol-2-yl)amino]pyridin-2-yl}-2,2-dimethyl-5-oxopiperazine-1-carboxylate Prepared by the same general method as described for Intermediate 92 using Intermediates 32 & 57.

Intermediate 103

Benzyl 4-{6-[(5-{2-[(1S)-1-cyclopropylethyl]-7-(methylsulfamoyl)-1-oxo-2,3-dihydro-1H-isoindol-5-yl}-4-methyl-1,3-thiazol-2-yl)amino]pyridin-2-yl}-2,2-dimethyl-3-oxopiperazine-1-carboxylate Prepared by the same general method as described for Intermediate 92 using Intermediates 32 & 63.
m/z (ES+), [M+H]$^+$=744; TFA, HPLC $t_R$=0.38 min.

Intermediate 104 tert-Butyl 4-{6-[(5-{2-[(1S)-1-cyclopropylethyl]-7-(methylsulfamoyl)-1-oxo-2,3-dihydro-1H-isoindol-5-yl}-4-methyl-1,3-thiazol-2-yl)amino]pyridin-2-yl}-3-oxo-1,4-diazepane-1-carboxylate Prepared by the same general method as described for Intermediate 92 using Intermediates 32 & 64.
m/z (ES+), [M+H]$^+$=696; acid, HPLC $t_R$=1.18 min.

Intermediate 105 tert-Butyl 4-{6-[(5-{2-[(1S)-1-cyclopropylethyl]-7-(methylsulfamoyl)-1-oxo-2,3-dihydro-1H-isoindol-5-yl}-4-methyl-1,3-thiazol-2-yl)amino]pyridin-2-yl}-5-oxo-1,4-diazepane-1-carboxylate Prepared by the same general method as described for Intermediate 92 using Intermediates 32 & 65.
m/z (ES+), [M+H]$^+$=696; acid, HPLC $t_R$=1.58 min.

Intermediate 106

6-[2-({6-[4-(2-{[tert-Butyl(dimethyl)silyl]oxy}ethyl)-2-oxopiperazin-1-yl]pyridin-2-yl}amino)-4-methyl-1,3-thiazol-5-yl]-2-[(1S)-1-cyclopropylethyl]-N-methyl-3-oxo-2,3-dihydro-1H-isoindole-4-sulfonamide Prepared by the same general method as described for Intermediate 92 using Intermediates 32 & 61.

Intermediate 107

6-[2-({6-[(3R)-3-{[tert-Butyl(dimethyl)silyl]oxy}-2-oxopyrrolidin-1-yl]pyridin-2-yl}amino)-4-methyl-1,3-thiazol-5-yl]-2-[(1S)-1-cyclopropylethyl]-N-methyl-3-oxo-2,3-dihydro-1H-isoindole-4-sulfonamide Prepared by the same general method as described for Intermediate 92 using Intermediates 32 & 71.

m/z (ES+), [M+H]$^+$=697.6; acid, HPLC $t_R$=1.37 min.

Intermediate 108

6-[2-({6-[(3S)-3-{[tert-Butyl(dimethyl)silyl]oxy}-2-oxopyrrolidin-1-yl]pyridin-2-yl}amino)-4-methyl-1,3-thiazol-5-yl]-2-[(1S)-1-cyclopropylethyl]-N-methyl-3-oxo-2,3-dihydro-1H-isoindole-4-sulfonamide Prepared by the same general method as described for Intermediate 92 using Intermediates 32 & 70.

$^1$H NMR (400 MHz, DMSO-d$_6$) δ 0.14 (s, 3H), 0.15 (s, 3H), 0.28-0.31 (m, 1H), 0.41-0.48 (m, 2H), 0.59-0.64 (m, 1H), 0.91 (s, 9H), 1.17-1.20 (m, 2H), 1.33 (d, 3H), 1.92-1.97 (m, 1H), 2.46 (s, 3H), 2.53 (s, 3H), 3.63-3.67 (m, 1H), 3.97-4.03 (m, 1H), 4.28 (t, 1H), 4.67 (t, 1H), 4.76 (s, 2H), 6.80 (d, 1H), 7.55-7.65 (m, 2H), 7.75 (t, 1H), 7.88-7.98 (m, 3H), 11.62 (s, 1H).

m/z (ES+), [M+H]$^+$=697.3; TFA, HPLC $t_R$=1.47 min.

Intermediate 109

6-[2-({6-[(4R)-4-{[tert-Butyl(dimethyl)silyl]oxy}-2-oxopyrrolidin-1-yl]pyridin-2-yl}amino)-4-methyl-1,3-thiazol-5-yl]-2-[(1S)-1-cyclopropylethyl]-N-methyl-3-oxo-2,3-dihydro-1H-isoindole-4-sulfonamide Prepared by the same general method as described for Intermediate 92 using Intermediates 32 & 69.

$^1$H NMR (400 MHz, CDCl$_3$) δ 0.04 (s, 3H), 0.05 (s, 3H), 0.26-0.31 (m, 1H), 0.42-0.45 (m, 2H), 0.60-0.65 (m, 1H), 0.74 (s, 9H), 1.16-1.18 (m, 1H), 1.33 (d, 3H), 2.39 (dd, 1H), 2.44 (s, 3H), 3.04 (dd, 1H), 3.66-3.71 (m, 1H), 4.22 (d, 1H), 4.38 (dd, 1H), 4.59-4.63 (m, 1H), 4.74 (s, 2H), 5.77 (s, 1H), 6.79 (d, 1H), 7.55-7.63 (m, 2H), 7.75 (t, 1H), 7.94 (m, 3H), 11.61 (s, 1H). (1H obscured).

m/z (ES+), [M+H]$^+$=697.35; TFA, HPLC $t_R$=1.28 min.

Intermediate 110

6-[2-({6-[(2S)-2-({[tert-Butyl(dimethyl)silyl]oxy}methyl)-5-oxopyrrolidin-1-yl]pyridin-2-yl}amino)-4-methyl-1,3-thiazol-5-yl]-2-[(1S)-1-cyclopropylethyl]-N-methyl-3-oxo-2,3-dihydro-1H-isoindole-4-sulfonamide Prepared by the same general method as described for Intermediate 92 using Intermediates 32 & 67.

m/z (ES+), [M+H]$^+$=711.35; TFA, HPLC $t_R$=1.31 min.

Intermediate 111

6-[2-({6-[(2R)-2-({[tert-Butyl(dimethyl)silyl]oxy}methyl)-5-oxopyrrolidin-1-yl]pyridin-2-yl}amino)-4-methyl-1,3-thiazol-5-yl]-2-[(1S)-1-cyclopropylethyl]-N-methyl-3-oxo-2,3-dihydro-1H-isoindole-4-sulfonamide Prepared by the same general method as described for Intermediate 92 using Intermediates 32 & 68.

m/z (ES+), [M+H]$^+$=711.35; TFA, HPLC $t_R$=1.31 min.

Intermediate 112

6-[2-({6-[(3S)-3-{[tert-Butyl(dimethyl)silyl]oxy}-2-oxopyrrolidin-1-yl]pyridin-2-yl}amino)-4-methyl-1,3-thiazol-5-yl]-3-oxo-N-(propan-2-yl)-2-[(2S)-1,1,1-trifluoropropan-2-yl]-2,3-dihydro-1H-isoindole-4-sulfonamide Prepared by the same general method as described for Intermediate 92 using Intermediates 39 & 68.

$^1$H NMR (400 MHz, DMSO-d$_6$) δ 0.15 (s, 3H), 0.15 (s, 3H), 0.91 (s, 9H), 0.97 (d, 3H), 1.05 (d, 3H), 1.55 (d, 3H), 1.93-1.98 (m, 1H), 2.48 (s, 3H), 3.99-4.04 (m, 1H), 4.30 (t, 1H), 4.63-4.68 (m, 2H), 4.86 (d, 1H), 5.13 (p, 1H), 6.81 (d, 1H), 7.26 (d, 1H), 7.75 (t, 1H), 7.89 (d, 1H), 7.99 (d, 1H), 8.00 (d, 1H), 11.63 (s, 1H). (2H obscured).

m/z (ES+), [M+H]$^+$=753.5; FA, HPLC $t_R$=2.03 min.

Intermediate 113 tert-Butyl 3-(6-bromopyridin-2-yl)-2-oxoimidazolidine-1-carboxylate

A solution of di-t-butyldicarbonate (748 mL) was added slowly to N,N-dimethylpyridin-4-amine (757 mg) and 1-(6-bromopyridin-2-yl)imidazolidin-2-one (Intermediate 75, 750 mg) in DCM (10 mL). The resulting mixture was stirred at 20° C. for 10 h.

The reaction mixture was diluted with DCM (25 mL). The aqueous layer was separated and re-extracted with DCM (25 mL). The organic layers were combined, dried over Na$_2$SO$_4$, filtered and evaporated to afford crude product that was purified by flash silica chromatography, elution gradient 0 to 10% EtOAc in petroleum ether, to give the subtitle compound (1.0 g) as a white solid.

$^1$H NMR (400 MHz, DMSO-d$_6$) δ 1.49 (s, 9H), 3.77-3.81 (m, 2H), 3.87-3.91 (m, 2H), 7.34 (d, 1H), 7.75 (t, 1H), 8.17 (d, 1H).

m/z (ES+), [M+H]$^+$=342.0; TFA, HPLC $t_R$=1.41 min.

Intermediate 114 tert-Butyl 3-{6-[(4-methyl-5-{7-(methylsulfamoyl)-1-oxo-2-[(2S)-1,1,1-trifluoropropan-2-yl]-2,3-dihydro-1H-isoindol-5-yl}-1,3-thiazol-2-yl)amino]pyridin-2-yl}-2-oxoimidazolidine-1-carboxylate Prepared by the same general method as described for Intermediate 92 using Intermediates 37 & 113.

$^1$H NMR (400 MHz, DMSO-d$_6$) δ 1.50 (s, 9H), 1.54 (d, 3H), 2.47 (s, 3H), 2.54 (d, 3H), 3.86 (dd, 2H), 4.21 (dd, 2H), 4.64 (d, 1H), 4.84 (d, 1H), 5.12 (p, 1H), 6.74-6.76 (m, 1H), 7.18 (q, 1H), 7.72-7.73 (m, 2H), 7.97 (d, 1H), 7.99 (d, 1H), 11.60 (s, 1H).

m/z (ES+), [M+H]$^+$=696.4; FA, HPLC $t_R$=1.42 min.

Intermediate 115

1-(6-((4-Methylthiazol-2-yl)amino)pyridin-2-yl)pyrrolidin-2-one

This compound was prepared following the same method as Intermediate 90 but using Intermediate 66

$^1$H NMR (400 MHz, DMSO-d$_6$) δ 2.02-2.13 (m, 2H), 2.23 (s, 3H), 2.57 (t, 2H), 4.19 (t, 2H), 6.57 (s, 1H), 6.70 (d, 1H), 7.66 (t, 1H), 7.79 (d, 1H), 11.18 (s, 1H).

m/z (ES+), [M+H]$^+$=275; pH3, HPLC t$_R$=1.23 min.

Intermediate 116

2,4-Dichloro-6-[[[(1S)-1-cyclopropylethyl]amino]methyl]phenol 3,5-Dichloro-2-hydroxybenzaldehyde (16.10 g) was dissolved in methanol (322 mL). (S)-1-cyclopropylethylamine (9.62 mL) was added and the mixture was stirred at ambient temperature for 1 h and the mixture was then cooled to 0° C. After 15 min sodium borohydride (1.276 g) was added in portions over 10 min. Once addition was complete the reaction was allowed to warm to ambient temperature. Water (644 mL) was added, the mixture was stirred for 1 h and then the solid was collected and washed with further water to give the title compound (20.02 g) as a white solid.

m/z (ES+), [M+H]$^+$=260/262; CAL, HPLC t$_R$=2.91 min $^1$H NMR (500 MHz, CDCl$_3$, 27° C.) 0.06-0.15 (1H, m), 0.21-0.32 (1H, m), 0.46-0.63 (2H, m), 0.69-0.82 (1H, m), 1.23 (3H, d), 1.89-2.13 (1H, m), 3.95-4.15 (2H, m), 6.87 (1H, dd), 7.23 (1H, d).

$^{13}$C NMR (126 MHz, CDCl$_3$, 27° C.) 153.0, 128.0, 125.9, 124.9, 122.8, 121.4, 57.9, 49.5, 19.8, 16.8, 4.5, 1.7.

Intermediate 117

[2,4-Dichloro-6-[[[(1S)-1-cyclopropylethyl]amino]methyl]phenyl]trifluoromethanesulfonate trifluorosulfonic acid salt 2,4-Dichloro-6-[[[(1S)-1-cyclopropylethyl]amino]methyl]phenol (intermediate 116, 2.54 g) was dissolved in dichloromethane (51 mL). Trifluoromethanesulfonic anhydride (1.73 mL) was added and the reaction mixture was stirred for 75 min. Heptane (50 mL) was added and the resulting solid was collected to give the title compound (4.54 g) as a white solid.

m/z (ES+), [M+H]$^+$=392/394; CAL, HPLC t$_R$=5.03 min $^1$H NMR (400 MHz, DMSO-d$_6$, 27° C.) 0.27-0.37 (1H, m), 0.49-0.57 (1H, m), 0.66 (2H, dddd), 0.91-1.04 (1H, m), 1.35 (3H, d), 2.77 (1H, s), 4.25-4.53 (2H, m), 7.95 (1H, d), 8.16 (1H, d), 8.91 (2H, s).

$^{19}$F NMR (376 MHz, DMSO-d$_6$, 27° C.) −77.78, −71.97.

$^{13}$C NMR (101 MHz, DMSO-d$_6$, 27° C.) 141.7, 134.5, 132.2, 131.3, 130.4, 128.6, 123.2, 120.0, 116.8, 113.6, 60.0, 42.5, 17.7, 13.6, 6.0, 2.5.

Intermediate 118

5,7-Dichloro-2-[(1 S)-1-cyclopropylethyl]-2,3-dihydro-1H-isoindol-1-one

[2,4-Dichloro-6-[[[(1S)-1-cyclopropylethyl]amino]methyl]phenyl]trifluoromethanesulfonate trifluorosulfonic acid salt (Intermediate 117, 9.00 g) and 1,3-bis(diphenylphosphino)propane (377 mg), palladium (II) acetate (184 mg) were dissolved in MeCN (72 mL). Triethylamine (7.52 mL) was added. The vessels were placed under an atmosphere of carbon monoxide (2 bar) and the mixtures were heated to 45° C. for 16 h. The reaction mixture was allowed to cool and solvent was evaporated. TBME (41 mL) was added and the solution was washed with water (36 mL, 3×18 mL). Ethanol (18 mL) was added and solvent was distilled off to leave ca 20 mL total volume. Ethanol (45 mL) was added and solvent was distilled off to leave a total volume of 32 mL. Ethanol (13 mL) was added followed by water (68 mL) over 10 minutes. The mixture was stirred for a further 10 min and then the precipitated solid was collected and washed with water twice to give the title compound (3.57 g) as a yellow solid. m/z (ES+), [M+H]$^+$=270/272; CAL, HPLC t$_R$=3.58 min $^1$H NMR (400 MHz, DMSO-d$_6$, 27° C.) 0.19-0.28 (1H, m), 0.33-0.45 (2H, m), 0.49-0.64 (1H, m), 1.04-1.17 (1H, m), 1.27 (3H, d), 3.55 (1H, dq), 4.53 (2H, s), 7.64 (1H, d), 7.69-7.72 (1H, m).

$^{13}$C NMR (126 MHz, DMSO-d$_6$, 27° C.) 163.5, 146.3, 136.4, 130.3, 128.9, 127.4, 122.9, 51.8, 45.0, 18.0, 15.5, 3.9, 3.4.

Intermediate 119

5-Chloro-2-[(1S)-1-cyclopropylethyl]-7-(methylsulfanyl)-2,3-dihydro-1H-isoindol-1-one 5,7-Dichloro-2-[(1S)-1-cyclopropylethyl]-2,3-dihydro-1H-isoindol-1-one (Intermediate 118, 0.65 g) was dissolved in dioxan (6.5 mL) and degassed thoroughly. Sodium thiomethoide (0.19 g) was added and the flask was again degassed. The solution was heated to reflux for 7 h and then allowed to cool. Water (13 mL) was added and the resulting suspension was cooled on ice for 1 h and then filtered. The collected solid was dried to give the title compound (0.66 g).

m/z (ES+), [M+H]$^+$=282/284; CAL, HPLC t$_R$=3.75 min $^1$H NMR (400 MHz, DMSO-d$_6$, 27° C.) 0.15-0.27 (1H, m), 0.31-0.45 (2H, m), 0.5-0.6 (1H, m), 1.02-1.15 (1H, m), 1.25 (3H, d), 2.46 (3H, s), 3.45-3.55 (1H, m), 4.50 (2H, s), 7.20 (1H, d), 7.38 7.41 (1H, m).

$^{13}$C NMR (126 MHz, DMSO-d$_6$, 27° C.) 165.7, 144.8, 140.0, 136.6, 126.6, 121.8, 118.7, 51.5, 45.4, 18.0, 15.6, 13.1, 3.8, 3.3.

Intermediate 119 Alternative Preparation

Followed the same general method as used for Intermediate 119 above but starting with 5-chloro-2-[(1S)-1-cyclopropylethyl]-7-fluoro-isoindolin-1-one (105 mg) to give the title compound (110 mg) as an off-white solid $^1$H NMR (400 MHz, DMSO-d$_6$, 27° C.) 0.15-0.27 (1H, m), 0.31-0.45 (2H, m), 0.5-0.6 (1H, m), 1.02-1.15 (1H, m), 1.25 (3H, d), 2.46 (3H, s), 3.45-3.55 (1H, m), 4.50 (2H, s), 7.20 (1H, d), 7.38 7.41 (1H, m).

$^{13}$C NMR (126 MHz, DMSO-d$_6$, 27° C.) 165.7, 144.8, 140.0, 136.6, 126.6, 121.8, 118.7, 51.5, 45.4, 18.0, 15.6, 13.1, 3.8, 3.3.

m/z (ES+), [M+H]$^+$=282/284; CAL, HPLC t$_R$=3.75 min

Intermediate 120

5-Chloro-2-[(1S)-1-cyclopropylethyl]-7-(methylsulfonyl)-2,3-dihydro-1H-isoindol-1-one 5-Chloro-2-[(1 S)-1-cyclopropylethyl]-7-(methylsulfanyl)-2,3-dihydro-1H-isoindol-1-one (Intermediate 119, 0.68 g) was dissolved in ethanol (6.8 mL) and water (0.68 mL) and heated to 50° C. Potassium peroxymonosulfate (2.2 g) and the resulting mixture was stirred for 280 min and then allowed to cool. The reaction was quenched by the addition of a solution of sodium metabisulfite (0.71 g) in water (7 mL) followed by additional water (10 mL). The mixture was stirred and the resulting solid was collected by filtration and dried to give the title compound (0.69 g) as a white solid.

m/z (ES+), [M+H]$^+$=314/316; CAL, HPLC $t_R$=2.89 min $^1$H NMR (500 MHz, DMSO-d$_6$, 27° C.) 0.21-0.33 (1H, m), 0.35-0.49 (2H, m), 0.53-0.63 (1H, m), 1.1-1.21 (1H, m), 1.30 (3H, d), 3.51-3.7 (4H, m), 4.67 (2H, s), 7.94 (1H, d), 8.12 (1H, d).

$^{13}$C NMR (126 MHz, DMSO-d$_6$, 27° C.) 163.1, 147.1, 138.7, 136.0, 128.8, 128.2, 127.1, 52.2, 45.8, 43.0, 17.9, 15.4, 3.84, 3.43.

EXAMPLES

Example 1

2-[(1S)-1-Cyclopropylethyl]-5-(4-methyl-2-{[6-(2-oxopyrrolidin-1-yl)pyridin-2-yl]amino}-1,3-thiazol-5-yl)-7-(methylsulfonyl)-2,3-dihydro-1H-isoindol-1-one

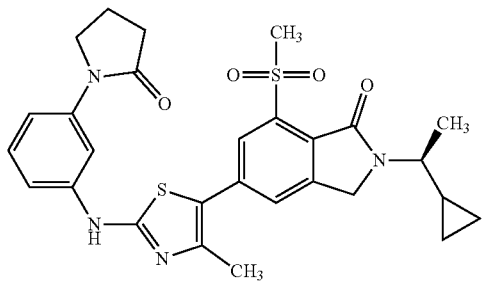 [SMILES: Cc1nc(Nc2cccc(N3CCCC3=O)c2)sc1-c1cc2c(c(S(C)(=O)=O)c1)C(=O)N([C@@H](C)C1CC1)C2]

5-(2-Amino-4-methyl-1,3-thiazol-5-yl)-2-[(1S)-1-cyclopropylethyl]-7-(methylsulfonyl)-2,3-dihydro-1H-isoindol-1-one (Intermediate 33, 150 mg), 1-(6-bromopyridin-2-yl)pyrrolidin-2-one (Intermediate 66, 102 mg), 2$^{nd}$ Generation XantPhos precatalyst (68.1 mg), Xantphos (66.5 mg) and Na$_2$CO$_3$ (122 mg) were mixed in DMF (4 mL) and sealed into a microwave tube. The reaction was heated to 125° C. for 1 h in the microwave reactor and cooled to RT. The solvent was removed under reduced pressure. The crude product was purified by flash silica chromatography, elution gradient 0 to 4% MeOH in CH$_2$Cl$_2$ and then by preparative HPLC (XBridge Prep C18 OBD column, 5 g silica, 19 mm diameter, 150 mm length), using decreasingly polar mixtures of water (containing 0.5% NH$_4$HCO$_3$) and MeCN as eluents to give the title compound (95 mg) as a yellow solid.

$^1$H NMR (400 MHz, DMSO-d$_6$) δ 0.25-0.33 (m, 1H), 0.40-0.47 (m, 2H), 0.59-0.63 (m, 1H), 1.10-1.22 (m, 1H), 1.32 (d, 3H), 2.11 (p, 2H), 2.46 (s, 3H), 2.60 (t, 2H), 3.65 (s, 4H), 4.25 (t, 2H), 4.72 (s, 2H), 6.78 (d, 1H), 7.73 (t, 1H), 7.86 (d, 1H), 8.03 (s, 1H), 8.07 (s, 1H), 11.56 (s, 1H).

m/z (ES+), [M+H]$^+$=552.2; TFA System 2, HPLC $t_R$=1.90 min.

The pure solid residue (69 mg) was suspended in a mixture of ethanol and water (3:1, 1.4 mL) and this suspension was slurried at a range of temperatures as follows: 110° C. (4×30 min allowing to cool to ambient temperature inbetween each time); 110° C. (60 min), 90° C. (60 min), 80° C. (60 min) and then left to cool to ambient temperature overnight. The resultant solid was collected and dried to give the title compound (64 mg) which was found to be crystalline by XRPD and a typical diffractogram is displayed in FIG. 1. Characteristic peak positions are listed below in Tables 1 and 2.

TABLE 1

| Five peaks characteristic for Example 1, form B | |
|---|---|
| °2-theta | Relative intensity |
| 7.9 | vs |
| 12.7 | m |
| 13.6 | m |
| 17.6 | w |
| 22.0 | vs |

TABLE 2

| Peaks characteristic for Example 1, form B | |
|---|---|
| °2-theta | Relative intensity |
| 6.4 | w |
| 7.9 | vs |
| 9.3 | w |
| 9.8 | vw |
| 11.3 | w |
| 12.0 | vw |
| 12.7 | m |
| 13.6 | m |
| 15.8 | w |
| 16.5 | w |
| 17.6 | w |
| 18.4 | vw |
| 18.9 | w |
| 20.5 | vw |
| 21.2 | w |
| 22.0 | vs |
| 22.7 | vw |
| 27.1 | w |
| 28 | w |
| 28.3 | w |
| 29.2 | w |

Example 1, Alternative Method

2-[(1S)-1-Cyclopropylethyl]-5-(4-methyl-2-{[6-(2-oxopyrrolidin-1-yl)pyridin-2-yl]amino}-1,3-thiazol-5-yl)-7-(methylsulfonyl)-2,3-dihydro-1H-isoindol-1-one

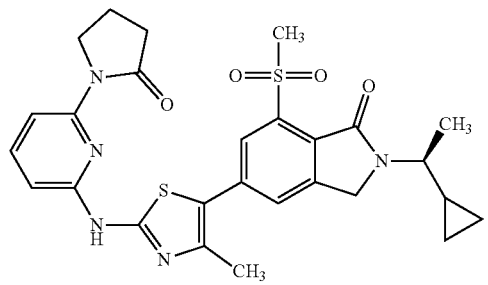 [SMILES: Cc1nc(Nc2cccc(N3CCCC3=O)n2)sc1-c1cc2c(c(S(C)(=O)=O)c1)C(=O)N([C@@H](C)C1CC1)C2]

A 500 mL roundbottomed flask was charged with 5-bromo-2-[(1S)-1-cyclopropylethyl]-7-(methylsulfonyl)-2,3-dihydro-1H-isoindol-1-one (Intermediate 86, 8.88 g), 1-(6-((4-methylthiazol-2-yl)amino)pyridin-2-yl)pyrrolidin-2-one (Intermediate 115, 6.73 g), 1,1'-bis (di-tert-butylphosphino)ferrocene palladium dichloride (0.465 g) and cesium carbonate (17.06 g). DMF (95 mL) was added and the reaction mixture was heated to 75° C. for 2 h 50 min then additional 5-bromo-2-[(1S)-1-cyclopropylethyl]-7-(methylsulfonyl)-2,3-dihydro-1H-isoindol-1-one (228 mg) was added and the mixture was heated for a further hour. The mixture was allowed to cool for 30 min and water (160 mL) was added. The mixture was cooled to 7-8° C., held for 15 min and then the solid was collected, washed twice with water (2×25 mL) and the reddish solid was air dried under suction for two hours. The solid was washed with heptane (100 mL), was then dissolved in 150 mL DCM:MeOH 9:1 and treated with (SiliaMetS Thiol, loading 1.42 mmol/g, 3 g); the suspension was stirred slowly for 1 h whereupon charcoal (3.5 g) was added and stirring was continued overnight.

The mixture was filtered through a pad of silica (eluted with 200 mL DCM:MeOH 9:1) and evaporated to dryness. The resulting solid was suspended in methanol (120 mL) and the suspension was heated to 50° C. overnight. The solid was collected and then suspended in methanol (120 mL) at 50° C. overnight. The solid was collected, washed with methanol (50 mL) and then heptane (50 mL) and was then dissolved in methanol:DCM (1:9, 120 mL). Methanol (120 mL) was added and the volume was reduced to ca 120 mL; the resulting suspension was stirred for 24 h at 50° C. The solid was collected, washed with methanol (50 mL) and dried to give the title compound (10.0 g) as a yellow solid.

Figure 2:
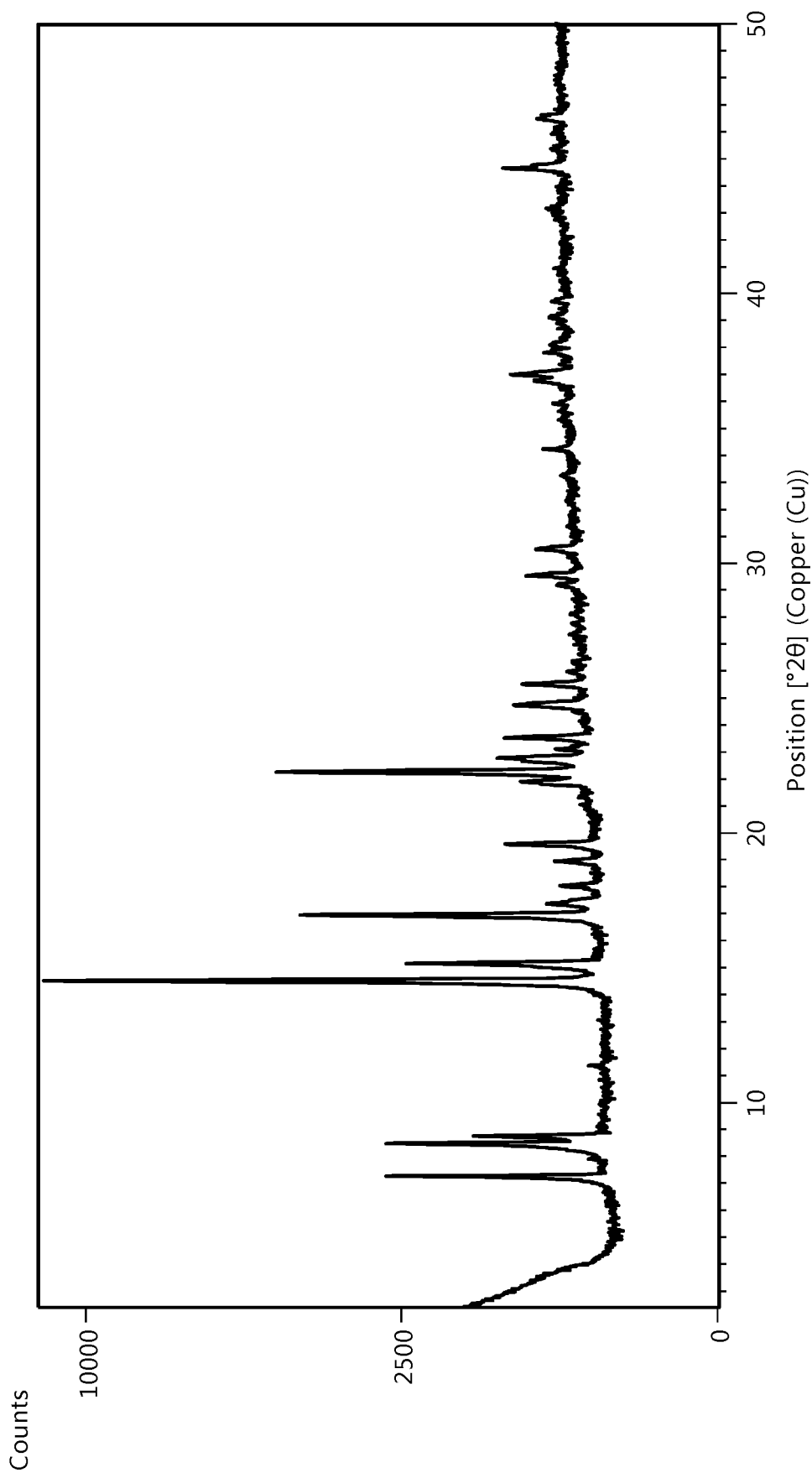
FIG. 2 shows the X-ray powder diffraction pattern for Example 1, form A: 2-[(1S)-1-Cyclopropylethyl]-5-(4-methyl-2-{[6-(2-oxopyrrolidin-1-yl)pyridin-2-yl]amino}-1,3-thiazol-5-yl)-7-(methylsulfonyl)-2,3-dihydro-1H-isoindol-1-one.

The solid product was found to be crystalline by XRPD and a typical diffractogram is displayed in FIG. 2. Characteristic peak positions are listed below in Tables 3 and 4.

TABLE 3

Five peaks characteristic for Example 1, form A

| °2-theta | Relative intensity |
|---|---|
| 8.4 | s |
| 14.5 | s |
| 16.9 | vs |
| 19.5 | m |
| 24.7 | s |

TABLE 4

Peaks characteristic for Example 1, form A

| °2-theta | Relative intensity |
|---|---|
| 7.2 | w |
| 8.4 | s |
| 8.7 | s |
| 11.3 | vw |
| 14.5 | s |
| 15.0 | w |
| 15.1 | m |
| 16.9 | vs |
| 17.3 | m |
| 18.0 | w |
| 18.9 | m |
| 19.5 | m |
| 21.9 | m |
| 22.2 | s |
| 22.7 | s |
| 23.1 | w |
| 23.5 | w |
| 24.7 | s |
| 25.5 | w |

Example 1, Alternative Preparation 2

Cesium carbonate (0.56 g), 1-(6-((4-methylthiazol-2-yl)amino)pyridin-2-yl)pyrrolidin-2-one (Intermediate 115, 0.22 g), 5-Chloro-2-[(1S)-1-cyclopropylethyl]-7-(methylsulfonyl)-2,3-dihydro-1H-isoindol-1-one (Intermediate 120, 0.25 g) and Pd-118 (0.015 g) were combined in DMF (2.5 mL) and the mixture was degassed thoroughly. The mixture was heated to 85° C. for 140 min and then allowed to cool. Water (5 mL) was added and the mixture was stirred for 75 min before the precipitated solid was collected to give the title compound as a yellow solid.

Example 2

N-{6-[(5-{2-[(1S)-1-Cyclopropylethyl]-7-(methylsulfonyl)-1-oxo-2,3-dihydro-1H-isoindol-5-yl}-4-methyl-1,3-thiazol-2-yl)amino]pyridin-2-yl}acetamide

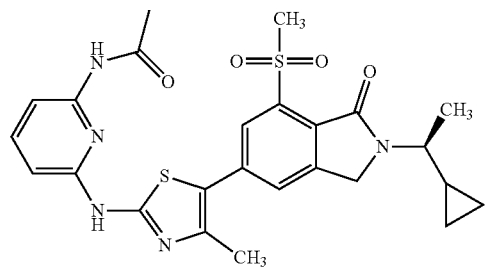 [SMILES: CC(=O)Nc1cccc(Nc2nc(C)c(-c3cc4c(c(S(C)(=O)=O)c3)C(=O)N([C@@H](C)C3CC3)C4)s2)n1]

Prepared by the same general method as described for Example 1 using Intermediate 33 and N-(6-bromo-2-pyridyl)acetamide.

¹H NMR (400 MHz, DMSO-d₆) δ 0.27-0.32 (m, 1H), 0.39-0.49 (m, 2H), 0.56-0.66 (m, 1H), 1.14-1.22 (m, 1H), 1.33 (d, 3H), 2.18 (s, 3H), 2.43 (s, 3H), 3.58-3.68 (m, 4H), 4.73 (s, 2H), 6.76 (dd, 1H), 7.64-7.70 (m, 2H), 8.05 (s, 1H), 8.09 (s, 1H), 10.07 (s, 1H), 11.43 (s, 1H).

m/z (ES+), [M+H]⁺=526.2; TFA, HPLC $t_R$=1.74 min.

Example 3

N-{6-[(5-{2-[(1S)-1-Cyclopropylethyl]-7-(methylsulfonyl)-1-oxo-2,3-dihydro-1H-isoindol-5-yl}-4-methyl-1,3-thiazol-2-yl)amino]pyridin-2-yl}-N-methylacetamide

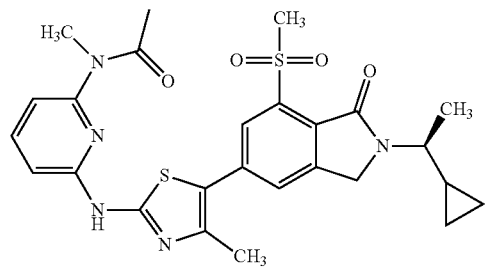 [SMILES: CC(=O)N(C)c1cccc(Nc2nc(C)c(-c3cc4c(c(S(C)(=O)=O)c3)C(=O)N([C@@H](C)C3CC3)C4)s2)n1]

Prepared by the same general method as described for Example 1 using Intermediate 33 and N-(6-bromo-2-pyridyl)-N-methyl-acetamide.

¹H NMR (400 MHz, DMSO-d₆) δ 0.26-0.31 (m, 1H), 0.39-0.48 (m, 2H), 0.55-0.66 (m, 1H), 1.13-1.19 (m, 1H), 1.32 (d, 3H), 2.10 (s, 3H), 2.45 (s, 3H), 3.37 (m, 3H), 3.60-3.67 (m, 4H), 4.72 (s, 2H), 6.96 (d, 1H), 7.05 (d, 1H), 7.80 (t, 1H), 8.01 (s, 1H), 8.04 (s, 1H), 11.70 (s, 1H).

m/z (ES+), [M+H]⁺=540.3; TFA system 2, HPLC $t_R$=1.79 min.

Example 4

2-[(1S)-1-Cyclopropylethyl]-5-(4-methyl-2-{[6-(2-oxopiperidin-1-yl)pyridin-2-yl]amino}-1,3-thiazol-5-yl)-7-(methylsulfonyl)-2,3-dihydro-1H-isoindol-1-one

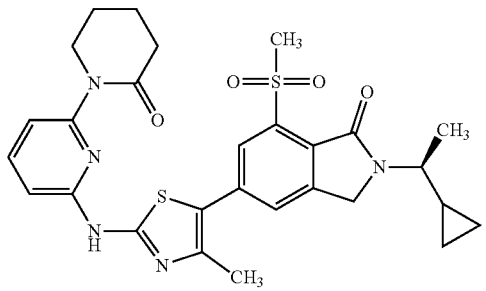 [SMILES: Cc1nc(Nc2cccc(N3CCCCC3=O)n2)sc1-c1cc2c(c(S(C)(=O)=O)c1)C(=O)N([C@@H](C)C1CC1)C2]

Prepared by the same general method as described for Example 1 using Intermediate 33 and Intermediate 73.

¹H NMR (300 MHz, DMSO-d₆) δ 0.24-0.33 (m, 1H), 0.36-0.51 (m, 2H), 0.57-0.63 (m, 1H), 1.15-1.18 (m, 1H), 1.32 (d, 3H), 1.83-2.00 (m, 4H), 2.51 (s, 3H), 2.51-2.52 (m, 2H), 3.60-3.64 (m, 4H), 4.06 (t, 2H), 4.72 (s, 2H), 6.85 (d, 1H), 7.31 (d, 1H), 7.73 (t, 1H), 8.05 (s, 1H), 8.06 (s, 1H), 11.62 (s, 1H).

m/z (ES+), [M+H]⁺=566.2; acid, HPLC $t_R$=1.87 min.

Example 5

2-[(1S)-1-Cyclopropylethyl]-5-(4-methyl-2-{[6-(3-methyl-2-oxoimidazolidin-1-yl)pyridin-2-yl]amino}-1,3-thiazol-5-yl)-7-(methylsulfonyl)-2,3-dihydro-1H-isoindol-1-one

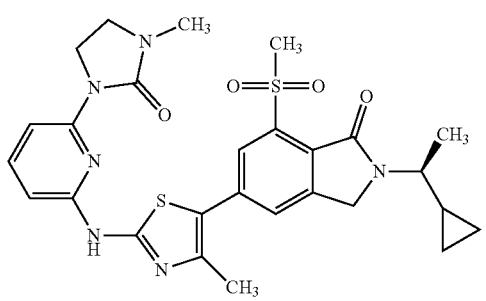 [SMILES: Cc1nc(Nc2cccc(N3CCN(C)C3=O)n2)sc1-c1cc2c(c(S(C)(=O)=O)c1)C(=O)N([C@@H](C)C1CC1)C2]

Prepared by the same general method as described for Example 1 using Intermediate 33 and Intermediate 51.

¹H NMR (500 MHz, DMSO-d₆) δ 0.25-0.30 (m, 1H), 0.38-0.47 (m, 2H), 0.57-0.64 (m, 1H), 1.12-1.20 (m, 1H), 1.31 (d, 3H), 2.45 (s, 3H), 2.80 (s, 3H), 3.50 (t, 2H), 3.59-3.67 (m+s, 4H), 4.20 (t, 2H), 4.70 (s, 2H), 6.62 (d, 1H), 7.63 (t, 1H), 7.73 (d, 1H), 8.03 (d, 1H), 8.07 (d, 1H), 11.45 (s, 1H).

m/z (ES+, pH3)=567 (M+H)⁺, HPLC $t_R$=1.99 min.

m/z (ES+), [M+H]⁺=567; acid, HPLC $t_R$=1.87 min.

Example 6

2-[(1S)-1-Cyclopropylethyl]-5-(4-methyl-2-{[6-(2-oxoimidazolidin-1-yl)pyridin-2-yl]amino}-1,3-thiazol-5-yl)-7-(methylsulfonyl)-2,3-dihydro-1H-isoindol-1-one

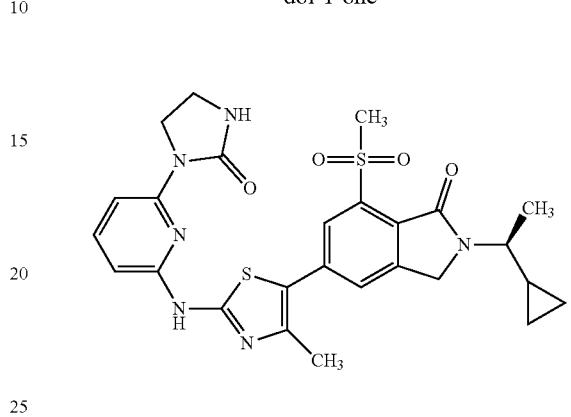

Prepared by the same general method as described for Example 1 using Intermediate 33 and Intermediate 75

¹H NMR (400 MHz, DMSO-d₆) δ 0.22-0.33 (m, 1H), 0.36-0.50 (m, 2H), 0.55-0.68 (m, 1H), 1.14-1.19 (m, 1H), 1.32 (d, 3H), 2.45 (s, 3H), 3.46 (t, 2H), 3.61-3.65 (m, 1H), 3.64 (s, 3H), 4.27 (t, 2H), 4.71 (s, 2H), 6.62 (d, 1H), 7.25 (s, 1H), 7.62 (t, 1H), 7.71 (d, 1H), 8.03 (s, 1H), 8.06 (s, 1H), 11.47 (s, 1H).

m/z (ES+), [M+H]⁺=553; acid, HPLC $t_R$=1.73 min.

Example 7

2-[(1S)-1-Cyclopropylethyl]-5-(4-methyl-2-{[6-(3-oxomorpholin-4-yl)pyridin-2-yl]amino}-1,3-thiazol-5-yl)-7-(methylsulfonyl)-2,3-dihydro-1H-isoindol-1-one

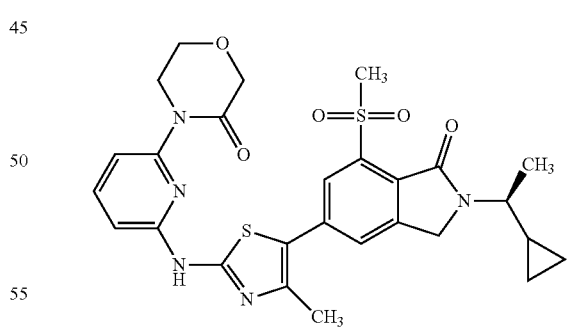

Prepared by the same general method as described for Example 1 using Intermediate 33 and Intermediate 50

¹H NMR (300 MHz, DMSO-d₆) δ 0.25-0.29 (m, 1H), 0.39-0.46 (m, 2H), 0.58-0.62 (m, 1H), 1.14-1.18 (m, 1H), 1.31 (d, 3H), 2.47 (s, 3H), 3.61-3.65 (m, 1H), 3.64 (s, 3H), 4.05-4.09 (m, 2H), 4.16-4.19 (m, 2H), 4.29 (s, 2H), 4.71 (s, 2H), 6.88 (d, 1H), 7.60 (t, 1H), 7.77 (t, 1H), 8.05 (s, 2H), 11.66 (s, 1H).

m/z (ES+), [M+H]⁺=568; acid, HPLC $t_R$=1.83 min.

Example 8

2-[(1S)-1-Cyclopropylethyl]-5-(4-methyl-2-{[6-(2-oxo-1,3-oxazinan-3-yl)pyridin-2-yl]amino}-1,3-thiazol-5-yl)-7-(methylsulfonyl)-2,3-dihydro-1H-isoindol-1-one

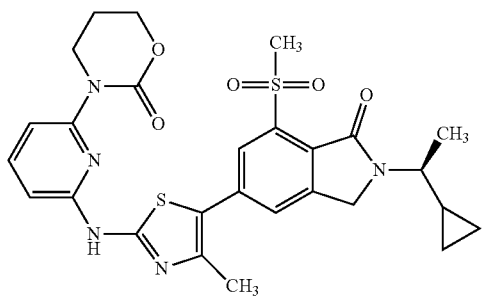 [SMILES: Cc1nc(Nc2cccc(N3CCCOC3=O)n2)sc1-c1cc2c(c(S(C)(=O)=O)c1)C(=O)N([C@@H](C)C1CC1)C2]

Prepared by the same general method as described for Example 1 using Intermediate 33 and Intermediate 74.

$^1$H NMR (400 MHz, DMSO-d$_6$) δ 0.27-0.31 (m, 1H), 0.39-0.48 (m, 2H), 0.55-0.68 (m, 1H), 1.13-1.30 (m, 1H), 1.32 (d, 3H), 2.15-2.26 (m, 2H), 2.48 (s, 3H), 3.61-3.65 (m, 1H), 3.64 (s, 3H), 4.14 (t, 2H), 4.40 (t, 2H), 4.71 (s, 2H), 6.85 (d, 1H), 7.39 (d, 1H), 7.74 (t, 1H), 8.05, (s, 1H), 8.07 (s, 1H), 11.34 (s, 1H).

m/z (ES+), [M+H]$^+$=568; acid, HPLC t$_R$=1.78 min.

Example 9

6-{6-[(5-{2-[(1S)-1-Cyclopropylethyl]-7-(methylsulfonyl)-1-oxo-2,3-dihydro-1H-isoindol-5-yl}-4-methyl-1,3-thiazol-2-yl)amino]pyridin-2-yl}-6,7-dihydro-5H-pyrrolo[3,4-b]pyridin-5-one

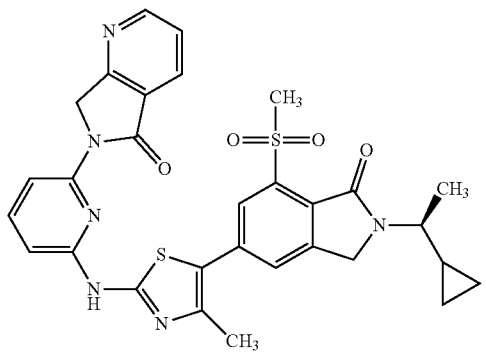 [SMILES: Cc1nc(Nc2cccc(N3Cc4ncccc4C3=O)n2)sc1-c1cc2c(c(S(C)(=O)=O)c1)C(=O)N([C@@H](C)C1CC1)C2]

Prepared by the same general method as described for Example 1 using Intermediate 33 and Intermediate 72.

$^1$H NMR (300 MHz, DMSO-d$_6$) δ 0.28-0.31 (m, 1H), 0.40-0.48 (m, 2H), 0.58-0.64 (m, 1H), 1.16-1.23 (m, 1H), 1.32 (d, 3H), 2.41 (s, 3H), 3.62-3.66 (m, 1H), 3.64 (s, 3H), 4.71 (s, 2H), 5.29 (s, 2H), 6.85 (d, 1H), 7.58 (dd, 1H), 7.81 (t, 1H), 8.06 (m, 3H), 8.22 (dd, 1H), 8.82 (dd, 1H), 11.65 (s, 1H).

m/z (ES+), [M+H]$^+$=601.2; TFA, HPLC t$_R$=1.97 min.

Example 10

5-(4-Methyl-2-{[6-(2-oxopyrrolidin-1-yl)pyridin-2-yl]amino}-1,3-thiazol-5-yl)-7-(methylsulfonyl)-2-[(2S)-1,1,1-trifluoropropan-2-yl]-2,3-dihydro-1H-isoindol-1-one

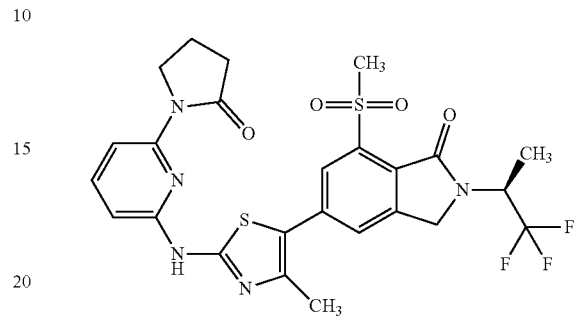

Prepared by the same general method as described for Example 1 using Intermediate 34 and Intermediate 66

$^1$H NMR (500 MHz, DMSO-d$_6$) δ 1.52 (d, 3H), 2.11 (p, 2H), 2.47 (s, 3H), 2.60 (t, 2H), 3.61 (s, 3H), 4.25 (t, 2H), 4.61 (d, 1H), 4.81 (d, 1H), 5.07-5.13 (m, 1H), 6.78 (d, 1H), 7.73 (t, 1H), 7.86 (d, 1H), 8.06 (d, 1H), 8.10 (d, 1H), 11.59 (s, 1H).

m/z (ES+), [M+H]$^+$=580.1; acid, HPLC t$_R$=1.94 min.

Figure 3:
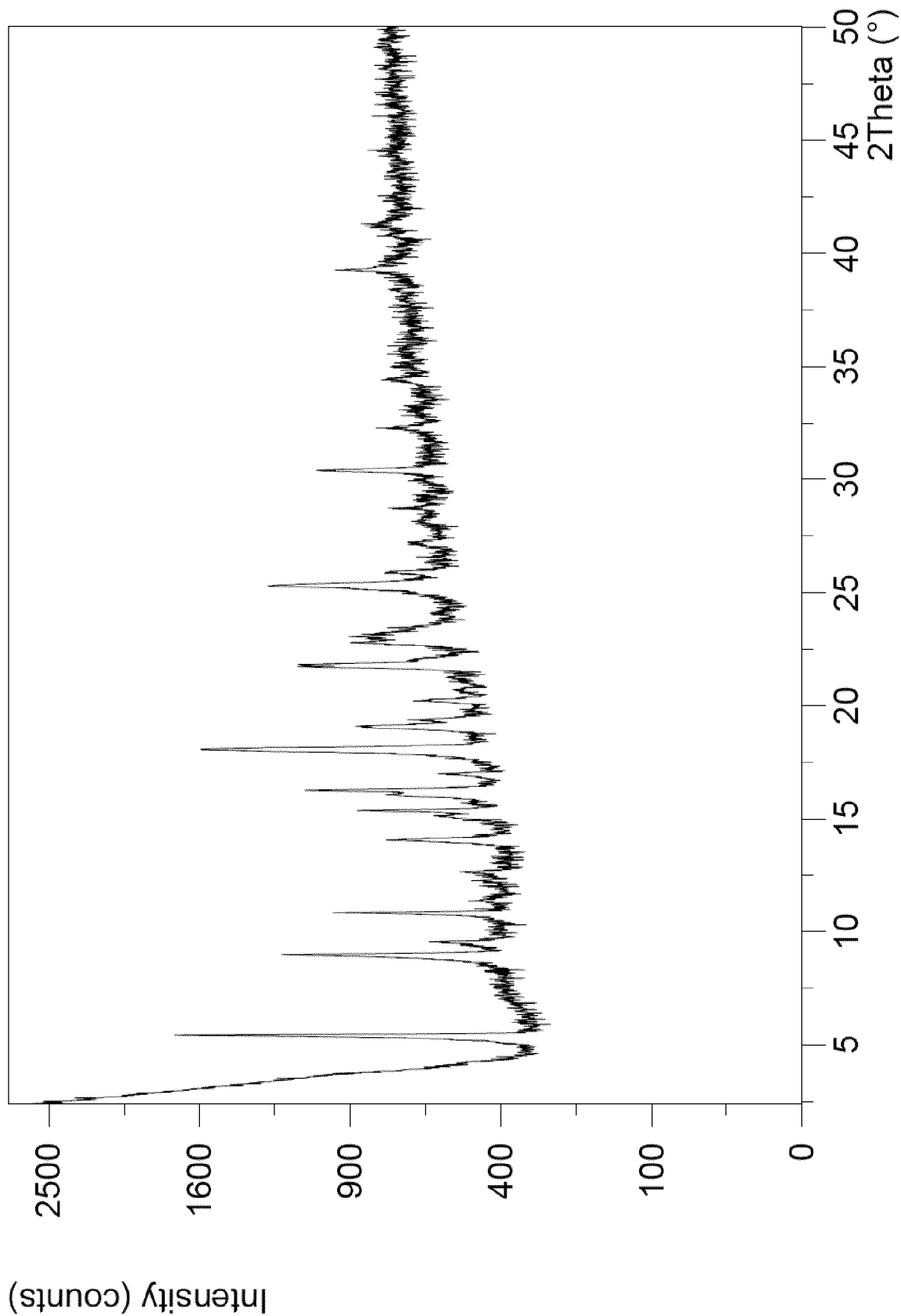
FIG. 3 shows the X-ray powder diffraction pattern for Example 10: 5-(4-Methyl-2-{[6-(2-oxopyrrolidin-1-yl)pyridin-2-yl]amino}-1,3-thiazol-5-yl)-7-(methylsulfonyl)-2-[(2S)-1,1,1-trifluoropropan-2-yl]-2,3-dihydro-1H-isoindol-1-one.

The solid residue was found to be crystalline by XRPD and a typical diffractogram is displayed in FIG. 3. Characteristic peak positions are listed below in Tables 5 and 6.

TABLE 5

Five peaks characteristic for Example 10

| °2-theta | Relative intensity |
|---|---|
| 5.4 | vs |
| 9.0 | s |
| 10.8 | s |
| 16.3 | s |
| 18.1 | vs |

TABLE 6

Peaks characteristic for Example 10

| °2-theta | Relative intensity |
|---|---|
| 5.4 | vs |
| 9 | s |
| 9.5 | w |
| 10.8 | s |
| 14.1 | m |
| 15.4 | s |
| 16.1 | m |
| 16.3 | s |
| 18.1 | vs |
| 19.1 | m |
| 20.2 | m |
| 21.8 | s |
| 25.3 | s |
| 30.4 | s |

Example 11

5-(4-Methyl-2-{[6-(2-oxoimidazolidin-1-yl)pyridin-2-yl]amino}-1,3-thiazol-5-yl)-7-(methylsulfonyl)-2-[(2S)-1,1,1-trifluoropropan-2-yl]-2,3-dihydro-1H-isoindol-1-one

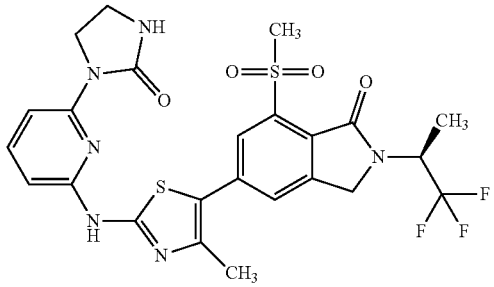 [SMILES: Cc1nc(Nc2cccc(N3CCNC3=O)n2)sc1-c1cc2c(c(S(C)(=O)=O)c1)C(=O)N([C@@H](C)C(F)(F)F)C2]

Prepared by the same general method as described for Example 1 using Intermediate 34 and Intermediate 75.

¹H NMR (500 MHz, DMSO-d₆) δ 1.52 (d, 3H), 2.47 (s, 3H), 3.47 (t, 2H), 3.61 (s, 3H), 4.27 (t, 2H), 4.61 (d, 1H), 4.81 (d, 1H), 5.04-5.15 (m, 1H), 6.62 (d, 1H), 7.25 (s, 1H), 7.63 (t, 1H), 7.72 (d, 1H), 8.05 (s, 1H), 8.10 (s, 1H), 11.50 (s, 1H).

m/z (ES+), [M+H]⁺=581.1; acid, HPLC t$_R$=1.77 min.

Example 12

5-(4-Methyl-2-{[6-(2-oxo-1,3-oxazolidin-3-yl)pyridin-2-yl]amino}-1,3-thiazol-5-yl)-7-(methylsulfonyl)-2-[(2S)-1,1,1-trifluoropropan-2-yl]-2,3-dihydro-1H-isoindol-1-one

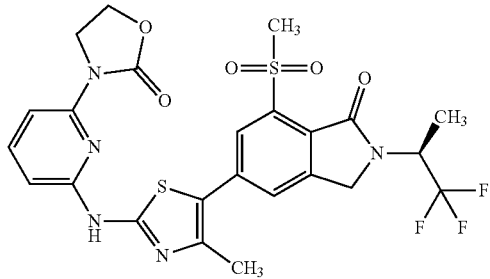 [SMILES: Cc1nc(Nc2cccc(N3CCOC3=O)n2)sc1-c1cc2c(c(S(C)(=O)=O)c1)C(=O)N([C@@H](C)C(F)(F)F)C2]

Prepared by the same general method as described for Example 1 using Intermediate 32 and Intermediate 76

¹H NMR (400 MHz, DMSO-d₆) δ 1.53 (d, 3H), 2.46 (s, 3H), 3.62 (s, 3H), 4.39-4.55 (m, 4H), 4.61 (d, 1H), 4.81 (d, 1H), 5.07-5.15 (m, 1H), 6.78 (d, 1H), 7.63 (d, 1H), 7.76 (t, 1H), 8.05 (d, 1H), 8.10 (d, 1H), 11.64 (s, 1H).

m/z (ES+), [M+H]⁺=582.1; acid, HPLC t$_R$=1.95 min.

Example 13

N-{6-[(5-{2-[(1S)-1-Cyclopropylethyl]-7-(methylsulfamoyl)-1-oxo-2,3-dihydro-1H-isoindol-5-yl}-4-methyl-1,3-thiazol-2-yl)amino]pyridin-2-yl}-N-methylacetamide

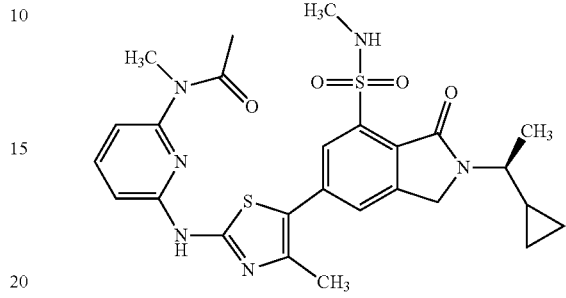

Prepared by the same general method as described for Example 1 using Intermediate 32 and N-(6-bromo-2-pyridyl)-N-methyl-acetamide.

¹H NMR (400 MHz, DMSO-d₆) δ 0.24-0.34 (m, 1H), 0.41-0.48 (m, 2H), 0.59-0.63 (m, 1H), 1.14-1.19 (m, 1H), 1.33 (d, 3H), 2.10 (s, 3H), 2.45 (s, 3H), 2.52 (d, 3H), 3.37 (s, 3H), 3.60-3.72 (m, 1H), 4.77 (s, 2H), 6.96 (d, 1H), 7.06 (d, 1H), 7.61 (q, 1H), 7.80 (t, 1H), 7.90 (d, 1H), 7.97 (d, 1H), 11.71 (s, 1H).

m/z (ES+), [M+H]⁺=555.2; acid, HPLC t$_R$=1.93 min.

Example 14

N-{6-[(5-{2-[(1S)-1-Cyclopropylethyl]-7-(methylsulfamoyl)-1-oxo-2,3-dihydro-1H-isoindol-5-yl}-4-methyl-1,3-thiazol-2-yl)amino]pyridin-2-yl}-2-methoxy-N-methylacetamide

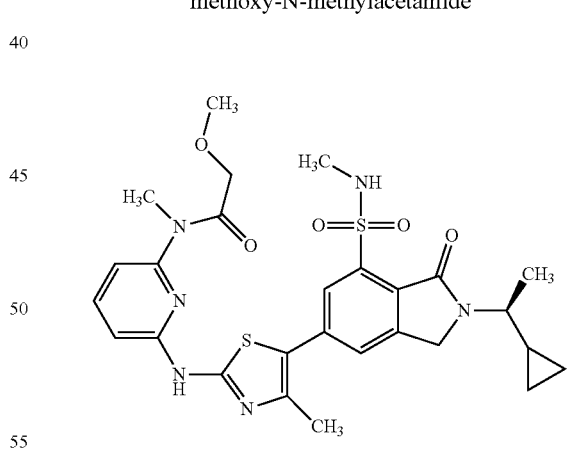

Prepared by the same general method as described for Example 1 using Intermediate 32 and Intermediate 78.

The initial product (306 mg) was suspended in acetonitrile (4 mL) and heated at 55° C. for 66 h then at 50° C. for 24 h, then at 40° C. for 24 h and then at 30° C. for 24 h and finally at ambient temperature for 24 h. The product was collected and dried to give the title compound (282 mg).

¹H NMR (400 MHz, DMSO-d₆) δ 0.27-0.31 (m, 1H), 0.41-0.47 (m, 2H), 0.59-0.63 (m, 1H), 1.14-1.19 (m, 1H), 1.33 (d, 3H), 2.45 (s, 3H), 3.23 (s, 3H), 3.37 (s, 3H), 3.64-3.68 (m, 1H), 4.19 (s, 2H), 4.76 (s, 2H), 6.97 (d, 1H), 7.09 (d, 1H), 7.61 (q, 1H), 7.80 (t, 1H), 7.89 (d, 1H), 7.96 (d, 1H), 11.70 (s, 1H) (3H obscured).

m/z (ES+), [M+H]+=585.5; acid, HPLC $t_R$=1.21 min.

Figure 4:
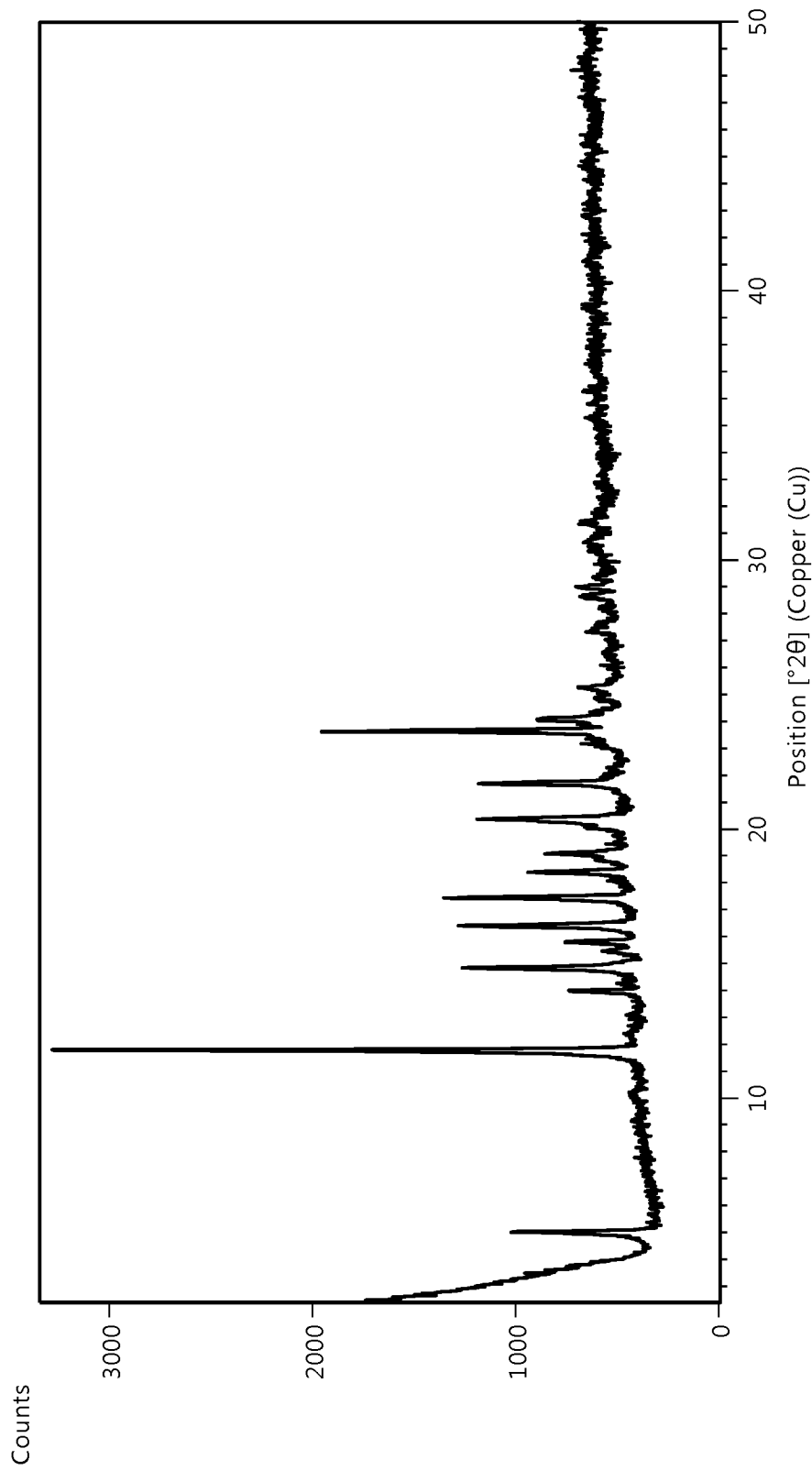
FIG. 4 shows the X-ray powder diffraction pattern for Example 14 N-{6-[(5-{2-[(1S)-1-Cyclopropylethyl]-7-(methylsulfamoyl)-1-oxo-2,3-dihydro-1H-isoindol-5-yl}-4-methyl-1,3-thiazol-2-yl)amino]pyridin-2-yl}-2-methoxy-N-methylacetamide.

The solid residue was found to be crystalline by XRPD and a typical diffractogram is displayed in FIG. 4. Characteristic peak positions are listed below in Tables 7 and 8.

TABLE 7

Five peaks characteristic for Example 14

| °2-theta | Relative intensity |
|---|---|
| 5.0 | m |
| 11.8 | vs |
| 14.8 | m |
| 17.4 | m |
| 23.6 | s |

TABLE 8

Peaks characteristic for Example 14

| °2-theta | Relative intensity |
|---|---|
| 5.0 | m |
| 11.8 | vs |
| 14.0 | w |
| 14.8 | m |
| 15.8 | w |
| 16.4 | m |
| 17.4 | m |
| 18.4 | w |
| 19.1 | w |
| 20.4 | m |
| 21.7 | m |
| 23.6 | s |
| 24.1 | m |
| 25.3 | w |

Example 15

(2R)—N-{6-[(5-{2-[(1S)-1-Cyclopropylethyl]-7-(methylsulfamoyl)-1-oxo-2,3-dihydro-1H-isoindol-5-yl}-4-methyl-1,3-thiazol-2-yl)amino]pyridin-2-yl}-2-methoxy-N-methylpropanamide

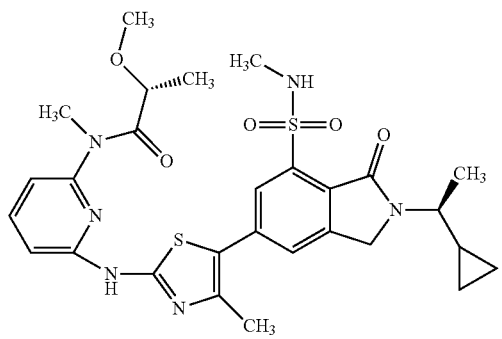 [SMILES: CNS(=O)(=O)c1cc(-c2sc(Nc3cccc(N(C)C(=O)[C@@H](C)OC)n3)nc2C)cc2c1C(=O)N([C@@H](C)C1CC1)C2]

Prepared by the same general method as described for Example 1 using Intermediate 32 and Intermediate 83.

$^1$H NMR (300 MHz, DMSO-d$_6$) δ 0.27-0.31 (m, 1H), 0.43-0.50 (m, 2H), 0.58-0.65 (m, 1H), 1.18 (d, 3H), 1.17-1.19 (m, 1H), 1.33 (d, 3H), 2.45 (s, 3H), 2.51 (s, 3H), 3.11 (s, 3H), 3.33 (s, 3H), 3.57-3.74 (m, 1H), 4.19 (q, 1H), 4.77 (s, 2H), 6.99-7.08 (m, 2H), 7.61 (q, 1H), 7.82-7.88 (m, 2H), 7.93 (s, 1H), 11.74 (s, 1H).

m/z (ES+), [M+H]+=599.2; acid, HPLC $t_R$=1.72 min.

Example 16

(2S)—N-{6-[(5-{2-[(1S)-1-Cyclopropylethyl]-7-(methylsulfamoyl)-1-oxo-2,3-dihydro-1H-isoindol-5-yl}-4-methyl-1,3-thiazol-2-yl)amino]pyridin-2-yl}-2-methoxy-N-methylpropanamide

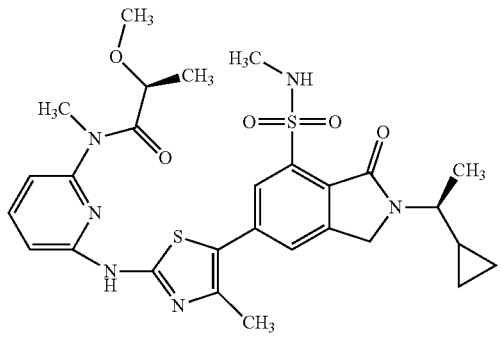 [SMILES: CNS(=O)(=O)c1cc(-c2sc(Nc3cccc(N(C)C(=O)[C@H](C)OC)n3)nc2C)cc2c1C(=O)N([C@@H](C)C1CC1)C2]

Prepared by the same general method as described for Example 1 using Intermediate 32 and Intermediate 80.

$^1$H NMR (300 MHz, DMSO-d$_6$) δ 0.22-0.36 (m, 1H), 0.40-0.48 (m, 2H), 0.54-0.68 (m, 1H), 1.18 (d, 3H), 1.16-1.20 (m, 1H) 1.33 (d, 3H), 2.45 (s, 3H), 2.52 (s, 3H), 3.11 (s, 3H), 3.34 (s, 3H), 3.57-3.73 (m, 1H), 4.19 (q, 1H), 4.77 (s, 2H), 6.99-7.08 (m, 2H), 7.61 (q, 1H), 7.82-7.88 (m, 2H), 7.93 (s, 1H), 11.77 (s, 1H).

m/z (ES+), [M+H]+=599.2; acid, HPLC $t_R$=1.96 min.

Example 17

N-{6-[(5-{2-[(1S)-1-Cyclopropylethyl]-7-(methylsulfamoyl)-1-oxo-2,3-dihydro-1H-isoindol-5-yl}-4-methyl-1,3-thiazol-2-yl)amino]pyridin-2-yl}-2-ethoxy-N-methylacetamide

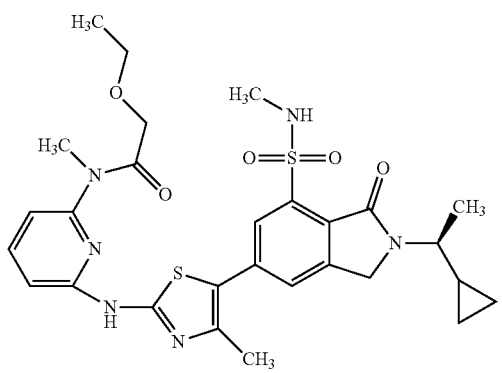 [SMILES: CCOCC(=O)N(C)c1cccc(Nc2nc(C)c(-c3cc4c(c(S(=O)(=O)NC)c3)C(=O)N([C@@H](C)C3CC3)C4)s2)n1]

Prepared by the same general method as described for Example 1 using Intermediate 32 and Intermediate 84.

$^1$H NMR (300 MHz, DMSO-d$_6$) δ 0.27-0.33 (m, 1H), 0.40-0.48 (m, 2H), 0.58-0.66 (m, 1H), 0.98 (t, 3H), 1.16-1.20 (m, 1H), 1.33 (d, 3H), 2.45 (s, 3H), 3.37 (s, 3H), 3.38

(q, 2H), 3.62-3.69 (m, 1H), 4.22 (s, 2H), 4.77 (s, 2H), 6.97 (d, 1H), 7.09 (d, 1H), 7.61 (q, 1H), 7.80 (t, 1H), 7.88 (d, 1H), 7.96 (d, 1H). 4H obscured.

m/z (ES+), [M+H]$^+$=599.2; acid, HPLC t$_R$=2.00 min.

Example 18

N-{6-[(5-{2-[(1S)-1-Cyclopropylethyl]-7-(methylsulfamoyl)-1-oxo-2,3-dihydro-1H-isoindol-5-yl}-4-methyl-1,3-thiazol-2-yl)amino]pyridin-2-yl}-N-ethyl-2-methoxyacetamide

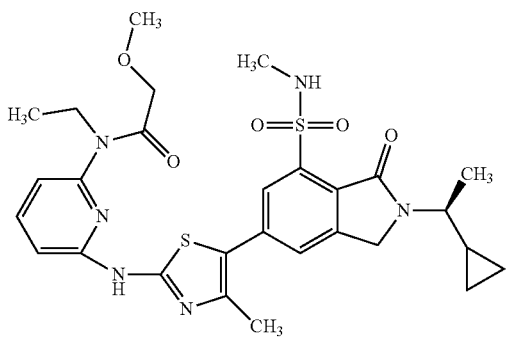 [SMILES: CCN(C(=O)COC)c1cccc(Nc2nc(C)c(-c3cc4c(c(S(=O)(=O)NC)c3)C(=O)N([C@@H](C)C3CC3)C4)s2)n1]

Prepared by the same general method as described for Example 1 using Intermediate 32 and Intermediate 79.

$^1$H NMR (300 MHz, DMSO-d$_6$) δ 0.26-0.30 (m, 1H), 0.39-0.47 (m, 2H), 0.60-0.64 (m, 1H), 1.14 (t, 3H), 1.16-1.20 (m, 1H), 1.33 (d, 3H), 2.45 (s, 3H), 2.56 (s, 3H), 3.19 (s, 3H), 3.58-3.67 (1H, m), 3.89 (q, 2H), 4.05 (s, 2H), 4.77 (s, 2H), 7.00 (d, 1H), 7.03 (d, 1H), 7.60 (q, 1H), 7.82 (t, 1H), 7.86 (d, 1H), 7.93 (d, 1H), 11.74 (s, 1H).

m/z (ES+), [M+H]$^+$=599.2; acid, HPLC t$_R$=1.99 min.

Example 19

2-[(1S)-1-Cyclopropylethyl]-N-methyl-6-(4-methyl-2-{[6-(2-oxopiperidin-1-yl)pyridin-2-yl]amino}-1,3-thiazol-5-yl)-3-oxo-2,3-dihydro-1H-isoindole-4-sulfonamide

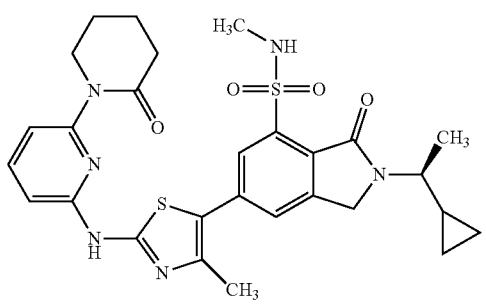 [SMILES: CNS(=O)(=O)c1cc(-c2sc(Nc3cccc(N4CCCCC4=O)n3)nc2C)cc2c1C(=O)N([C@@H](C)C1CC1)C2]

Prepared by the same general method as described for Example 1 using Intermediate 32 and Intermediate 73.

$^1$H NMR (300 MHz, DMSO-d$_6$) δ 0.27-0.31 (m, 1H), 0.40-0.48 (m, 2H), 0.60-0.64 (1H, m), 1.16-1.22 (m, 1H, m), 1.33 (3H, d), 1.84-1.96 (m, 4H), 3.62-3.68 (m, 1H), 4.07 (t, 2H), 4.76 (s, 2H), 6.86 (d, 1H), 7.31 (d, 1H), 7.57 (q, 1H), 7.73 (t, 1H), 7.92 (d, 1H), 8.01 (d, 1H), 11.62 (s, 1H). 8H obscured.

m/z (ES+), [M+H]$^+$=581.5; TFA, HPLC t$_R$=2.00 min.

Example 20

2-[(1S)-1-Cyclopropylethyl]-N-methyl-6-(4-methyl-2-{[6-(3-oxomorpholin-4-yl)pyridin-2-yl]amino}-1,3-thiazol-5-yl)-3-oxo-2,3-dihydro-1H-isoindole-4-sulfonamide

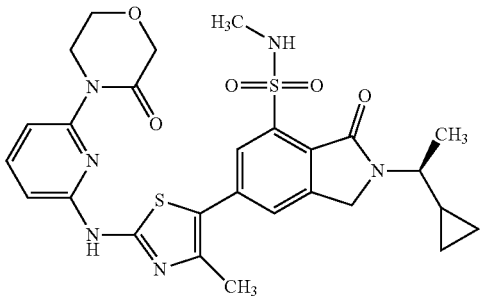 [SMILES: CNS(=O)(=O)c1cc(-c2sc(Nc3cccc(N4CCOCC4=O)n3)nc2C)cc2c1C(=O)N([C@@H](C)C1CC1)C2]

Prepared by the same general method as described for Example 1 using Intermediate 32 and Intermediate 53.

$^1$H NMR (500 MHz, DMSO-d$_6$) δ 0.25-0.32 (m, 1H), 0.38-0.49 (m, 2H), 0.57-0.65 (m, 1H), 1.13-1.21 (m, 1H), 1.33 (d, 3H), 2.47 (s, 3H), 2.51 (d, 3H), 3.61-3.69 (m, 1H), 4.05-4.09 (m, 2H), 4.15-4.20 (m, 2H), 4.30 (s, 2H), 4.76 (s, 2H), 6.90 (d, 1H), 7.54-7.63 (m, 2H), 7.77 (t, 1H), 7.92 (d, 1H), 8.00 (d, 1H), 11.65 (s, 1H).

m/z (ES+), [M+H]$^+$=583.2; TFA, HPLC t$_R$=1.97 min.

Figure 5:
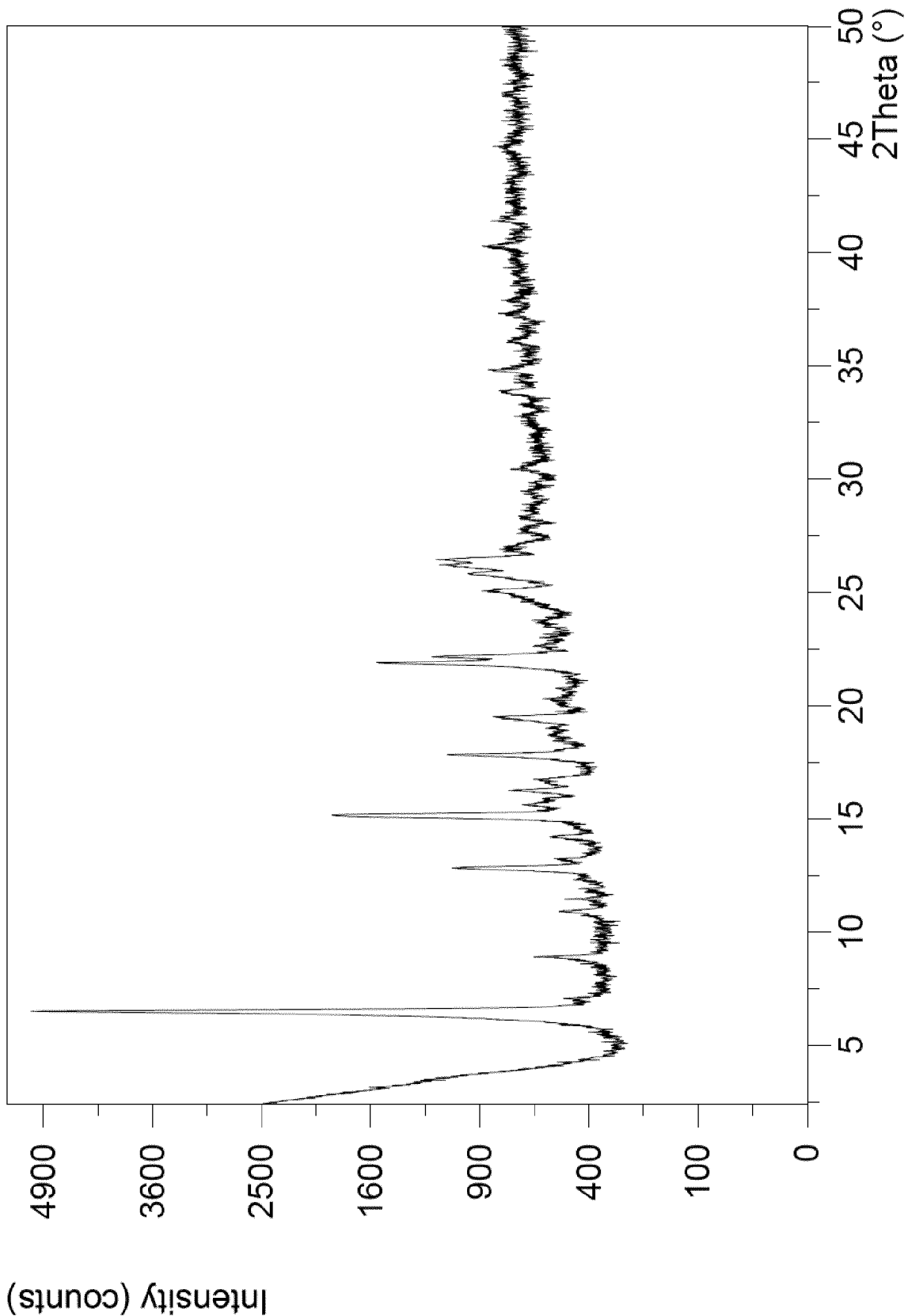
FIG. 5 shows the X-ray powder diffraction pattern for Example 20: 2-[(1S)-1-Cyclopropylethyl]-N-methyl-6-(4-methyl-2-{[6-(3-oxomorpholin-4-yl)pyridin-2-yl]amino}-1,3-thiazol-5-yl)-3-oxo-2,3-dihydro-1H-isoindole-4-sulfonamide, Form A.

The solid residue was found to be crystalline by XRPD and a typical diffractogram of Form A is displayed in FIG. 5. Characteristic peak positions are listed below in Tables 9 and 10.

TABLE 9

| Five peaks characteristic for Example 20, Form A | |
| --- | --- |
| °2-theta | Relative intensity |
| 6.5 | vs |
| 8.9 | vw |
| 12.8 | w |
| 15.2 | m |
| 21.9 | m |

TABLE 10

| Peaks characteristic for Example 20, Form A | |
| --- | --- |
| °2-theta | Relative intensity |
| 6.5 | vs |
| 8.9 | vw |
| 12.8 | w |
| 15.2 | m |
| 17.8 | w |
| 21.9 | m |
| 22.2 | m |
| 26.2 | w |
| 26.4 | w |

2-[(1S)-1-Cyclopropylethyl]-N-methyl-6-(4-methyl-2-{[6-(3-oxomorpholin-4-yl)pyridin-2-yl]amino}-1,3-thiazol-5-yl)-3-oxo-2,3-dihydro-1H-isoindole-4-sulfonamide (Example 20, 1.00 g) was dissolved in 10% MeOH/DCM (15 mL), SiliaMetS® Thiol, metal scavenger (1.34 mmol/g), 200 mg was added and the suspension was stirred at ambient temperature for 22 h, filtered and the solid residue washed with 10% MeOH/DCM. The resultant yellow filtrate was passed by gravity through a short column of SiliaMetS® Thiol, metal scavenger (1.34 mmol/g), 500 mg. The column was washed with several volumes of 10% MeOH/DCM to elute all product and this process was repeated. The resultant solution was filtered and to concentrated. The residue was taken up in MeCN and evaporated, treated with EtOH and evaporated, redissolved in EtOAc and evaporated slowly to 1 g yellow solid.

The solid was suspended in EtOAc (3 mL) and heated to 70° C. in a sealed flask without stirring but with swirling to mix the suspension, then allowed to stand at ambient temperature. The solid was collected by filtration, washed with EtOAc (3 mL) and dried under reduced pressure, at 40° C. for 3 days.

Figure 6:
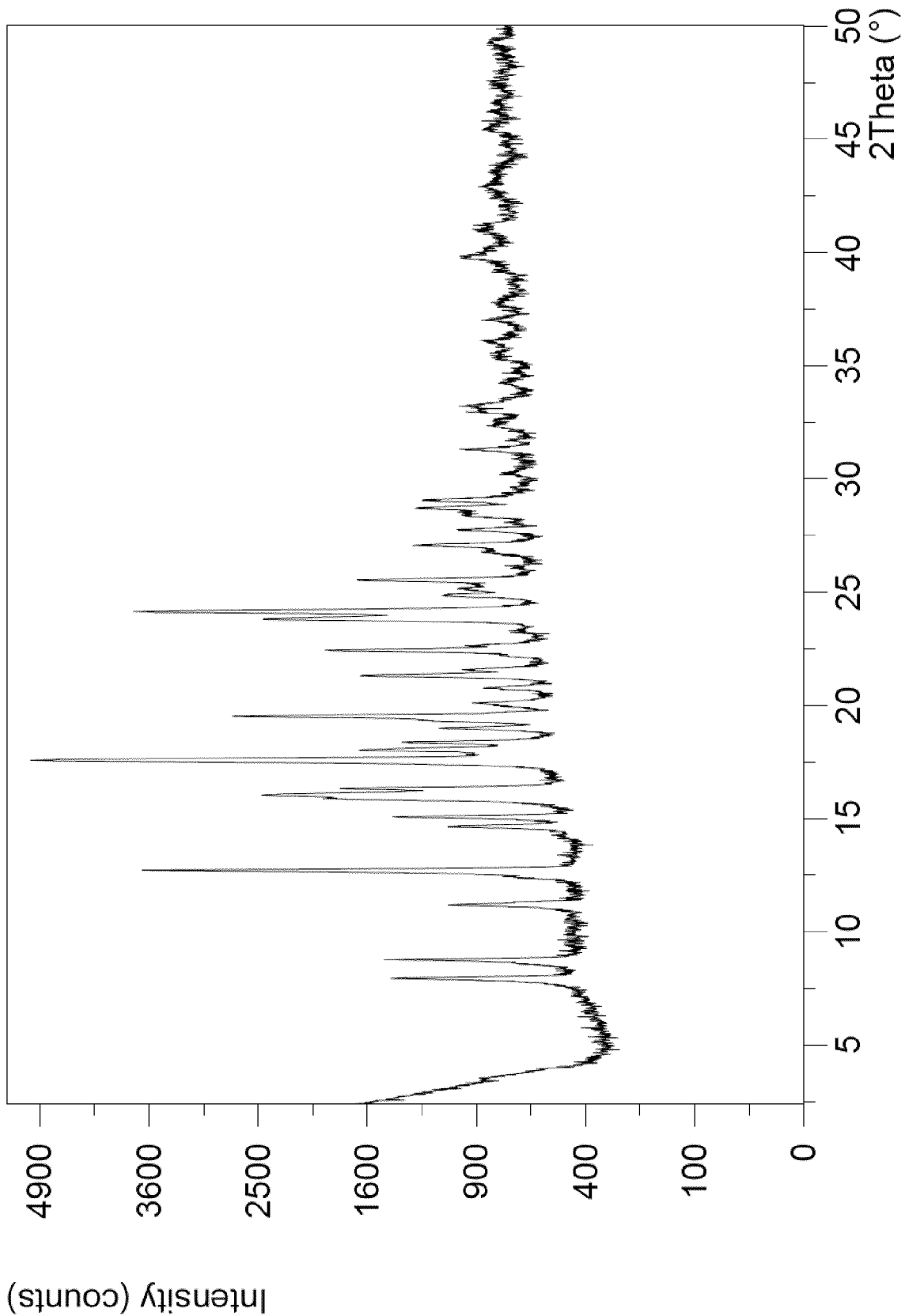
FIG. 6 shows the X-ray powder diffraction pattern for Example 20: 2-[(1S)-1-Cyclopropylethyl]-N-methyl-6-(4-methyl-2-{[6-(3-oxomorpholin-4-yl)pyridin-2-yl]amino}-1,3-thiazol-5-yl)-3-oxo-2,3-dihydro-1H-isoindole-4-sulfonamide, Form B.

The solid residue was found to be crystalline by XRPD and a typical diffractogram of Form B is displayed in FIG. 6. Characteristic peak positions are listed below in Tables 11 and 12.

TABLE 11

Five peaks characteristic for Example 20, Form B

| °2-theta | Relative intensity |
|---|---|
| 7.9 | m |
| 12.7 | s |
| 17.6 | vs |
| 19.5 | s |
| 24.1 | s |

TABLE 12

Peaks characteristic for Example 20, Form B

| °2-theta | Relative intensity |
|---|---|
| 7.9 | m |
| 8.8 | m |
| 11.2 | w |
| 12.7 | s |
| 14.6 | w |
| 15.1 | m |
| 15.9 | m |
| 16 | s |
| 16.3 | m |
| 17.6 | vs |
| 18 | m |
| 18.4 | w |
| 19 | w |
| 19.5 | s |
| 21.3 | m |
| 22.4 | m |
| 23.8 | s |
| 24.1 | s |
| 25.5 | m |

Example 21

2-[(1S)-1-Cyclopropylethyl]-N-methyl-6-(4-methyl-2-{[6-(2-oxo-1,3-oxazinan-3-yl)pyridin-2-yl]amino}-1,3-thiazol-5-yl)-3-oxo-2,3-dihydro-1H-isoindole-4-sulfonamide

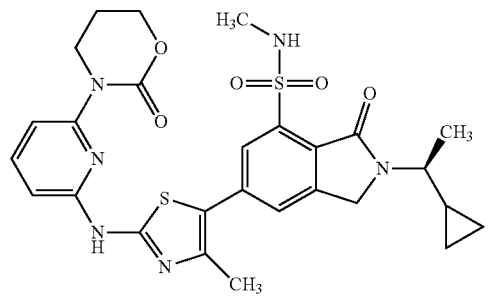 [SMILES: CNS(=O)(=O)c1cc(-c2sc(Nc3cccc(N4CCCOC4=O)n3)nc2C)cc2c1C(=O)N([C@@H](C)C1CC1)C2]

Prepared by the same general method as described for Example 1 using Intermediate 32 and Intermediate 74.

$^1$H NMR (400 MHz, DMSO-$d_6$) δ 0.26-0.30 (m, 1H), 0.37-0.50 (m, 2H), 0.58-0.62 (m, 1H), 1.14-1.18 (m, 1H), 1.32 (d, 3H), 2.19 (p, 2H), 2.47 (s, 3H), 3.55-3.73 (m, 1H), 4.13 (t, 2H), 4.30-4.51 (m, 2H), 4.75 (s, 2H), 6.85 (d, 1H), 7.37 (d, 1H), 7.56 (q, 1H), 7.74 (t, 1H), 7.92 (s, 1H), 8.01 (s, 1H), 11.62 (s, 1H). (3H obscured).

m/z (ES+), [M+H]$^+$=583.2; TFA, HPLC $t_R$=1.91 min.

Example 22

2-[(1S)-1-Cyclopropylethyl]-N-methyl-6-(4-methyl-2-{[6-(4-methyl-2-oxopiperazin-1-yl)pyridin-2-yl]amino}-1,3-thiazol-5-yl)-3-oxo-2,3-dihydro-1H-isoindole-4-sulfonamide

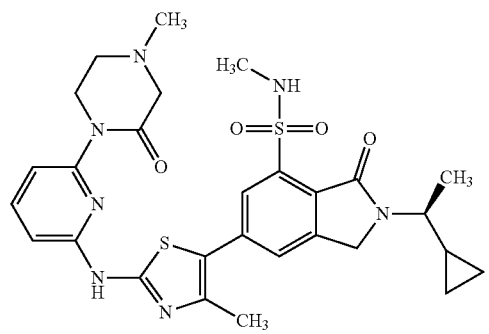 [SMILES: CNS(=O)(=O)c1cc(-c2sc(Nc3cccc(N4CCN(C)CC4=O)n3)nc2C)cc2c1C(=O)N([C@@H](C)C1CC1)C2]

Prepared by the same general method as described for Example 1 using Intermediate 32 and Intermediate 52.

$^1$H NMR (300 MHz, DMSO-$d_6$) δ 0.25-0.29 (m, 1H), 0.37-0.49 (m, 2H), 0.58-0.62 (m, 1H), 1.15-1.19 (m, 1H), 1.32 (d, 3H), 2.29 (s, 3H), 2.49 (s, 3H), 2.79-2.83 (m, 2H), 3.21 (s, 2H), 3.61-3.69 (m, 1H), 4.07-4.11 (m, 2H), 4.75 (s, 2H), 6.88 (d, 1H), 7.43 (d, 1H), 7.58 (q, 1H), 7.75 (t, 1H), 7.91 (d, 1H), 8.01 (d, 1H), 11.63 (s, 1H) (3H obscured).

m/z (ES+), [M+H]$^+$=596; acid, HPLC $t_R$=1.41 min.

Example 23

2-[(1S)-1-Cyclopropylethyl]-6-[2-({6-[(8aS)-1,4-dioxohexahydropyrrolo[1,2-a]pyrazin-2(1H)-yl]pyridin-2-yl}amino)-4-methyl-1,3-thiazol-5-yl]-N-methyl-3-oxo-2,3-dihydro-1H-isoindole-4-sulfonamide

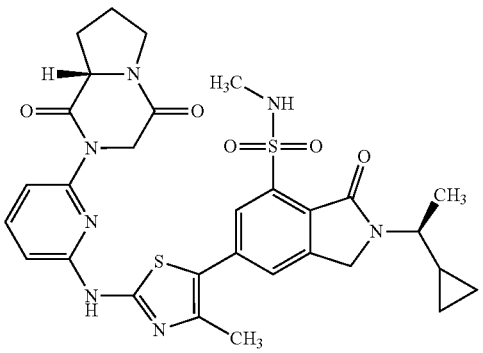 [SMILES: CNS(=O)(=O)c1cc(-c2sc(Nc3cccc(N4CC(=O)N5CCC[C@H]5C4=O)n3)nc2C)cc2c1C(=O)N([C@@H](C)C1CC1)C2]

Prepared by the same general method as described for Example 1 using Intermediate 32 and Intermediate 60.

$^1$H NMR (300 MHz, DMSO-d$_6$) δ 0.27-0.31 (m, 1H), 0.40-0.46 (m, 2H), 0.58-0.62 (m, 1H), 1.15-1.17 (m, 1H), 1.32 (d, 3H), 1.88-1.94 (m, 2H), 2.10-2.16 (m, 1H), 2.48 (s, 3H), 3.45 (t, 2H), 3.63-3.67 (m, 1H), 4.55 (t, 1H), 4.68 (d, 1H), 4.74 (s, 2H), 4.88 (dd, 1H), 6.90 (d, 1H), 7.40 (d, 1H), 7.57 (q, 1H), 7.79 (t, 1H), 7.93 (d, 1H), 8.03 (s, 1H), 11.68 (s, 1H). (4H obscured).

m/z (ES+), [M+H]$^+$=636.2; NH$_4$HCO$_3$, HPLC t$_R$=3.16 min.

Example 24

2-[(1S)-1-Cyclopropylethyl]-6-(2-{[6-(1,1-dioxido-1,2-thiazolidin-2-yl)pyridin-2-yl]amino}-4-methyl-1,3-thiazol-5-yl)-N-methyl-3-oxo-2,3-dihydro-1H-isoindole-4-sulfonamide

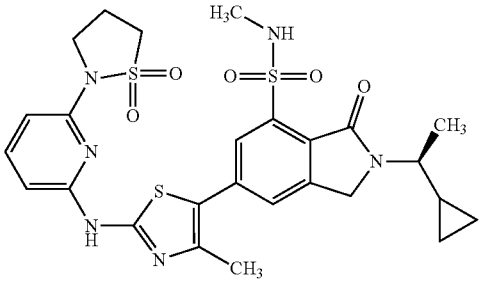 [SMILES: CNS(=O)(=O)c1cc(-c2sc(Nc3cccc(N4CCCS4(=O)=O)n3)nc2C)cc2c1C(=O)N([C@@H](C)C1CC1)C2]

Prepared by the same general method as described for Example 1 using Intermediate 32 and Intermediate 77.

$^1$H NMR (600 MHz, DMSO-d$_6$) δ 0.26-0.30 (m, 1H), 0.40-0.46 (m, 2H), 0.56-0.64 (m, 1H), 1.14-1.18 (m, 1H), 1.32 (d, 3H), 2.42-2.47 (m, 5H), 2.51 (s, 3H), 3.62 (t, 2H), 3.63-3.69 (m, 1H), 4.16 (t, 2H), 4.74 (s, 2H), 6.71 (d, 1H), 6.76 (d, 1H), 7.57 (q, 1H), 7.70 (t, 1H), 7.92 (d, 1H), 7.97 (d, 1H), 11.57 (s, 1H).

m/z (ES+), [M+H]$^+$=603.15; HPLC (pH 3) t$_R$=1.84 min.

Example 25

N-Methyl-6-(4-methyl-2-{[6-(2-oxopyrrolidin-1-yl)pyridin-2-yl]amino}-1,3-thiazol-5-yl)-3-oxo-2-[(2S)-1,1,1-trifluoropropan-2-yl]-2,3-dihydro-1H-isoindole-4-sulfonamide

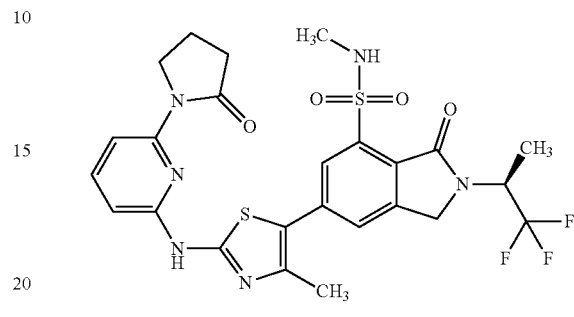

Prepared by the same general method as described for Example 1 using Intermediate 37 and Intermediate 66.

$^1$H NMR (300 MHz, DMSO-d$_6$) δ 1.53 (d, 3H), 2.10 (p, 2H), 2.47 (s, 3H), 2.60 (t, 2H), 4.24 (t, 2H), 4.63 (d, 1H), 4.84 (d, 1H), 5.07-5.13 (m, 1H), 6.77 (d, 1H), 7.16 (q, 1H), 7.73 (t, 1H), 7.86 (d, 1H), 7.96 (s, 1H), 7.80 (s, 1H), 11.59 (s, 1H). (3H obscured).

$^{19}$F NMR (282 MHz, DMSO-d$_6$) δ −73.44.

m/z (ES+), [M+H]$^+$=595.2; TFA, HPLC t$_R$=2.04 min.

Example 26

N-{6-[(5-{2-[(1S)-1-Cyclopropylethyl]-7-(ethylsulfamoyl)-1-oxo-2,3-dihydro-1H-isoindol-5-yl}-4-methyl-1,3-thiazol-2-yl)amino]pyridin-2-yl}-2-methoxy-N-methylacetamide

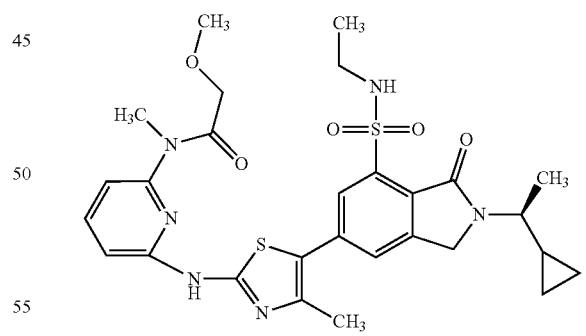

Prepared by the same general method as described for Example 1 using Intermediate 35 and Intermediate 78.

$^1$H NMR (300 MHz, DMSO-d$_6$) δ 0.27-0.31 (m, 1H), 0.40-0.48 (m, 2H), 0.58-0.62 (m, 1H), 0.97 (t, 3H), 1.16-1.20 (m, 1H), 1.34 (d, 3H), 2.45 (s, 3H), 2.84-2.92 (m, 2H), 3.23 (s, 3H), 3.37 (s, 3H), 3.65 (dd, 1H), 4.19 (s, 2H), 4.77 (s, 2H), 6.97 (d, 1H), 7.10 (d, 1H), 7.75-7.80 (m, 2H), 7.89 (s, 1H), 7.94 (s, 1H), 11.71 (s, 1H).

m/z (ES+), [M+H]$^+$=599.2; acid, HPLC t$_R$=2.01 min.

Example 27

N-Ethyl-6-(4-methyl-2-{[6-(3-oxomorpholin-4-yl)pyridin-2-yl]amino}-1,3-thiazol-5-yl)-3-oxo-2-[(2S)-1,1,1-trifluoropropan-2-yl]-2,3-dihydro-1H-isoindole-4-sulfonamide

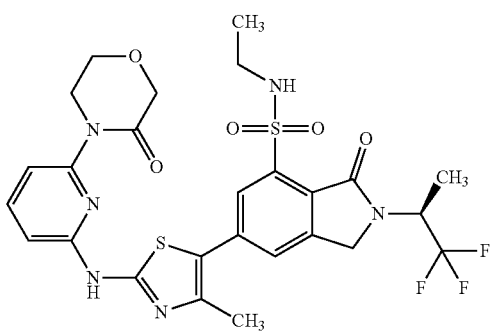 [SMILES: CCNS(=O)(=O)c1cc(-c2sc(Nc3cccc(N4CCOCC4=O)n3)nc2C)cc2c1C(=O)N([C@@H](C)C(F)(F)F)C2]

Prepared by the same general method as described for Example 1 using Intermediate 38 and Intermediate 50.

$^1$H NMR (300 MHz, DMSO-d$_6$) δ 0.97 (t, 3H), 1.53 (d, 3H), 2.48 (s, 3H), 2.87-2.95 (m, 2H), 4.06 (dd, 2H), 4.18 (dd, 2H), 4.29 (s, 2H), 4.63 (d, 1H), 4.84 (d, 1H), 5.07-5.17 (m, 1H), 6.89 (d, 1H), 7.31 (t, 1H), 7.60 (d, 1H), 7.77 (t, 1H), 7.96 (d, 1H), 8.01 (d, 1H), 11.68 (s, 1H).

$^{19}$F NMR (282 MHz, DMSO-d$_6$) δ −73.56.

m/z (ES+), [M+H]$^+$=625.2; TFA, HPLC t$_R$=2.08 min.

Example 28

6-(4-Methyl-2-{[6-(3-oxomorpholin-4-yl)pyridin-2-yl]amino}-1,3-thiazol-5-yl)-3-oxo-N-(propan-2-yl)-2-[(2S)-1,1,1-trifluoropropan-2-yl]-2,3-dihydro-1H-isoindole-4-sulfonamide

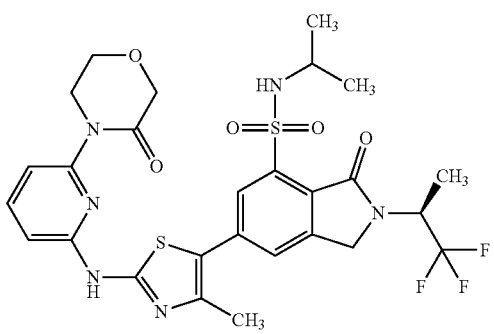 [SMILES: Cc1nc(Nc2cccc(N3CCOCC3=O)n2)sc1-c1cc2c(c(S(=O)(=O)NC(C)C)c1)C(=O)N([C@@H](C)C(F)(F)F)C2]

Prepared by the same general method as described for Example 1 using Intermediate 39 and Intermediate 50.

$^1$H NMR (300 MHz, DMSO-d$_6$) δ 0.96 (d, 3H), 1.04 (d, 3H), 1.54 (d, 3H), 3.24-3.34 (m, 1H), 4.07 (dd, dd, 2H), 4.18 (dd, 2H), 4.29 (s, 2H), 4.64 (d, 1H), 4.86 (d, 1H), 5.07-5.17 (m, 1H), 6.89 (d, 1H), 7.26 (d, 1H), 7.60 (d, 1H), 7.78 (t, 1H), 7.97 (d, 1H), 8.01 (d, 1H), 11.70 (s, 1H). 3H obscured.

$^{19}$F NMR (282 MHz, DMSO-d$_6$) δ −73.65.

m/z (ES+), [M+H]$^+$=639.2; TFA, HPLC t$_R$=2.15 min.

Example 29

6-(4-Methyl-2-{[6-(2-oxo-1,3-oxazinan-3-yl)pyridin-2-yl]amino}-1,3-thiazol-5-yl)-3-oxo-N-(propan-2-yl)-2-[(2S)-1,1,1-trifluoropropan-2-yl]-2,3-dihydro-1H-isoindole-4-sulfonamide

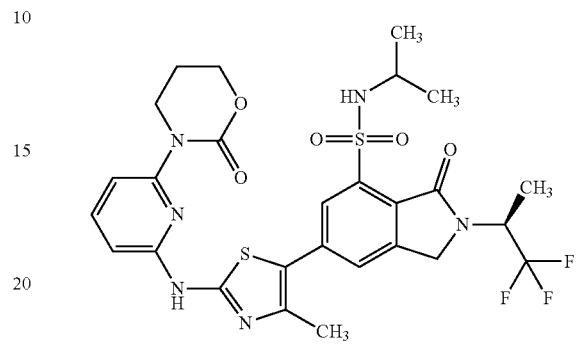

Prepared by the same general method as described for Example 1 using Intermediate 39 and Intermediate 74.

$^1$H NMR (300 MHz, DMSO-d$_6$) δ (d, 3H), 1.04 (d, 3H), 1.53 (d, 3H), 2.16-2.23 (m, 2H), 3.25-3.33 (m, 1H), 4.13 (t, 2H), 4.39 (t, 2H), 4.63 (d, 1H), 4.84 (d, 1H), 5.08-5.18 (m, 1H), 6.85 (d, 1H), 7.24 (d, 1H), 7.37 (d, 1H), 7.74 (t, 1H), 7.99 (d, 1H), 8.02 (d, 1H), 11.67 (s, 1H). 3H obscured.

$^{19}$F NMR (282 MHz, DMSO-d$_6$) δ −73.66.

m/z (ES+), [M+H]$^+$=639.2; TFA, HPLC t$_R$=2.11 min.

Example 30

6-(4-Methyl-2-{[6-(2-oxoimidazolidin-1-yl)pyridin-2-yl]amino}-1,3-thiazol-5-yl)-3-oxo-N-(propan-2-yl)-2-[(2S)-1,1,1-trifluoropropan-2-yl]-2,3-dihydro-1H-isoindole-4-sulfonamide

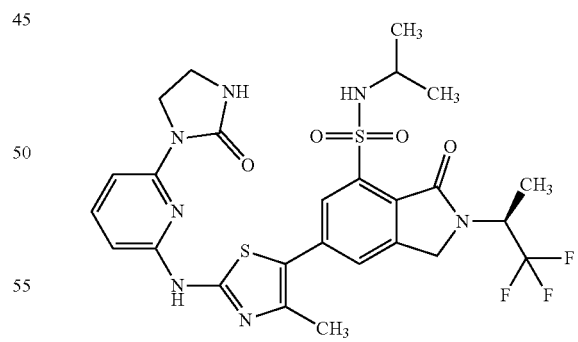

Prepared by the same general method as described for Example 1 using Intermediate 39 and Intermediate 75.

$^1$H NMR (300 MHz, DMSO-d$_6$) δ 0.96 (d, 3H), 1.04 (d, 3H), 1.53 (d, 3H), 2.46 (s, 3H), 3.22-3.36 (m, 1H), 3.46 (t, 2H), 4.27 (t, 2H), 4.63 (d, 1H), 4.84 (d, 1H), 5.07-5.17 (m, 1H), 6.62 (d, 1H), 7.24 (m, 2H), 7.67 (m, 2H), 7.97 (s, 2H), 11.50 (s, 1H). $^{19}$F NMR (282 MHz, DMSO-d$_6$) δ −73.65.

m/z (ES+), [M+H]$^+$=624.2; TFA, HPLC t$_R$=2.03 min.

Example 31

2-[(1S)-1-Cyclopropylethyl]-6-(4-methyl-2-{[6-(3-oxomorpholin-4-yl)pyridin-2-yl]amino}-1,3-thiazol-5-yl)-N-(oxetan-3-yl)-3-oxo-2,3-dihydro-1H-isoindole-4-sulfonamide

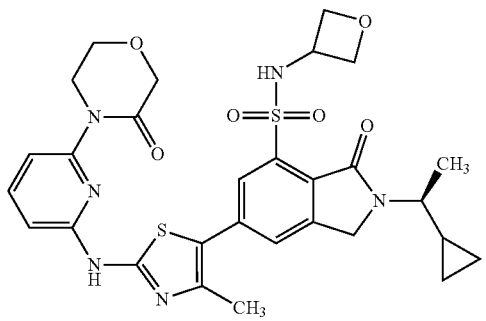 [SMILES: Cc1nc(Nc2cccc(N3CCOCC3=O)n2)sc1-c1cc2c(c(S(=O)(=O)NC3COC3)c1)C(=O)N([C@@H](C)C1CC1)C2]

Prepared by the same general method as described for Example 1 using Intermediate 41 and Intermediate 50.

$^1$H NMR (400 MHz, DMSO-d$_6$) δ 0.29-0.32 (m, 1H), 0.43-0.46 (m, 2H), 0.60-0.65 (m, 1H), 1.15-1.22 (m, 1H), 1.35 (d, 3H), 2.48 (s, 3H), 3.63-3.69 (m, 1H), 4.07 (dd, 2H), 4.18 (dd, 2H), 4.31 (s, 2H), 4.35-4.40 (m, 2H), 4.41-4.48 (m, 1H), 4.52-4.57 (m, 2H), 4.77 (s, 2H), 6.90 (d, 1H), 7.60 (d, 1H), 7.78 (t, 1H), 7.90 (d, 1H), 8.01 (d, 1H), 8.57 (d, 1H), 11.70 (s, 1H).

m/z (ES+), [M+H]$^+$=625.2; TFA, HPLC t$_R$=3.30 min.

Figure 7:
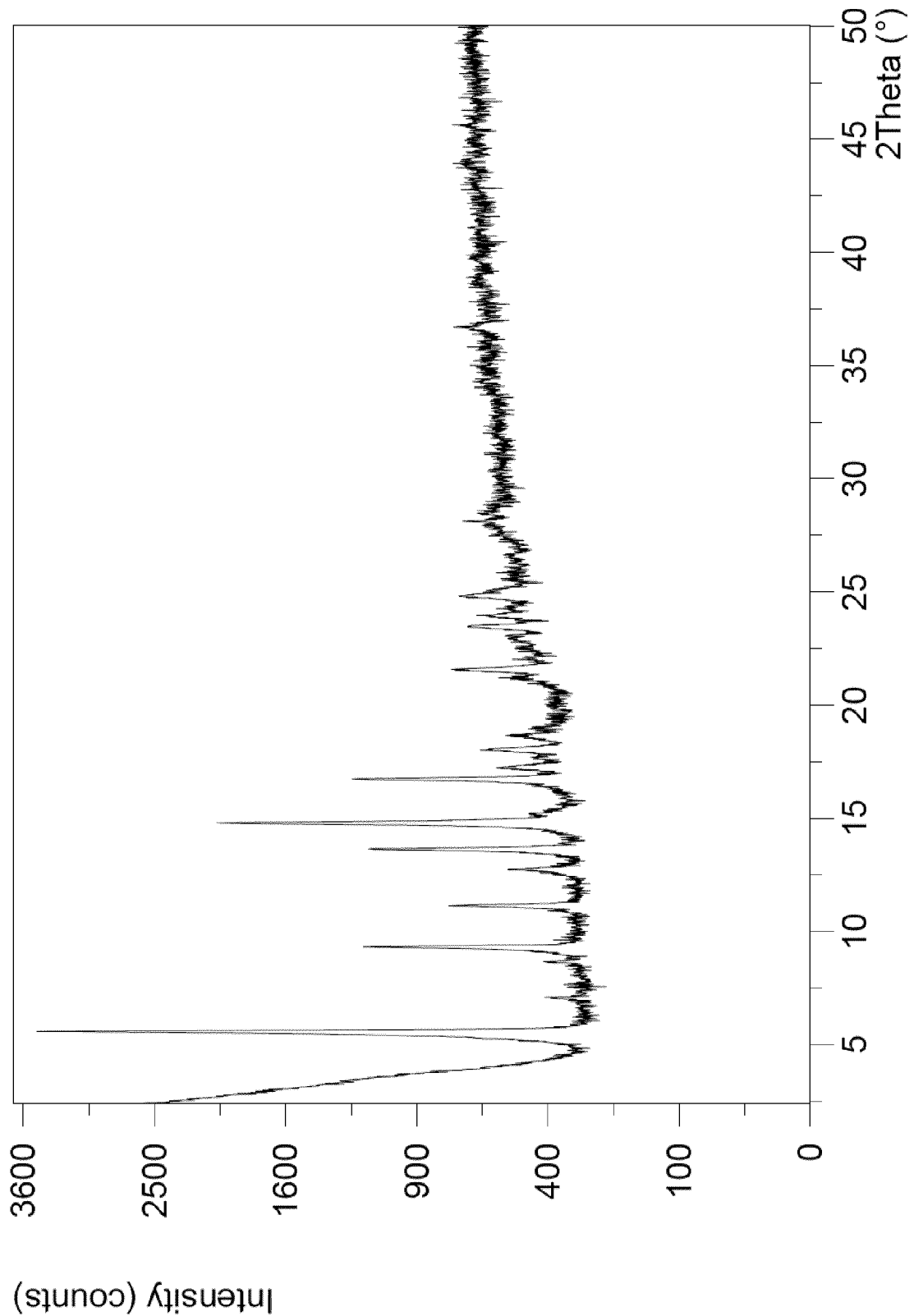
FIG. 7 shows the X-ray powder diffraction pattern for Example 31: 2-[(1S)-1-Cyclopropylethyl]-6-(4-methyl-2-{[6-(3-oxomorpholin-4-yl)pyridin-2-yl]amino}-1,3-thiazol-5-yl)-N-(oxetan-3-yl)-3-oxo-2,3-dihydro-1H-isoindole-4-sulfonamide.

The solid residue was found to be crystalline by XRPD and a typical diffractogram is displayed in FIG. 7. Characteristic peak positions are listed below in Tables 13 and 14.

TABLE 13

Five peaks characteristic for Example 31

| °2-theta | Relative intensity |
| --- | --- |
| 5.6 | vs |
| 9.3 | m |
| 13.6 | m |
| 14.8 | s |
| 16.7 | m |

TABLE 14

Peaks characteristic for Example 31

| °2-theta | Relative intensity |
| --- | --- |
| 5.6 | vs |
| 7.0 | vw |
| 9.3 | m |
| 11.1 | w |
| 12.7 | vw |
| 13.6 | m |
| 14.8 | s |
| 16.7 | m |
| 17.2 | w |
| 18.0 | w |
| 21.6 | w |
| 23.5 | w |

Example 32

2-[(1S)-1-Cyclopropylethyl]-6-(4-methyl-2-{[6-(2-oxopyrrolidin-1-yl)pyridin-2-yl]amino}-1,3-thiazol-5-yl)-N-(oxetan-3-yl)-3-oxo-2,3-dihydro-1H-isoindole-4-sulfonamide

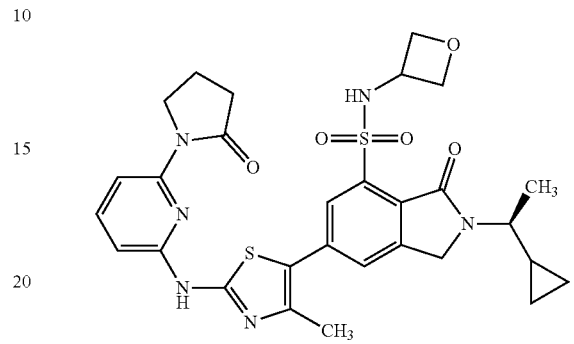

Prepared by the same general method as described for Example 1 using Intermediate 41 and Intermediate 66.

$^1$H NMR (300 MHz, DMSO-d$_6$) δ 0.29-0.32 (m, 1H), 0.40-0.48 (m, 2H), 0.59-0.63 (q, 1H), 1.17-1.24 (d, 1H), 1.34 (d, 3H), 2.06-2.16 (m, 2H), 2.45 (s, 3H), 2.60 (t, 2H), 3.65-3.70 (m, 1H), 4.25 (t, 2H), 4.34-4.39 (m, 2H), 4.36-4.51 (m, 1H), 4.51-4.57 (m, 2H), 4.76 (s, 2H), 6.77 (d, 1H), 7.72 (t, 1H), 7.86 (d, 1H), 7.87 (d, 1H), 7.98 (d, 1H), 8.53-8.60 (m, 1H), 11.57 (s, 1H).

m/z (ES+), [M+H]$^+$=609.2; TFA, HPLC t$_R$=1.97 min.

Figure 8:
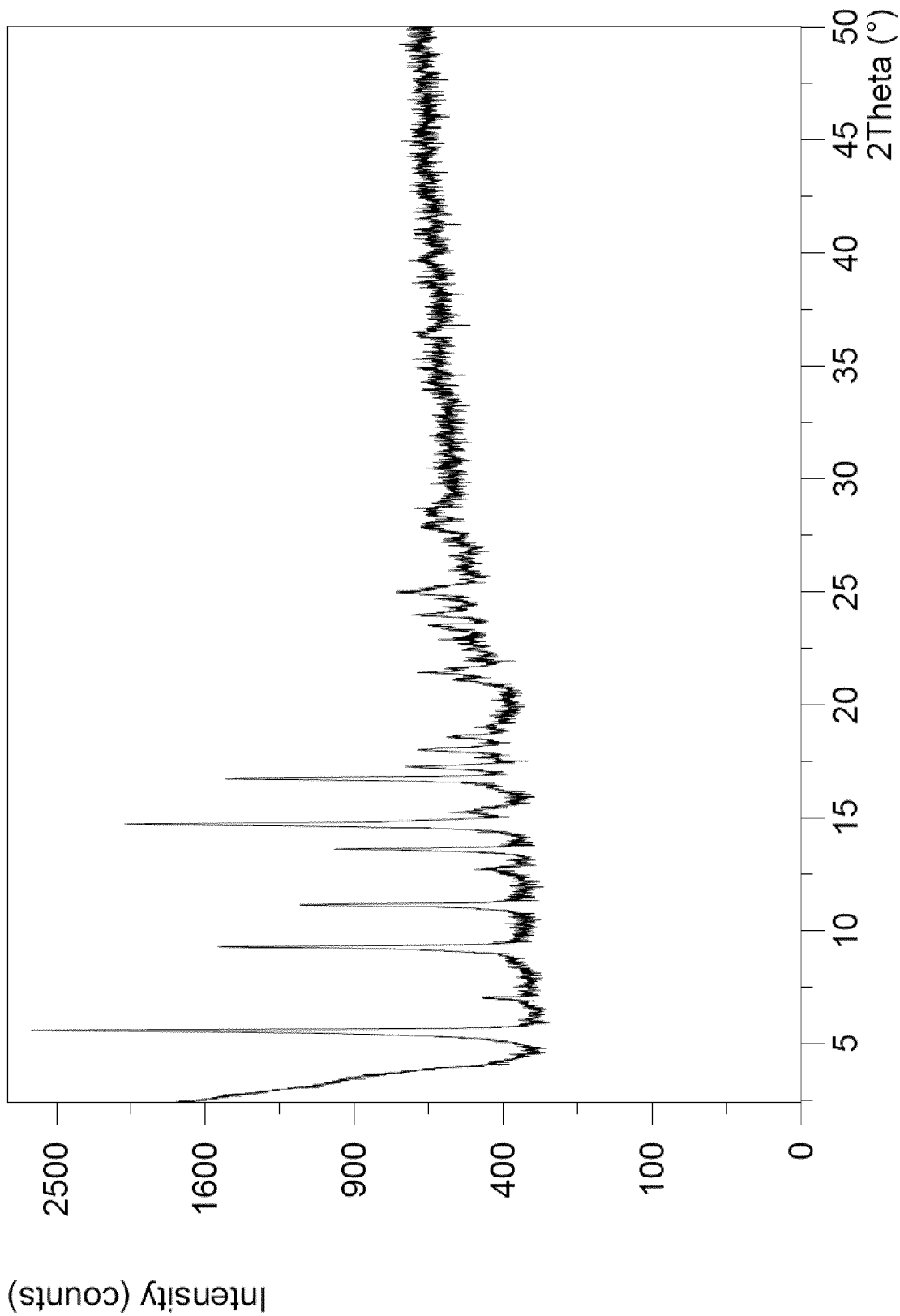
FIG. 8 shows the X-ray powder diffraction pattern for Example 32: 2-[(1S)-1-Cyclopropylethyl]-6-(4-methyl-2-{[6-(2-oxopyrrolidin-1-yl)pyridin-2-yl]amino}-1,3-thiazol-5-yl)-N-(oxetan-3-yl)-3-oxo-2,3-dihydro-1H-isoindole-4-sulfonamide.

The solid residue was found to be crystalline by XRPD and a typical diffractogram is displayed in FIG. 8. Characteristic peak positions are listed below in Tables 15 and 16.

TABLE 15

Five peaks characteristic for Example 32

| °2-theta | Relative intensity |
| --- | --- |
| 5.6 | vs |
| 9.3 | s |
| 11.1 | m |
| 14.7 | vs |
| 16.7 | s |

TABLE 16

Peaks characteristic for Example 32

| °2-theta | Relative intensity |
| --- | --- |
| 5.6 | vs |
| 7 | vw |
| 9.3 | s |
| 11.1 | m |
| 13.6 | m |
| 14.7 | vs |
| 16.7 | s |
| 17.2 | w |
| 18 | w |
| 21.4 | w |
| 24 | w |
| 25 | w |

Example 33

2-[(1S)-1-Cyclopropylethyl]-6-(4-methyl-2-{[6-(2-oxo-1,3-oxazolidin-3-yl)pyridin-2-yl]amino}-1,3-thiazol-5-yl)-N-(oxetan-3-yl)-3-oxo-2,3-dihydro-1H-isoindole-4-sulfonamide

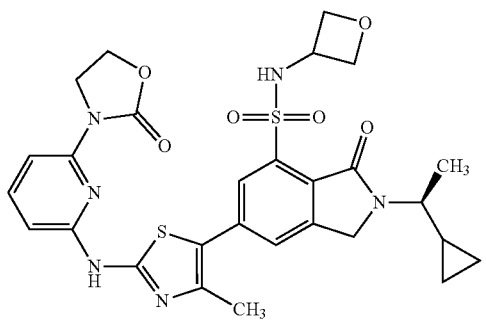 [SMILES: Cc1nc(Nc2cccc(N3CCOC3=O)n2)sc1-c1cc2c(c(S(=O)(=O)NC3COC3)c1)C(=O)N([C@@H](C)C1CC1)C2]

Prepared by the same general method as described for Example 1 using Intermediate 41 and Intermediate 76.

$^1$H NMR (300 MHz, DMSO-$d_6$) δ 0.27-0.31 (m, 1H), 0.40-0.44 (m, 2H), 0.59-0.63 (m, 1H), 1.13-1.21 (m, 1H), 1.34 (d, 3H), 2.44 (s, 3H), 3.62-3.72 (m, 1H), 4.33-4.57 (m, 9H), 4.74 (s, 2H), 6.77 (d, 1H), 7.62 (d, 1H), 7.75 (t, 1H), 7.90 (dd, 1H), 7.97 (d, 1H), 8.54 (d, 1H), 11.60 (s, 1H).

m/z (ES+), [M+H]$^+$=611.2; TFA, HPLC $t_R$=1.97 min.

Figure 9:
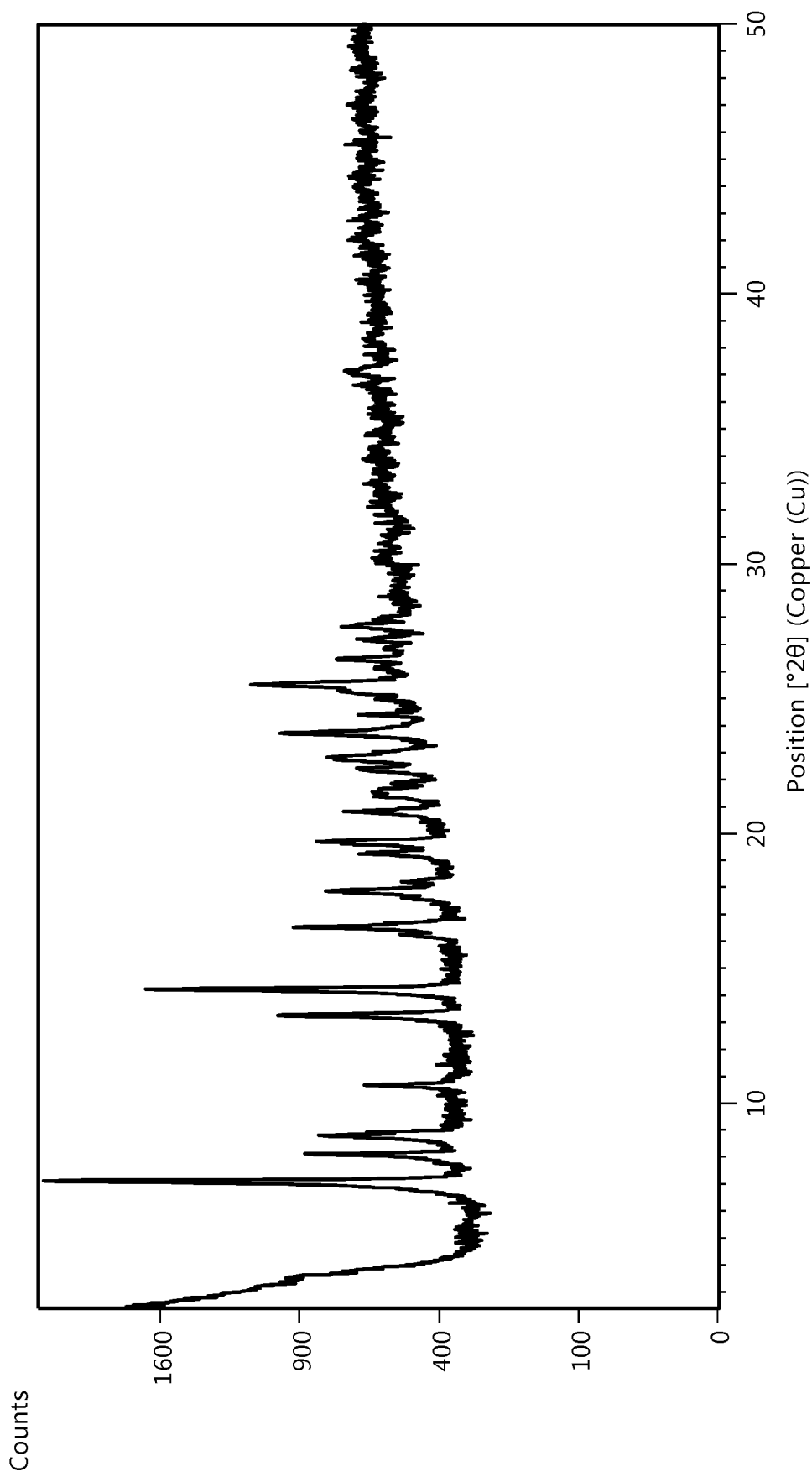
FIG. 9 shows the X-ray powder diffraction pattern for Example 33: 2-[(1S)-1-Cyclopropylethyl]-6-(4-methyl-2-{[6-(2-oxo-1,3-oxazolidin-3-yl)pyridin-2-yl]amino}-1,3-thiazol-5-yl)-N-(oxetan-3-yl)-3-oxo-2,3-dihydro-1H-isoindole-4-sulfonamide.

The solid residue was found to be crystalline by XRPD and a typical diffractogram is displayed in FIG. 9. Characteristic peak positions are listed below in Tables 17 and 18.

TABLE 17

Five peaks characteristic for Example 33

| °2-theta | Relative intensity |
|---|---|
| 7.1 | vs |
| 10.7 | w |
| 14.2 | vs |
| 16.5 | m |
| 25.5 | s |

TABLE 18

Peaks characteristic for Example 33

| °2-theta | Relative intensity |
|---|---|
| 7.1 | vs |
| 8.1 | m |
| 8.8 | m |
| 8.9 | w |
| 10.7 | w |
| 13.3 | m |
| 14.2 | vs |
| 16.2 | w |
| 16.5 | m |
| 17.9 | m |
| 19.3 | w |
| 19.6 | m |
| 19.7 | m |
| 20.8 | m |
| 22.8 | m |
| 23.7 | m |
| 24.4 | w |
| 25.5 | s |
| 26.5 | m |
| 27.7 | m |

Example 34

2-[(1S)-1-Cyclopropylethyl]-6-(4-methyl-2-{[6-(2-oxoimidazolidin-1-yl)pyridin-2-yl]amino}-1,3-thiazol-5-yl)-N-(oxetan-3-yl)-3-oxo-2,3-dihydro-1H-isoindole-4-sulfonamide

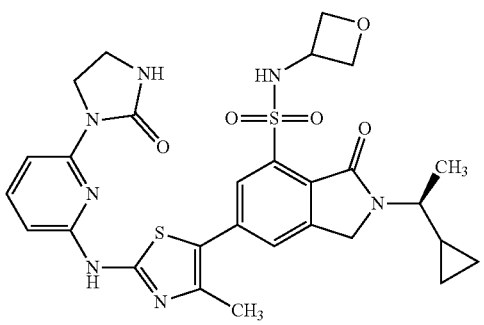 [SMILES: Cc1nc(Nc2cccc(N3CCNC3=O)n2)sc1-c1cc2c(c(S(=O)(=O)NC3COC3)c1)C(=O)N([C@@H](C)C1CC1)C2]

Prepared by the same general method as described for Example 1 using Intermediate 41 and Intermediate 75.

$^1$H NMR (300 MHz, DMSO-$d_6$) δ 0.26-0.31 (m, 1H), 0.40-0.46 (m, 2H), 0.58-0.63 (m, 1H), 1.14-1.23 (m, 1H), 1.34 (d, 3H), 2.44 (s, 3H), 3.46 (t, 2H), 3.64-3.69 (m, 1H), 4.27 (t, 2H), 4.33-4.41 (m, 2H), 4.40-4.50 (m, 1H), 4.50-4.56 (m, 2H), 4.74 (s, 2H), 6.61 (d, 1H), 7.24 (s, 1H), 7.62 (t, 1H), 7.72 (d, 1H), 7.89 (d, 1H), 7.97 (d, 1H), 8.54 (s, 1H), 11.46 (s, 1H).

m/z (ES+), [M+H]$^+$=610.3; TFA, HPLC $t_R$=1.80 min.

Example 35

2-[(1S)-1-Cyclopropylethyl]-6-(4-methyl-2-{[6-(2-oxo-1,3-oxazinan-3-yl)pyridin-2-yl]amino}-1,3-thiazol-5-yl)-N-(oxetan-3-yl)-3-oxo-2,3-dihydro-1H-isoindole-4-sulfonamide

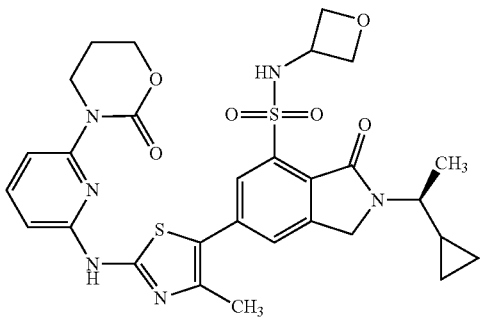 [SMILES: Cc1nc(Nc2cccc(N3CCCOC3=O)n2)sc1-c1cc2c(c(S(=O)(=O)NC3COC3)c1)C(=O)N([C@@H](C)C1CC1)C2]

Prepared by the same general method as described for Example 1 using Intermediate 41 and Intermediate 74.

¹H NMR (400 MHz, DMSO-d₆) δ 0.29-0.32 (m, 1H), 0.41-0.47 (m, 2H), 0.58-0.66 (m, 1H), 1.16-1.20 (m, 1H), 1.35 (d, 3H), 2.20 (p, 2H), 2.48 (s, 3H), 3.65-3.69 (m, 1H), 4.13 (t, 2H), 4.34-4.46 (m, 5H), 4.52-4.47 (m, 2H), 4.76 (s, 2H), 6.85 (d, 1H), 7.37 (d, 1H), 7.75 (t, 1H), 7.91 (d, 1H), 8.02 (d, 1H), 8.55-8.58 (m, 1H), 11.66 (m, 1H).

m/z (ES+), [M+H]⁺=625.2; TFA, HPLC $t_R$=1.89 min.

Example 36

6-(4-Methyl-2-{[6-(2-oxopiperidin-1-yl)pyridin-2-yl]amino}-1,3-thiazol-5-yl)-N-(oxetan-3-yl)-3-oxo-2-[(2S)-1,1,1-trifluoropropan-2-yl]-2,3-dihydro-1H-isoindole-4-sulfonamide

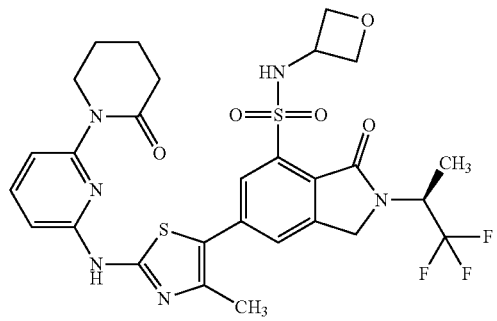 [SMILES: Cc1nc(Nc2cccc(N3CCCCC3=O)n2)sc1-c1cc2c(c(S(=O)(=O)NC3COC3)c1)C(=O)N([C@@H](C)C(F)(F)F)C2]

Prepared by the same general method as described for Example 1 using Intermediate 43 and Intermediate 73.

¹H NMR (400 MHz, DMSO-d₆) δ 1.54 (d, 3H), 2.10 (p, 2H), 2.46 (s, 3H), 2.60 (t, 2H), 4.24 (t, 2H), 4.36-4.42 (m, 2H), 4.46-4.58 (m, 3H), 4.63 (d, 1H), 4.83 (d, 1H), 5.06-5.18 (q, 1H), 6.78 (d, 1H), 7.73 (t, 1H), 7.86 (d, 1H), 7.95 (d, 1H), 8.00 (d, 1H), 8.16-8.19 (m, 1H), 11.59 (s, 1H). 2H obscured.

¹⁹F NMR (282 MHz, DMSO-d₆) δ −73.57.

m/z (ES+), [M+H]⁺=651.15; TFA, HPLC $t_R$=1.95 min.

Example 37

6-(4-Methyl-2-{[6-(2-oxopyrrolidin-1-yl)pyridin-2-yl]amino}-1,3-thiazol-5-yl)-N-(oxetan-3-yl)-3-oxo-2-[(2S)-1,1,1-trifluoropropan-2-yl]-2,3-dihydro-1H-isoindole-4-sulfonamide

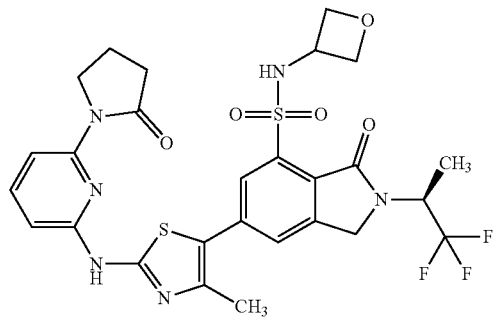 [SMILES: Cc1nc(Nc2cccc(N3CCCC3=O)n2)sc1-c1cc2c(c(S(=O)(=O)NC3COC3)c1)C(=O)N([C@@H](C)C(F)(F)F)C2]

Prepared by the same general method as described for Example 1 using Intermediate 43 and Intermediate 66.

¹H NMR (300 MHz, DMSO-d₆) δ 1.54 (d, 3H), 1.83-1.91 (m, 2H), 1.91-1.99 (m, 2H), 2.47 (s, 3H), 4.05 (t, 2H), 4.35-4.42 (m, 2H), 4.44-4.57 (m, 3H), 4.62 (d, 1H), 4.83 (d, 1H), 5.08-5.17 (m, 1H), 6.85 (d, 1H), 7.29 (d, 1H), 7.72 (t, 1H), 7.93 (d, 1H), 8.01 (d, 1H), 8.15-8.20 (m, 1H), 11.64 (s, 1H).

¹⁹F NMR (282 MHz, DMSO-d₆) δ −73.40.

m/z (ES+), [M+H]⁺=637.15; TFA, HPLC $t_R$=1.98 min.

Example 38

2-tert-Butyl-N-methyl-6-(4-methyl-2-{[6-(2-oxo-1,3-oxazinan-3-yl)pyridin-2-yl]amino}-1,3-thiazol-5-yl)-3-oxo-2,3-dihydro-1H-isoindole-4-sulfonamide

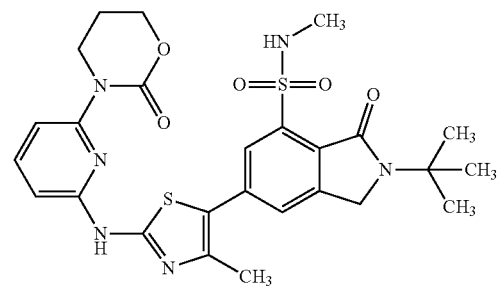 [SMILES: CNS(=O)(=O)c1cc(-c2sc(Nc3cccc(N4CCCOC4=O)n3)nc2C)cc2c1C(=O)N(C(C)(C)C)C2]

Prepared by the same general method as described for Example 1 using Intermediate 42 and Intermediate 74.

¹H NMR (300 MHz, DMSO-d₆) δ 1.53 (s, 9H), 2.19 (p, 2H), 2.45 (s, 3H), 4.12 (t, 2H), 4.35-4.40 (m, 2H), 4.77 (s, 2H), 6.84 (d, 1H), 7.36 (d, 1H), 7.57 (q, 1H), 7.74 (t, 1H), 7.90 (1H, d), 7.96 (1H, d), 11.63 (s, 1H). 3H obscured.

m/z (ES+), [M+H]⁺=571; acid, HPLC $t_R$=1.93 min.

Example 39

2-[(2S)-3,3-Dimethylbutan-2-yl]-N-methyl-6-(4-methyl-2-{[6-(3-oxomorpholin-4-yl)pyridin-2-yl]amino}-1,3-thiazol-5-yl)-3-oxo-2,3-dihydro-1H-isoindole-4-sulfonamide

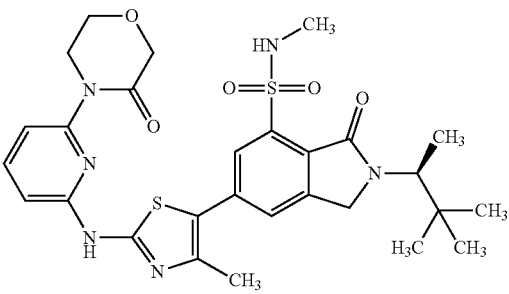 [SMILES: CNS(=O)(=O)c1cc(-c2sc(Nc3cccc(N4CCOCC4=O)n3)nc2C)cc2c1C(=O)N([C@@H](C)C(C)(C)C)C2]

Prepared by the same general method as described for Example 1 using Intermediate 40 and Intermediate 74.

¹H NMR (600 MHz, DMSO-d₆) δ 0.97 (s, 9H), 1.27 (d, 3H), 2.47 (s, 3H), 4.01-4.09 (m, 2H), 4.14-4.19 (m, 2H), 4.22 (q, 1H), 4.29 (s, 2H), 4.72 (s, 2H), 6.89 (d, 1H), 7.60

(dd, 2H), 7.77 (t, 1H), 7.91 (d, 1H), 7.97 (s, 1H), 11.65 (s, 1H). 3H obscured.
m/z (ES+), [M+H]$^+$=599; pH3, HPLC $t_R$=1.92 min.

Example 40

2-[(1S)-1-Cyclopropylethyl]-5-(4-methyl-2-{[6-(2-oxopiperazin-1-yl)pyridin-2-yl]amino}-1,3-thiazol-5-yl)-7-(methylsulfonyl)-2,3-dihydro-1H-isoindol-1-one

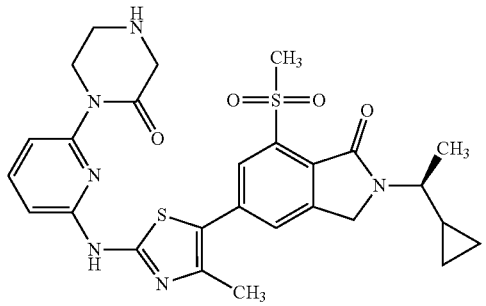 [SMILES: Cc1nc(Nc2cccc(N3CCNCC3=O)n2)sc1-c1cc2c(c(S(C)(=O)=O)c1)C(=O)N([C@@H](C)C1CC1)C2]

BBr$_3$ (0.05 mL, 0.53 mmol) was added dropwise to benzyl 4-{6-[(5-{2-[(1S)-1-cyclopropylethyl]-7-(methylsulfonyl)-1-oxo-2,3-dihydro-1H-isoindol-5-yl}-4-methyl-1,3-thiazol-2-yl)amino]pyridin-2-yl}-3-oxopiperazine-1-carboxylate (Intermediate 93, 120 mg, 0.17 mmol) in DCM (5 mL) at 0° C. over a period of 20 min. The resulting mixture was stirred at rt for 4 h. The reaction mixture was poured into ice (20 mL), extracted with DCM (3×20 mL), the aqueous layer was adjusted to pH=9 with saturated Na$_2$CO$_3$ and extracted with DCM (10 mL×3). The solvent was removed under reduced pressure. The crude product was purified by preparative HPLC (XBridge Prep C18 OBD column, 5 g silica, 19 mm diameter, 150 mm length), using decreasingly polar mixtures of water (containing 0.1% FA) and MeOH as eluents to give the title compound (25 mg) as a yellow solid.
$^1$H NMR (400 MHz, DMSO-d$_6$) δ 0.23-0.30 (m, 1H), 0.40-0.46 (m, 2H), 0.55-0.65 (m, 1H), 1.10-1.20 (m, 1H), 1.32 (d, 3H), 2.48 (s, 3H), 3.12 (t, 2H), 3.42-3.48 (m, 2H), 3.59-3.68 (m, 1H), 3.65 (s, 3H), 4.06 (t, 2H), 4.72 (s, 2H), 6.87 (d, 1H), 7.50 (d, 1H), 7.74 (t, 1H), 8.05 (s, 1H), 8.06 (s, 1H), 8.32 (br s, 2H).
m/z (ES+), [M+H]$^+$=567; acid, HPLC $t_R$=1.45 min.

Example 41

2-[(1S)-1-Cyclopropylethyl]-N-methyl-6-(4-methyl-2-{[6-(2-oxopiperazin-1-yl)pyridin-2-yl]amino}-1,3-thiazol-5-yl)-3-oxo-2,3-dihydro-1H-isoindole-4-sulfonamide

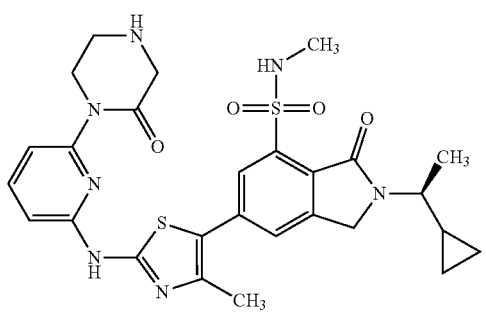 [SMILES: CNS(=O)(=O)c1cc(-c2sc(Nc3cccc(N4CCNCC4=O)n3)nc2C)cc2c1C(=O)N([C@@H](C)C1CC1)C2]

Prepared by the same general method as described for Example 40 using Intermediate 92.
$^1$H NMR (400 MHz, DMSO-d$_6$) δ 0.27-0.31 (m, 1H), 0.41-0.47 (m, 2H), 0.59-0.63 (m, 1H), 1.15-1.21 (m, 1H), 1.33 (d, 3H), 2.47 (s, 3H), 2.52 (s, 3H), 2.80-2.92 (m, 1H), 3.10 (t, 2H), 3.48 (s, 2H), 3.62-3.66 (m, 1H), 4.06 (t, 2H), 4.76 (s, 2H), 6.86 (d, 1H), 7.48 (d, 1H), 7.58 (q, 1H), 7.74 (t, 1H), 7.91 (d, 1H), 8.00 (d, 1H), 11.64 (s, 1H).
m/z (ES+), [M+H]$^+$=582; acid, HPLC $t_R$=2.51 min.

Example 42

2-[(1S)-1-Cyclopropylethyl]-N-methyl-6-[4-methyl-2-({6-[(5S)-5-methyl-2-oxopiperazin-1-yl]pyridin-2-yl}amino)-1,3-thiazol-5-yl]-3-oxo-2,3-dihydro-1H-isoindole-4-sulfonamide

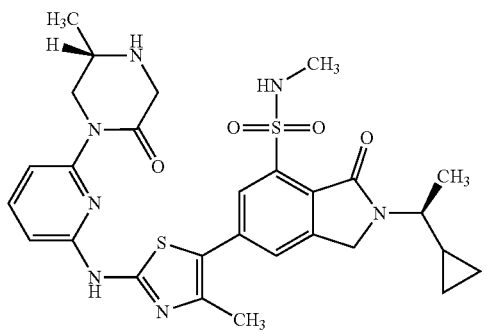 [SMILES: CNS(=O)(=O)c1cc(-c2sc(Nc3cccc(N4C[C@H](C)NCC4=O)n3)nc2C)cc2c1C(=O)N([C@@H](C)C1CC1)C2]

Prepared by the same general method as described for Example 40 using Intermediate 98.
$^1$H NMR (300 MHz, DMSO-d$_6$) δ 0.25-0.29 (m, 1H), 0.40-0.46 (m, 2H), 0.58-0.62 (m, 1H), 1.15-1.19 (m, 1H), 1.33 (d, 3H), 1.40-1.44 (m, 3H), 2.47 (s, 3H), 2.49 (s, 3H), 3.60-3.68 (m, 1H), 3.68-3.80 (m, 1H), 3.88 (d, 1H), 3.98 (d, 1H), 4.05-4.20 (m, 1H), 4.32 (dd, 1H), 4.75 (s, 2H), 6.92 (d, 1H), 7.49 (d, 1H), 7.62 (q, 1H), 7.79 (t, 1H), 7.89 (s, 1H), 8.05 (s, 1H), 9.52 (br s, 1H), 11.72 (br s, 1H).
m/z (ES+), [M+H]$^+$=596; base, HPLC $t_R$=2.53 min.

Example 43

2-[(1S)-1-Cyclopropylethyl]-N-methyl-6-[4-methyl-2-({6-[(3R)-3-methyl-2-oxopiperazin-1-yl]pyridin-2-yl}amino)-1,3-thiazol-5-yl]-3-oxo-2,3-dihydro-1H-isoindole-4-sulfonamide

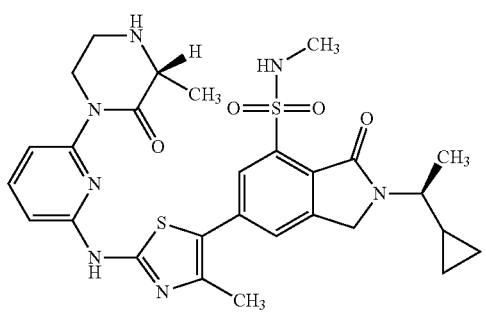 [SMILES: CNS(=O)(=O)c1cc(-c2sc(Nc3cccc(N4CCN[C@H](C)C4=O)n3)nc2C)cc2c1C(=O)N([C@@H](C)C1CC1)C2]

Prepared by the same general method as described for Example 40 using Intermediate 100.

$^1$H NMR (300 MHz, DMSO-d$_6$) δ 0.25-0.29 (m, 1H), 0.41-0.47 (m, 2H), 0.58-0.62 (m, 1H), 1.15-1.19 (m, 1H), 1.30 (d, 3H), 1.33 (d, 3H), 2.49 (s, 3H), 2.95-3.10 (m, 1H), 3.16-3.25 (m, 1H), 3.51-3.58 (m, 1H), 3.59-3.69 (m, 1H), 4.03-4.11 (m, 2H), 4.75 (s, 2H), 6.85 (d, 1H), 7.41 (d, 1H), 7.57 (q, 1H), 7.72 (t, 1H), 7.90 (d, 1H), 7.99 (d, 1H), 11.61 (s, 1H). (4H obscured).

m/z (ES+), [M+H]$^+$=596; acid, HPLC t$_R$=2.58 min.

Example 44

2-[(1S)-1-Cyclopropylethyl]-N-methyl-6-[4-methyl-2-({6-[(3S)-3-methyl-2-oxopiperazin-1-yl]pyridin-2-yl}amino)-1,3-thiazol-5-yl]-3-oxo-2,3-dihydro-1H-isoindole-4-sulfonamide

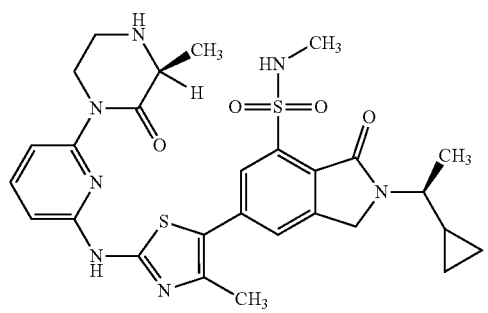 [SMILES: CNS(=O)(=O)c1cc(-c2sc(Nc3cccc(N4CCN[C@@H](C)C4=O)n3)nc2C)cc2c1C(=O)N([C@@H](C)C1CC1)C2]

Prepared by the same general method as described for Example 40 using Intermediate 101.

$^1$H NMR (300 MHz, DMSO-d$_6$) δ 0.26-0.30 (m, 1H), 0.40-0.46 (m, 2H), 0.58-0.62 (m, 1H), 1.12-1.21 (m, 1H), 1.30 (d, 3H), 1.33 (d, 3H), 2.48 (s, 3H), 2.54 (s, 3H), 2.79-2.91 (m, 1H), 2.98-3.08 (m, 1H), 3.18-3.27 (m, 1H), 3.50-3.58 (m, 1H), 3.60-3.70 (m, 1H), 4.03-4.10 (m, 2H), 4.75 (s, 2H), 6.85 (d, 1H), 7.41 (d, 1H), 7.57 (q, 1H), 7.72 (t, 1H), 7.90 (d, 1H), 7.99 (d, 1H), 11.61 (s, 1H).

m/z (ES+), [M+H]$^+$=596; acid, HPLC t$_R$=1.57 min.

Example 45

2-[(1S)-1-Cyclopropylethyl]-N-methyl-6-[4-methyl-2-({6-[(5R)-5-methyl-2-oxopiperazin-1-yl]pyridin-2-yl}amino)-1,3-thiazol-5-yl]-3-oxo-2,3-dihydro-1H-isoindole-4-sulfonamide

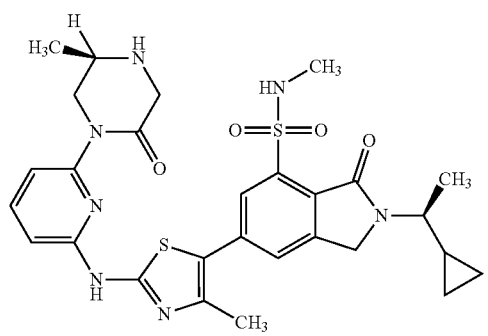 [SMILES: CNS(=O)(=O)c1cc(-c2sc(Nc3cccc(N4C[C@@H](C)NCC4=O)n3)nc2C)cc2c1C(=O)N([C@@H](C)C1CC1)C2]

Prepared by the same general method as described for Example 40 using Intermediate 99.

$^1$H NMR (300 MHz, DMSO-d$_6$) δ 0.25-0.32 (m, 1H), 0.37-0.49 (m, 2H), 0.57-0.64 (m, 1H), 1.11-1.22 (m, 1H), 1.17 (d, 3H), 1.32 (d, 3H), 2.47 (s, 3H), 2.65-2.80 (m, 1H), 3.07-3.16 (m, 1H), 3.41-3.58 (m, 2H), 3.60-3.71 (m, 2H), 4.14 (dd, 1H), 4.73 (s, 2H), 6.85 (d, 1H), 7.54 (d, 1H), 7.61 (q, 1H), 7.73 (t, 1H), 7.88 (d, 1H), 7.99 (d, 1H), 11.62 (s, 1H). (3H obscured).

m/z (ES+), [M+H]$^+$=596; acid, HPLC t$_R$=1.58 min.

Example 46

2-[(1S)-1-Cyclopropylethyl]-N-methyl-6-[4-methyl-2-({6-[(2R)-2-methyl-6-oxopiperazin-1-yl]pyridin-2-yl}amino)-1,3-thiazol-5-yl]-3-oxo-2,3-dihydro-1H-isoindole-4-sulfonamide

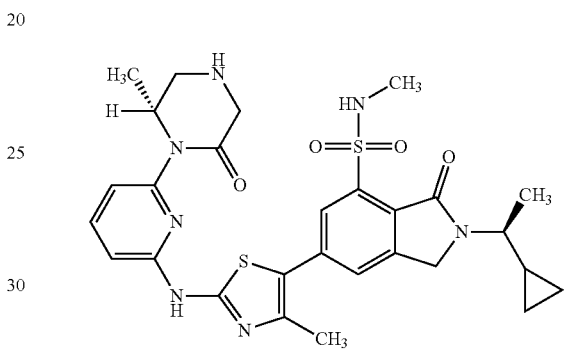

Prepared by the same general method as described for Example 40 using Intermediate 96.

$^1$H NMR (300 MHz, DMSO-d$_6$) δ 0.26-0.32 (m, 1H), 0.39-0.49 (m, 2H), 0.58-0.64 (m, 1H), 1.11-1.19 (m, 1H), 1.12 (d, 3H), 1.32 (d, 3H), 2.48 (s, 3H), 2.91 (dd, 1H), 3.18 (dd, 1H), 3.40 (d, 1H), 3.52 (d, 1H), 3.60-3.69 (m, 1H), 4.75 (s, 2H), 4.82-4.89 (m, 1H), 6.91 (d, 1H), 7.20 (d, 1H), 7.56 (q, 1H), 7.75 (t, 1H), 7.90 (d, 1H), 7.99 (d, 1H), 8.34 (s, 1H) 11.66 (s, 1H). (3H obscured).

m/z (ES+), [M+H]$^+$=596; acid, HPLC t$_R$=1.56 min.

Example 47

2-[(1S)-1-Cyclopropylethyl]-6-(2-{[6-(3,3-dimethyl-2-oxopiperazin-1-yl)pyridin-2-yl]amino}-4-methyl-1,3-thiazol-5-yl)-N-methyl-3-oxo-2,3-dihydro-1H-isoindole-4-sulfonamide

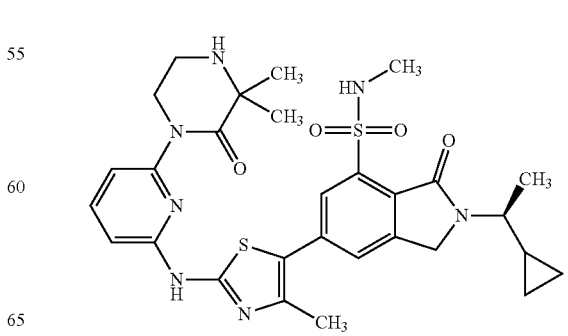

Prepared by the same general method as described for Example 40 using Intermediate 103.

¹H NMR (300 MHz, DMSO-d₆) δ 0.27-0.31 (m, 1H), 0.39-0.47 (m, 2H), 0.59-0.63 (m, 1H), 1.10-1.22 (m, 1H), 1.32-1.33 (m, 9H), 2.49 (s, 3H), 2.57-2.71 (s, 1H), 3.10-3.16 (m, 2H), 3.59-3.71 (m, 1H), 4.04 (t, 2H), 4.75 (s, 2H), 6.85 (d, 1H), 7.34 (d, 1H), 7.57 (q, 1H), 7.72 (t, 1H), 7.90 (d, 1H), 7.99 (d, 1H), 11.59 (s, 1H). (3H obscured).

m/z (ES+), [M+H]⁺=610.3; TFA, HPLC $t_R$=1.60 min.

Example 48

2-[(1S)-1-Cyclopropylethyl]-6-(2-{[6-(5,5-dimethyl-2-oxopiperazin-1-yl)pyridin-2-yl]amino}-4-methyl-1,3-thiazol-5-yl)-N-methyl-3-oxo-2,3-dihydro-1H-isoindole-4-sulfonamide

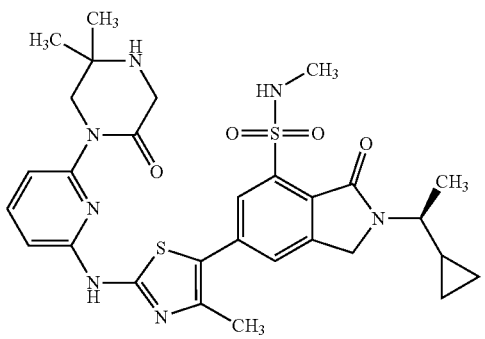 [SMILES: CNS(=O)(=O)c1cc(-c2sc(Nc3cccc(N4CC(C)(C)NCC4=O)n3)nc2C)cc2c1C(=O)N([C@@H](C)C1CC1)C2]

Prepared by the same general method as described for Example 40 using Intermediate 102.

¹H NMR (300 MHz, DMSO-d₆) δ 0.28-0.32 (m, 1H), 0.41-0.47 (m, 2H), 0.59-0.64 (dt, 1H), 1.13-1.22 (m, 8H), 1.33 (d, 3H), 2.47 (s, 3H), 2.62 (s, 3H), 3.47 (s, 2H), 3.63-3.69 (m, 1H), 3.93 (s, 2H), 4.74 (s, 2H), 6.87 (d, 1H), 7.45 (d, 1H), 7.61 (q, 1H), 7.75 (t, 1H), 7.88 (d, 1H), 8.00 (d, 1H), 11.65 (s, 1H).

m/z (ES+), [M+H]⁺=610; acid, HPLC $t_R$=1.61 min.

Example 49

2-[(1S)-1-Cyclopropylethyl]-N-methyl-6-[4-methyl-2-({6-[(2S)-2-methyl-6-oxopiperazin-1-yl]pyridin-2-yl}amino)-1,3-thiazol-5-yl]-3-oxo-2,3-dihydro-1H-isoindole-4-sulfonamide

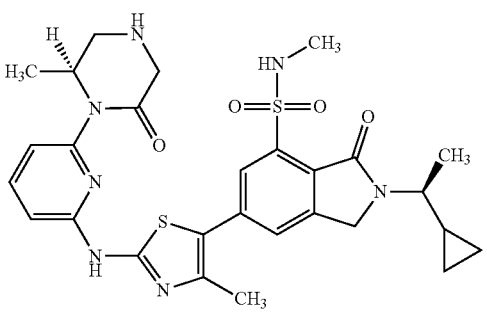 [SMILES: CNS(=O)(=O)c1cc(-c2sc(Nc3cccc(N4C(=O)CNC[C@@H]4C)n3)nc2C)cc2c1C(=O)N([C@@H](C)C1CC1)C2]

Prepared by the same general method as described for Example 40 using Intermediate 97.

¹H NMR (300 MHz, DMSO-d₆) δ 0.26-0.30 (m, 1H), 0.41-0.49 (m, 2H), 0.59-0.63 (m, 1H), 1.13 d, (3H), 1.12-1.19 (m, 1H), 1.33 (d, 3H), 2.48 (s, 3H), 2.92 (dd, 1H), 3.19 (dd, 1H), 3.40 (d, 1H), 3.52 (d, 1H), 3.60-3.70 (m, 1H), 4.76 (s, 2H), 4.86 (q, 1H), 6.92 (d, 1H), 7.21 (d, 1H), 7.56 (q, 1H), 7.76 (t, 1H), 7.91 (s, 1H), 8.00 (s, 1H), 11.67 (s, 1H). (4H obscured).

m/z (ES+), [M+H]⁺=596; acid, HPLC $t_R$=1.58 min.

Example 50

2-[(1S)-1-Cyclopropylethyl]-N-ethyl-6-(4-methyl-2-{[6-(2-oxopiperazin-1-yl)pyridin-2-yl]amino}-1,3-thiazol-5-yl)-3-oxo-2,3-dihydro-1H-isoindole-4-sulfonamide

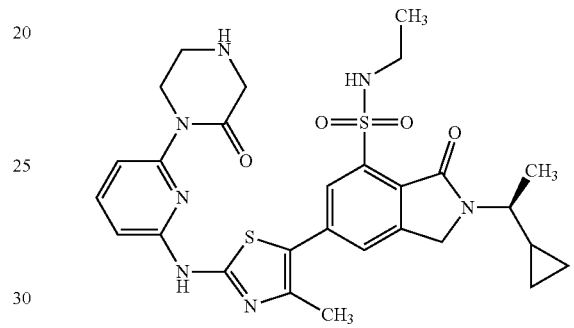

Prepared by the same general method as described for Example 40 using Intermediate 94.

¹H NMR (300 MHz, DMSO-d₆) δ 0.26-0.30 (m, 1H), 0.40-0.46 (m, 2H), 0.58-0.62 (m, 1H), 0.97 (t, 3H), 1.13-1.22 (m, 1H), 1.33 (d, 3H), 2.46 (s, 3H), 2.88 (p, 2H), 3.09 (t, 2H), 3.47 (s, 2H), 3.60-3.69 (m, 1H), 4.05 (t, 2H), 4.76 (s, 2H), 6.85 (d, 1H), 7.48 (d, 1H), 7.71-7.77 (m, 2H), 7.92 (d, 1H), 7.99 (d, 1H), 11.63 (s, 1H). (1H obscured).

m/z (ES+), [M+H]⁺=596; acid, HPLC $t_R$=1.64 min.

Example 51

2-[(1S)-1-Cyclopropylethyl]-6-(4-methyl-2-{[6-(2-oxopiperazin-1-yl)pyridin-2-yl]amino}-1,3-thiazol-5-yl)-3-oxo-N-(propan-2-yl)-2,3-dihydro-1H-isoindole-4-sulfonamide

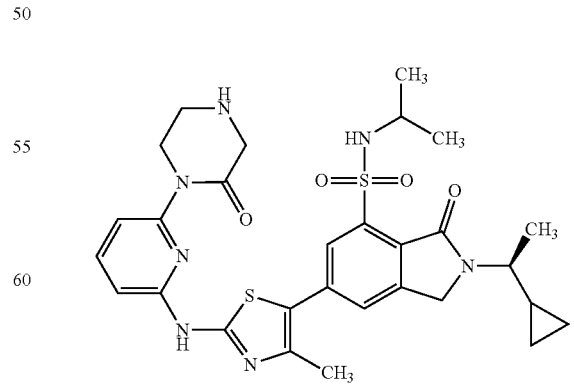

Prepared by the same general method as described for Example 40 using Intermediate 95.

¹H NMR (300 MHz, DMSO-d$_6$) δ 0.23-0.29 (m, 1H), 0.40-0.46 (m, 2H), 0.57-0.61 (m, 1H), 0.99 (d, 3H), 1.02 (d, 3H), 1.12-1.23 (m, 1H), 1.33 (d, 3H), 2.47 (s, 3H), 3.10 (t, 2H), 3.22-3.28 (m, 2H), 3.47 (s, 2H), 3.58-3.67 (m, 1H), 4.06 (t, 2H), 4.76 (s, 2H), 6.85 (d, 1H), 7.48 (d, 1H), 7.69-7.77 (m, 2H), 7.93 (d, 1H), 7.99 (d, 1H), 11.64 (s, 1H).

m/z (ES+), [M+H]$^+$=610; acid, HPLC t$_R$=1.48 min.

Example 52

2-[(1S)-1-Cyclopropylethyl]-N-methyl-6-(4-methyl-2-{[6-(2-oxo-1,4-diazepan-1-yl)pyridin-2-yl]amino}-1,3-thiazol-5-yl)-3-oxo-2,3-dihydro-1H-isoindole-4-sulfonamide

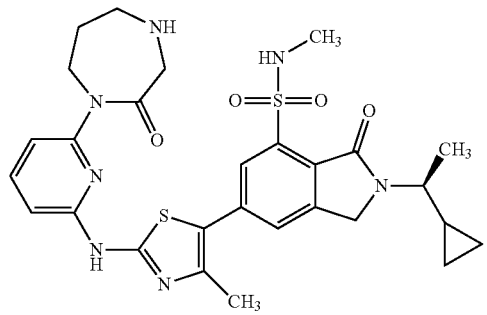 [SMILES: CNS(=O)(=O)c1cc(-c2sc(Nc3cccc(N4CCCNCC4=O)n3)nc2C)cc2c1C(=O)N([C@@H](C)C1CC1)C2]

TFA (1 mL, 12.98 mmol) was added to tert-butyl 4-{6-[(5-{2-[(1S)-1-cyclopropylethyl]-7-(methylsulfamoyl)-1-oxo-2,3-dihydro-1H-isoindol-5-yl}-4-methyl-1,3-thiazol-2-yl)amino]pyridin-2-yl}-3-oxo-1,4-diazepane-1-carboxylate (Intermediate 104, 90 mg, 0.13 mmol) in DCM (5 mL) at 25° C. under nitrogen. The resulting mixture was stirred at rt for 12 h. The solvent was removed under reduced pressure. The reaction mixture was basified with saturated Na$_2$CO$_3$ and extracted with DCM (3×10 mL) and concentrated. The crude product was purified by preparative HPLC: (Column: XSelect CSH Prep C18 OBD, 5 um, 19×150 mm; Mobile Phase A: Waters (0.1% FA), Mobile Phase B: MeCN; Flow rate: 30 mL/min; gradient: 20% B to 27% B in 7 min; 254/220 nm) to give the FA salt of the title compound (13 mg) as a yellow solid.

¹H NMR (300 MHz, DMSO-d$_6$) δ 0.25-0.29 (m, 1H), 0.40-0.46 (m, 2H), 0.58-0.62 (m, 1H), 0.94-1.00 (m, 1H), 1.10-1.24 (m, 1H), 1.32 (d, 3H), 1.97-2.07 (m, 2H), 2.93-3.01 (m, 2H), 3.58-3.70 (m, 3H), 4.21-4.31 (m, 2H), 4.75 (s, 2H), 6.83 (d, 1H), 7.28 (d, 1H), 7.53-7.60 (m, 1H), 7.70 (t, 1H), 7.90 (s, 1H), 8.00 (s, 1H), 8.34 (br s, 1H), 11.59 (s, 1H). (6H obscured).

m/z (ES+), [M+H]$^+$=596; acid, HPLC t$_R$=1.58 min.

Example 53

2-[(1S)-1-Cyclopropylethyl]-N-methyl-6-(4-methyl-2-{[6-(7-oxo-1,4-diazepan-1-yl)pyridin-2-yl]amino}-1,3-thiazol-5-yl)-3-oxo-2,3-dihydro-1H-isoindole-4-sulfonamide

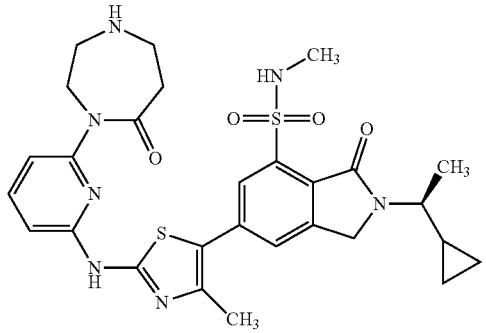 [SMILES: CNS(=O)(=O)c1cc(-c2sc(Nc3cccc(N4CCNCCC4=O)n3)nc2C)cc2c1C(=O)N([C@@H](C)C1CC1)C2]

Prepared by the same general method as described for Example 52 using Intermediate 105.

¹H NMR (300 MHz, DMSO-d$_6$) δ 0.25-0.31 (m, 1H), 0.37-0.47 (m, 2H), 0.56-0.64 (m, 1H), 1.10-1.21 (m, 1H), 1.33 (d, 3H), 2.47 (s, 3H), 2.74-2.81 (m, 2H), 2.85-2.91 (m, 2H), 3.13-3.18 (m, 2H), 3.59-3.69 (m, 1H), 4.17-4.22 (m, 2H), 4.75 (s, 2H), 6.83 (d, 1H), 7.23 (d, 1H), 7.56 (q, 1H), 7.71 (t, 1H), 7.90 (t, 1H), 7.99 (d, 1H). 11.63 (s, 1H). (4H obscured).

m/z (ES+), [M+H]$^+$=596; base, HPLC t$_R$=1.12 min.

Example 54

2-[(1S)-1-Cyclopropylethyl]-6-[2-({6-[(3R)-3-hydroxy-2-oxopyrrolidin-1-yl]pyridin-2-yl}amino)-4-methyl-1,3-thiazol-5-yl]-N-methyl-3-oxo-2,3-dihydro-1H-isoindole-4-sulfonamide

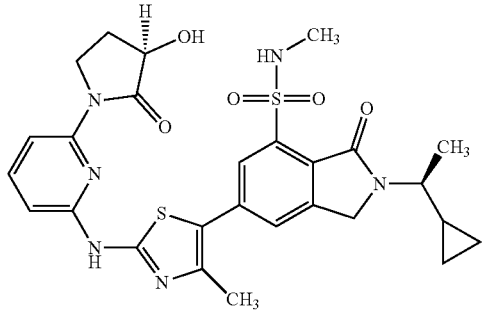 [SMILES: CNS(=O)(=O)c1cc(-c2sc(Nc3cccc(N4CC[C@@H](O)C4=O)n3)nc2C)cc2c1C(=O)N([C@@H](C)C1CC1)C2]

Triethylamine trihydrofluoride (324 mg, 2.01 mmol) was added to 6-[2-({6-[(3R)-3-{[tert-butyl(dimethyl)silyl]oxy}-2-oxopyrrolidin-1-yl]pyridin-2-yl}amino)-4-methyl-1,3-thiazol-5-yl]-2-[(1S)-1-cyclopropylethyl]-N-methyl-3-oxo-2,3-dihydro-1H-isoindole-4-sulfonamide (Intermediate 107, 140 mg) in THF (5 mL). The resulting mixture was stirred at rt for 3 h. The solvent was removed under reduced pressure. The crude product was purified by preparative HPLC (Column: XBridge Shield RP18 OBD, 5 μm, 19×150 mm; Mobile Phase A: Waters (10 mmol/L NH$_4$HCO$_3$), Mobile Phase B: MeCN; Flow rate: 25 mL/min; Gradient:

33% B to 55% B in 8 min; 254/220 nm) to give the title compound (40 mg) as a yellow solid.

$^1$H NMR (300 MHz, DMSO-d$_6$) δ 0.28-0.32 (m, 1H), 0.40-0.46 (m, 2H), 0.59-0.63 (m, 1H), 1.14-1.22 (m, 1H), 1.33 (d, 3H), 1.82-1.95 (m, 1H), 2.46 (s, 3H), 3.60-3.70 (m, 1H), 3.93-4.02 (m, 1H), 4.28 (t, 1H), 4.37-4.45 (m, 1H), 4.76 (s, 2H), 5.85 (d, 1H), 6.79 (d, 1H), 7.54-7.62 (m, 1H), 7.74 (t, 1H), 7.86-7.91 (m, 2H), 7.98 (s, 1H), 11.56 (br s, 1H). (4H obscured).

m/z (ES+), [M+H]$^+$=583; acid, HPLC t$_R$=1.83 min.

Example 55

2-[(1S)-1-Cyclopropylethyl]-6-[2-({6-[(4R)-4-hydroxy-2-oxopyrrolidin-1-yl]pyridin-2-yl}amino)-4-methyl-1,3-thiazol-5-yl]-N-methyl-3-oxo-2,3-dihydro-1H-isoindole-4-sulfonamide

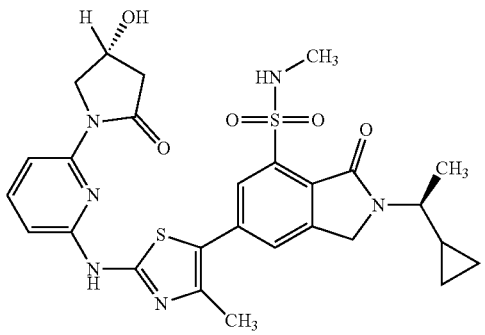 [SMILES: CNS(=O)(=O)c1cc(-c2sc(Nc3cccc(N4C[C@H](O)CC4=O)n3)nc2C)cc2c1C(=O)N([C@@H](C)C1CC1)C2]

Prepared by the same general method as described for Example 54 using Intermediate 109.

$^1$H NMR (300 MHz, DMSO-d$_6$) δ 0.26-0.30 (1H), 0.41-0.47 (m, 2H), 0.58-0.62 (m, 1H), 1.32 (d, 3H), 2.45 (s, 3H), 2.96 (dd, 1H), 3.62-3.67 (m, 1H), 4.17 (d, 1H), 4.30 (dd, 1H), 4.39-4.43 (m, 1H), 4.75 (s, 2H), 5.30 (d, 1H), 6.78 (d, 1H), 7.50-7.62 (m, 1H), 7.73 (t, 1H), 7.88 (d, 1H), 7.92 (d, 1H), 7.97 (d, 1H). (5H obscured).

m/z (ES+), [M+H]$^+$=583.2; TFA, HPLC t$_R$=2.82 min.

Example 56

2-[(1S)-1-Cyclopropylethyl]-6-[2-({6-[(3S)-3-hydroxy-2-oxopyrrolidin-1-yl]pyridin-2-yl}amino)-4-methyl-1,3-thiazol-5-yl]-N-methyl-3-oxo-2,3-dihydro-1H-isoindole-4-sulfonamide

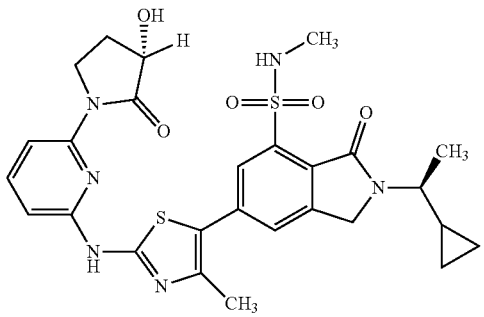 [SMILES: CNS(=O)(=O)c1cc(-c2sc(Nc3cccc(N4CC[C@H](O)C4=O)n3)nc2C)cc2c1C(=O)N([C@@H](C)C1CC1)C2]

Prepared by the same general method as described for Example 54 using Intermediate 108.

$^1$H NMR (500 MHz, DMSO-d$_6$) δ 0.25-0.32 (m, 1H), 0.38-0.49 (m, 2H), 0.57-0.65 (m, 1H), 1.14-1.21 (m, 1H), 1.33 (d, 3H), 1.83-1.94 (m, 1H), 2.41-2.48 (m, 1H), 2.45 (s, 3H), 2.52 (d, 3H), 3.61-3.69 (m, 1H), 3.93-4.02 (m, 1H), 4.28 (t, 1H), 4.41 (t, 1H), 4.76 (s, 2H), 5.78 (vbrs, 1H), 6.80 (d, 1H), 7.58 (q, 1H), 7.75 (t, 1H), 7.89 (d, 1H), 7.92 (d, 1H), 7.98 (d, 1H), 11.58 (s, 1H).

m/z (ES+), [M+H]$^+$=583.2; TFA, HPLC t$_R$=1.83 min

Example 57

2-[(1S)-1-Cyclopropylethyl]-6-[2-({6-[(2S)-2-(hydroxymethyl)-5-oxopyrrolidin-1-yl]pyridin-2-yl}amino)-4-methyl-1,3-thiazol-5-yl]-N-methyl-3-oxo-2,3-dihydro-1H-isoindole-4-sulfonamide

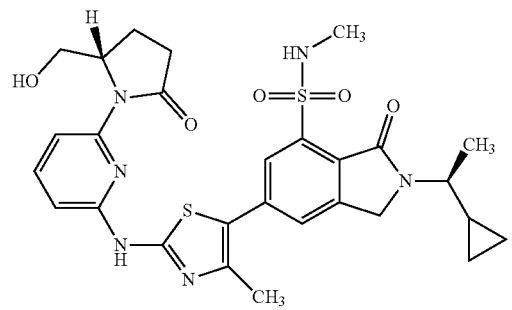 [SMILES: CNS(=O)(=O)c1cc(-c2sc(Nc3cccc(N4C(=O)CC[C@H]4CO)n3)nc2C)cc2c1C(=O)N([C@@H](C)C1CC1)C2]

Prepared by the same general method as described for Example 54 using Intermediate 111.

$^1$H NMR (300 MHz, DMSO-d$_6$) δ 0.25-0.29 (m, 1H), 0.41-0.47 (m, 2H), 0.59-0.63 (m, 1H), 1.13-1.19 (m, 1H), 1.32 (d, 3H), 2.06-2.28 (m, 2H), 2.36-2.46 (m, 1H), 2.50 (s, 3H), 2.52 (s, 3H), 2.71-2.84 (m, 1H), 3.60-3.76 (m, 2H), 3.80-3.87 (m, 1H), 4.73 (s, 2H), 4.99 (t, 1H), 5.01-5.07 (m, 1H), 6.79 (d, 1H), 7.55 (q, 1H), 7.73 (t, 1H), 7.89-7.96 (m, 2H), 8.04 (d, 1H), 11.57 (s, 1H).

m/z (ES+), [M+H]$^+$=597; acid, HPLC t$_R$=1.85 min.

Example 58

2-[(1S)-1-Cyclopropylethyl]-6-[2-({6-[(2R)-2-(hydroxymethyl)-5-oxopyrrolidin-1-yl]pyridin-2-yl}amino)-4-methyl-1,3-thiazol-5-yl]-N-methyl-3-oxo-2,3-dihydro-1H-isoindole-4-sulfonamide

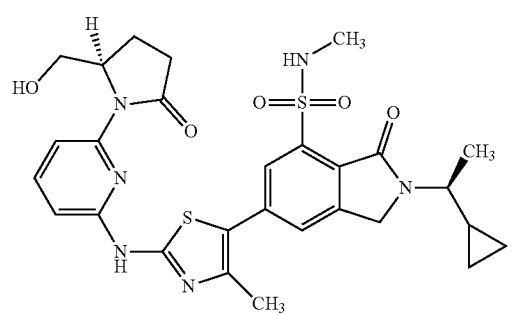 [SMILES: CNS(=O)(=O)c1cc(-c2sc(Nc3cccc(N4C(=O)CC[C@@H]4CO)n3)nc2C)cc2c1C(=O)N([C@@H](C)C1CC1)C2]

Prepared by the same general method as described for Example 54 using Intermediate 110.

$^1$H NMR (300 MHz, DMSO-d$_6$) δ 0.26-0.30 (m, 1H), 0.40-0.46 (m, 2H), 0.58-0.62 (s, 1H), 1.11-1.21 (m, 1H), 1.32 (d, 3H), 2.05-2.18 (m, 2H), 2.36-2.47 (m, 1H), 2.47 (s, 3H), 2.71-2.84 (m, 1H), 3.60-3.75 (m, 2H), 3.79-3.87 (m, 1H), 4.73 (s, 2H), 4.98 (t, 1H), 5.02-5.08 (m, 1H), 6.79 (d, 1H), 7.55 (d, 1H), 7.73 (t, 1H), 7.91-7.96 (m, 2H), 8.03 (s, 1H), 11.49-11.68 (br s, 1H). (3H obscured).

m/z (ES+), [M+H]$^+$=597.1; NH$_4$HCO$_3$, HPLC t$_R$=3.47 min.

Example 59

2-[(1S)-1-Cyclopropylethyl]-6-[2-({6-[4-(2-hydroxyethyl)-2-oxopiperazin-1-yl]pyridin-2-yl}amino)-4-methyl-1,3-thiazol-5-yl]-N-methyl-3-oxo-2,3-dihydro-1H-isoindole-4-sulfonamide

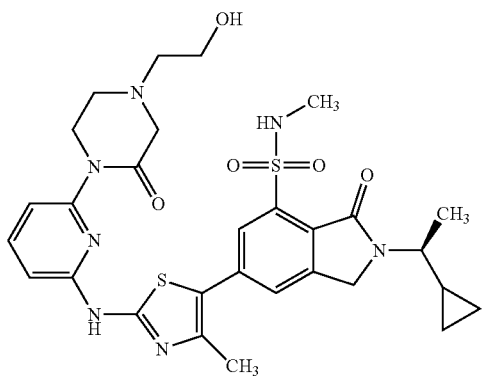 [SMILES: CNS(=O)(=O)c1cc(-c2sc(Nc3cccc(N4CCN(CCO)CC4=O)n3)nc2C)cc2c1C(=O)N([C@@H](C)C1CC1)C2]

Prepared by the same general method as described for Example 54 using Intermediate 106.

$^1$H NMR (400 MHz, DMSO-d$_6$) δ 0.28-0.32 (m, 1H), 0.41-0.47 (m, 2H), 0.60-0.64 (m, 1H), 1.14-1.20 (m, 1H), 1.33 (d, 3H), 2.48 (s, 3H), 2.90-2.94 (m, 2H), 3.34 (s, 2H), 3.58 (q, 2H), 3.62-3.69 (1H, m), 4.08-4.11 (m, 2H), 4.54 (t, 1H), 4.76 (s, 2H), 6.88 (d, 1H), 7.47 (d, 1H), 7.55-7.63 (m, 1H), 7.76 (t, 1H), 7.91 (d, 1H), 8.02 (d, 1H). (6H obscured).

m/z (ES+), [M+H]$^+$=626; acid, HPLC t$_R$=1.56 min.

Example 60

6-[2-({6-[(3S)-3-Hydroxy-2-oxopyrrolidin-1-yl]pyridin-2-yl}amino)-4-methyl-1,3-thiazol-5-yl]-3-oxo-N-(propan-2-yl)-2-[(2S)-1,1,1-trifluoropropan-2-yl]-2,3-dihydro-1H-isoindole-4-sulfonamide

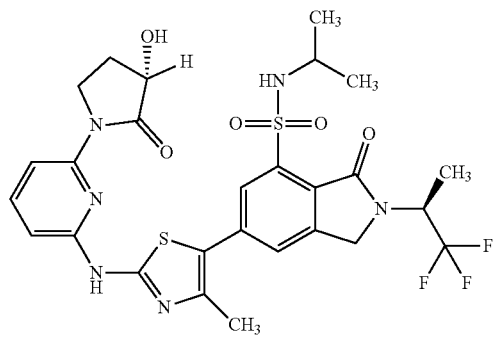 [SMILES: Cc1nc(Nc2cccc(N3CC[C@H](O)C3=O)n2)sc1-c1cc2c(c(S(=O)(=O)NC(C)C)c1)C(=O)N([C@@H](C)C(F)(F)F)C2]

Prepared by the same general method as described for Example 54 using Intermediate 112.

$^1$H NMR (300 MHz, DMSO-d$_6$) δ 0.97 (d, 3H), 1.05 (d, 3H), 1.54 (d, 3H), 1.84-1.93 (m, 1H), 2.46 (s, 3H), 3.26-3.33 (m, 1H), 3.94-4.03 (m, 1H), 4.29 (t, 1H), 4.37-4.45 (m, 1H), 4.64 (d, 1H), 4.86 (d, 1H), 5.12 (p, 1H), 5.84 (d, 1H), 6.79 (d, 1H), 7.25 (br s, 1H), 7.75 (t, 1H), 7.90 (d, 1H), 7.98 (s, 1H), 7.99 (s, 1H). (2H obscured).

$^{19}$F NMR (282 MHz, DMSO-d$_6$) δ -73.65.

m/z (ES+), [M+H]$^+$=639.2; TFA, HPLC t$_R$=2.01 min.

Example 61

2-[(2S)-Butan-2-yl]-N-methyl-6-(4-methyl-2-{[6-(2-oxo-1,3-oxazinan-3-yl)pyridin-2-yl]amino}-1,3-thiazol-5-yl)-3-oxo-2,3-dihydro-1H-isoindole-4-sulfonamide

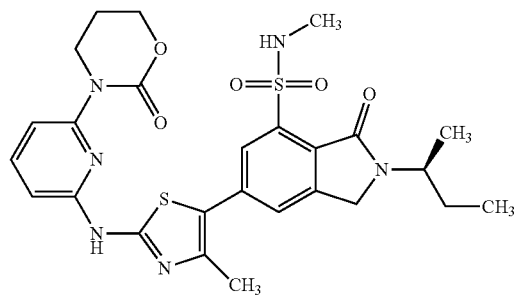 [SMILES: CC[C@H](C)N1Cc2cc(-c3sc(Nc4cccc(N5CCCOC5=O)n4)nc3C)cc(S(=O)(=O)NC)c2C1=O]

6-Bromo-2-[(2S)-butan-2-yl]-N-methyl-3-oxo-2,3-dihydro-1H-isoindole-4-sulfonamide (Intermediate 89, 135 mg), 3-{6-[(4-methyl-1,3-thiazol-2-yl)amino]pyridin-2-yl}-1,3-oxazinan-2-one (Intermediate 91, 125 mg), palladium (II) acetate (12 mg), cesium carbonate (245 mg) and tri-t-butylphosphonium tetrafluoroborate (31 mg) in DMF (5 mL) was microwaved at 110° C. for 30 min. The reaction mixture was passed through a 5 g flash column eluting with 50 mL of 5% ammoniated MeOH in DCM. The eluent was concentrated to give a dark-brown oil which was chromatographed eluting with 10-100% EtOAc in Heptane. The resultant product was purified by RPHPLC to give the title compound (80 mg)

$^1$H NMR (500 MHz, DMSO-d$_6$) δ 0.85 (t, 3H), 1.26 (d, 3H), 1.64 (p, 2H), 2.19 (p, 2H), 2.47 (s, 3H), 4.13 (t, 2H), 4.24 (q, 1H), 4.34-4.43 (m, 2H), 4.55 (d, 1H), 4.62 (d, 1H), 6.84 (d, 1H), 7.36 (d, 1H), 7.58 (q, 1H), 7.73 (t, 1H), 7.92 (d, 1H), 7.97 (s, 1H), 11.62 (s, 1H). (3H obscured).

m/z (ES+), [M+H]+570; pH10 (long) HPLC t$_R$=1.88.

Example 62

2-[(2S)-Butan-2-yl]-N-methyl-6-(4-methyl-2-{[6-(3-oxomorpholin-4-yl)pyridin-2-yl]amino}-1,3-thiazol-5-yl)-3-oxo-2,3-dihydro-1H-isoindole-4-sulfonamide

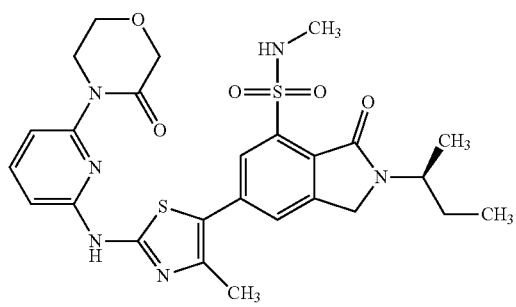 [SMILES: CC[C@H](C)N1Cc2cc(-c3sc(Nc4cccc(N5CCOCC5=O)n4)nc3C)cc(S(=O)(=O)NC)c2C1=O]

Prepared by the same general method as described for Example 61 using Intermediate 89 and Intermediate 90.

$^1$H NMR (600 MHz, DMSO-$d_6$) δ 0.84 (t, 3H), 1.26 (d, 3H), 1.64 (p, 2H), 2.47 (s, 3H), 2.51 (d, 3H), 4.03-4.10 (m, 2H), 4.15-4.20 (m, 2H), 4.21-4.27 (m, 1H), 4.30 (s, 2H), 4.56 (d, 1H), 4.63 (d, 1H), 6.89 (d, 1H), 7.56-7.62 (m, 2H), 7.77 (t, 1H), 7.91 (d, 1H), 7.98 (d, 1H), 11.65 (s, 1H).

m/z (ES+), MH+571; pH10, HPLC $t_R$=1.16 min.

Example 63

N-Methyl-6-(4-methyl-2-{[6-(2-oxoimidazolidin-1-yl)pyridin-2-yl]amino}-1,3-thiazol-5-yl)-3-oxo-2-[(2S)-1,1,1-trifluoropropan-2-yl]-2,3-dihydro-1H-isoindole-4-sulfonamide

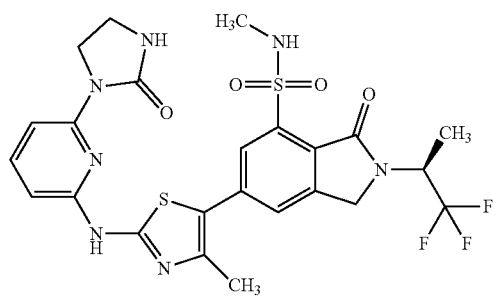 [SMILES: CNS(=O)(=O)c1cc(-c2sc(Nc3cccc(N4CCNC4=O)n3)nc2C)cc2c1C(=O)N([C@@H](C)C(F)(F)F)C2]

Prepared by the same general method as described for Example 52 using Intermediate 113.

$^1$H NMR (300 MHz, DMSO-$d_6$) δ 1.52 (d, 3H), 2.45 (s, 3H), 2.53 (s, 3H), 3.45 (t, 2H), 4.26 (t, 2H), 4.61 (d, 1H), 4.82 (d, 1H), 5.06-5.13 (m, 1H), 6.61 (d, 1H), 7.16 (q, 1H), 7.25 (s, 1H), 7.62 (t, 1H), 7.72 (d, 1H), 7.96 (d, 1H), 7.99 (d, 1H), 11.49 (s, 1H).

m/z (ES+), [M+H]$^+$=596.1; TFA, HPLC $t_R$=2.57 min.

Pharmacological Activity

Enzymatic Activity Assay for Recombinant Human PI3K α, β, δ and γ.

The activity of recombinant human PI3Kγ ((aa144-1102)-6His) and PI3Kα, β, δ (6-His(p110-p85α)) was determined by measuring the ADP level after phosphorylation of DiC8-PIP2 using a commercially available ADP-Glo™ kit from Promega. The assay was carried out in white low volume 384 well plates in a final volume of 14 μl at R.T. The assay conditions contained the following: 50 mM Tris buffer pH 7.4, 2.1 mM DTT, 3 mM $MgCl_2$, 0.05% CHAPS, 20 μM ATP, 80 μM DiC8-PIP2 and 1.2 nM PI3Kα, β, γ or 0.6 nM PI3Kδ. Potential inhibitors were made up in DMSO and then diluted in the assay to give a final concentration of not exceeding 1% (v/v) DMSO. A 10-point half-log dilution series of the inhibitors (highest concentration typically 0.1 μM for δ or γ and 33 μM for α or 1) was tested and the pIC50 determined using a 4-parameter logistic equation in a non-linear curve fitting routine. Routinely, inhibitors were pre-incubated with 3 μl of enzyme for 15 min prior to the addition of 2 μl substrate mixture for a further 60 min enzyme reaction. The phosphorylation was stopped with the addition of 3 μl ADP-Glo™ reagent (stop solution) followed by a 40 min incubation. Prior to detection 6 μl of ADP-Glo™ Kinase Detection Reagent was added and the plates were read in a micro plate reader using a Luminescence filter. All additions were followed by a short centrifugation step.

The results obtained are shown in Table 19 below.

TABLE 19

| Example | PI3Kδ $IC_{50}$ (nM) | PI3Kγ $IC_{50}$ (nM) | PI3Kα $IC_{50}$ (nM) | PI3Kβ $IC_{50}$ (nM) |
|---|---|---|---|---|
| 1 | 0.7 | 0.9 | 55 | 1362 |
| 2 | 19.6 | 0.9 | 263 | 3727 |
| 3 | 1.4 | 0.8 | 127 | 1177 |
| 4 |  | 1.0 | 16 | 250 |
| 5 | 0.7 | 1.2 | 38 | 4708 |
| 6 | 0.7 | 0.8 | 23 | 219 |
| 7 | 1.4 | 0.9 | 57 | 688 |
| 8 | 1.2 | 1.3 | 23 | 324 |
| 9 | 2.7 | 1.0 | 11359 | 33300 |
| 10 | 0.6 | 0.9 | 78 | 575 |
| 11 | 1.2 | 0.8 | 54 | 291 |
| 12 | 1.6 | 0.9 | 300 | 4096 |
| 13 | 1.1 | 0.8 | 68 | 1573 |
| 14 | 0.4 | 0.9 | 80 | 724 |
| 15 | 1.2 | 1.0 | 89 | 1165 |
| 16 | 0.8 | 1.2 | 55 | 539 |
| 17 | 0.3 | 1.1 | 48 | 677 |
| 18 | 0.3 | 0.8 | 25 | 231 |
| 19 | 1.0 | 1.0 | 18 | 168 |
| 20 | 0.7 | 0.9 | 37 | 543 |
| 21 | 0.6 | 1.1 | 19 | 103 |
| 22 | 1.3 | 1.0 | 38 | 328 |
| 23 | 19.4 | 1.3 | 368 | 4885 |
| 24 | 0.4 | 0.9 | 42 | 897 |
| 25 | 0.7 | 1.1 | 70 | 505 |
| 26 | 0.5 | 1.1 | 110 | 562 |
| 27 | 0.7 | 0.9 | 65 | 178 |
| 28 | 1.2 | 2.6 | 318 | 798 |
| 29 | 0.5 | 2.2 | 47 | 62 |
| 30 | 0.5 | 1.4 | 74 | 722 |
| 31 | 1.1 | 0.8 | 85 | 596 |
| 32 | 0.7 | 1.3 | 140 | 2055 |
| 33 | 1.4 | 1.2 | 472 | 3421 |
| 34 | 0.5 | 0.8 | 30 | 927 |
| 35 | 0.9 | 1.0 | 53 | 484 |
| 36 | 1.0 | 1.2 | 50 | 113 |
| 37 | 0.6 | 1.1 | 67 | 395 |
| 38 | 1.8 | 0.8 | 84 | 65 |
| 39 | 8.9 | 1.4 | 485 | 10424 |
| 40 | 1.7 | 1.6 | 104 | 729 |
| 41 | 0.9 | 1.3 | 72 | 298 |
| 42 | 0.8 | 1.0 | 69 | 286 |
| 43 | 1.0 | 1.0 | 40 | 284 |
| 44 | 1.5 | 1.2 | 72 | 518 |
| 45 | 1.0 | 0.8 | 33 | 257 |
| 46 | 0.8 | 1.0 | 24 | 123 |
| 47 | 4.4 | 1.3 | 97 | 824 |
| 48 | 0.7 | 1.5 | 19 | 199 |
| 49 | 2.6 | 1.9 | 87 | 800 |
| 50 | 0.8 | 1.4 | 54 | 271 |
| 51 | 1.1 | 1.5 | 134 | 415 |

TABLE 19-continued

| Example | PI3Kδ IC$_{50}$ (nM) | PI3Kγ IC$_{50}$ (nM) | PI3Kα IC$_{50}$ (nM) | PI3Kβ IC$_{50}$ (nM) |
|---|---|---|---|---|
| 52 | 18.9 | 22.5 | | |
| 53 | 0.7 | 1.4 | 64 | 264 |
| 54 | 0.5 | 0.9 | 14 | 325 |
| 55 | 1.1 | 0.9 | 40 | 386 |
| 56 | 0.5 | 1.0 | 26 | 249 |
| 57 | 0.7 | 1.2 | 11 | 85 |
| 58 | 2.9 | 1.2 | 43 | 998 |
| 59 | 0.7 | 0.9 | 27 | 481 |
| 60 | 0.5 | 1.2 | 57 | 322 |
| 61 | 2.2 | 1.0 | 80 | 459 |
| 62 | 2.1 | 0.8 | 162 | 1152 |
| 63 | 0.7 | 1.2 | 32 | 274 |

The invention claimed is:

1. A compound, wherein the compound is:

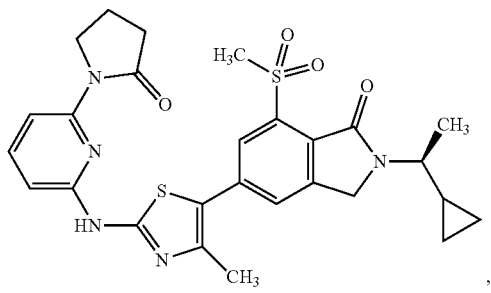 [SMILES: Cc1nc(Nc2cccc(N3CCCC3=O)n2)sc1-c1cc2c(c(S(C)(=O)=O)c1)C(=O)N([C@@H](C)C1CC1)C2]

or a pharmaceutically acceptable salt thereof.

2. A pharmaceutical composition comprising a pharmaceutically acceptable adjuvant, diluent, or carrier and the compound as claimed in claim 1, or a pharmaceutically acceptable salt thereof.

3. A compound, wherein the compound is:

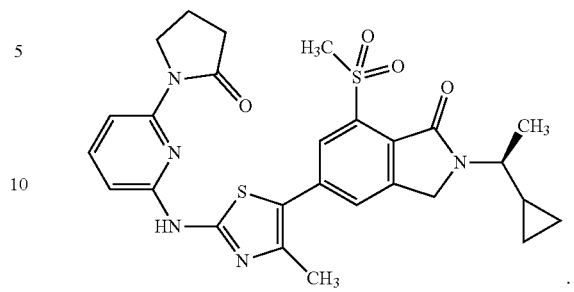

4. A pharmaceutical composition comprising a pharmaceutically acceptable adjuvant, diluent, or carrier and the compound as claimed in claim 3.

5. A pharmaceutically acceptable salt of a compound, wherein the compound is:

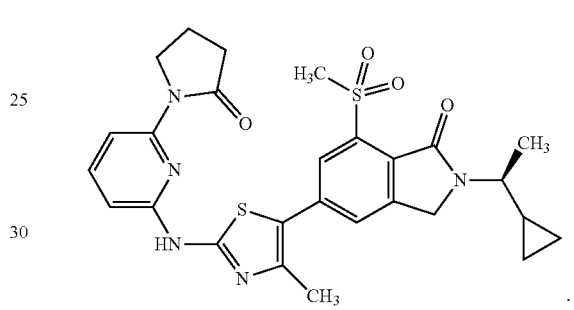

6. A pharmaceutical composition comprising a pharmaceutically acceptable adjuvant, diluent, or carrier and the pharmaceutically acceptable salt of the compound as claimed in claim 5.

* * * * *